US012612615B2

(12) United States Patent
Lubys et al.

(10) Patent No.: US 12,612,615 B2
(45) Date of Patent: Apr. 28, 2026

(54) ISOLATED NUCLEIC ACID BINDING DOMAINS

(71) Applicant: THERMO FISHER SCIENTIFIC BALTICS, UAB, Vilnius (LT)

(72) Inventors: Arvydas Lubys, Vilnius (LT); Algirdas Grybauskas, Vilnius (LT); Dovile Strepetkaite, Vilnius (LT); Zana Kapustina, Vilnius (LT); Aliona Markina, Vilnius (LT); Paulius Mielinis, Palanga (LT)

( * ) Notice: Subject to any disclaimer, the term of this patent is extended or adjusted under 35 U.S.C. 154(b) by 1167 days.

(21) Appl. No.: 17/594,277

(22) PCT Filed: Apr. 27, 2020

(86) PCT No.: PCT/EP2020/061656
§ 371 (c)(1),
(2) Date: Oct. 8, 2021

(87) PCT Pub. No.: WO2020/216966
PCT Pub. Date: Oct. 29, 2020

(65) Prior Publication Data
US 2022/0307009 A1 Sep. 29, 2022

Related U.S. Application Data

(60) Provisional application No. 63/012,795, filed on Apr. 20, 2020, provisional application No. 62/839,473, filed on Apr. 26, 2019.

(51) Int. Cl.
*C12N 15/10* (2006.01)
*C07K 14/195* (2006.01)
(52) U.S. Cl.
CPC ........ *C12N 15/1013* (2013.01); *C07K 14/195* (2013.01); *C12N 15/101* (2013.01); *C12Q 2522/10* (2013.01)
(58) Field of Classification Search
CPC ............ C12Q 2522/10; C12N 15/1013; C12N 15/101; C12N 15/1006; C12N 25/1003; C07K 14/195
See application file for complete search history.

(56) References Cited

U.S. PATENT DOCUMENTS

2013/0035239 A1   2/2013   Kong et al.
2018/0282786 A1*  10/2018   Pugia ..................... C12Q 1/682

FOREIGN PATENT DOCUMENTS

| EP | 1400589 A1 | 3/2004 |
| WO | WO-2005085440 A1 | 9/2005 |
| WO | WO-2006046076 A2 | 5/2006 |
| WO | WO-2009102632 A2 | 8/2009 |
| WO | WO-2009143500 A2 | 11/2009 |
| WO | WO-2014064223 A1 | 5/2014 |
| WO | WO-2019020798 A1 | 1/2019 |

OTHER PUBLICATIONS

Altschul S.F., et al., "Gapped BLAST and PSI-BLAST: New Generation of Protein Database Search Programs," Nucleic Acids Research, 1997, vol. 25 (17), pp. 3389-3402.
Database UniProt [Online] Feb. 22, 2012 (Feb. 22, 2012), SubName: Full=Competence protein ComEA-related protein {ECO:0000313|EMBL:AEV17292.1}; retrieved from EBI accession No. UNIPROT:G8NCV6 Database accession No. G8NCV6.
Database UniProt [Online] Apr. 5, 2011 (Apr. 5, 2011), SubName: Full=ComEA protein {EC0:0000313|EMBL:EFW89502.1}; retrieved from EBI accession No. UNIPROT:E8JM87 Database accession No. E8JM87.
Doherty, A. et al., "The helix-hairpin-helix DNA-binding motif: a structural basis for nonsequence-specific recognition of DNA", Nucleic Acids Research, vol. 24, No. 13, Jul. 1, 1996, 2488-2497.
PCT/EP2020/061656, International Search Report and Written Opinion, Sep. 24, 2020, 27 pages.

* cited by examiner

*Primary Examiner* — Sarae L Bausch

(74) *Attorney, Agent, or Firm* — Klarquist Sparkman, LLP

(57) ABSTRACT

Nucleic acid binding domains are described for use in isolating nucleic acid. Compositions and kits comprising these nucleic acid binding domains are also described. These nucleic acid binding domains may be used in a variety of methods.

18 Claims, 25 Drawing Sheets

Specification includes a Sequence Listing.

| ORF | Amino acid sequence | $K_d$ (dsDNA) | | $K_d$ (ssDNA) | | $K_d$ (dsRNA) | | $K_d$ (ssRNA) | |
|---|---|---|---|---|---|---|---|---|---|
| | | ph 6.0 | ph 7.5 | ph 6.0 | ph 7.5 | ph 6.0 | ph 7.5 | ph 6.0 | ph 7.5 |
| ComEA1 | GDGRIDLNTATADQLQTILPGIGPVLAQRIIDHRASIG GFTSVEQLHDVTGIGDRRFAELRDLVYGGAP | 1-3.3 µM | - | 100-333 nM | - | 100-333 nM | - | 100-333 nM | 0.33-1 µM |
| ComEA2 | WAFPVELNTASLEDLMSIPGIGPVKAQRIIDYRESH GGFSSVEELKNVSGIGEKTILEKISRYVTVEG | 10-33 nM | 1-3.3 µM | 1-3.3 µM | - | 100-333 nM | 0.33-1 µM | 0.33-1 µM | 33-100 nM |
| ComEA3 | PEPISLNRASLEELEALPGIGPTLARRIVEGRPYGKV EDLLRVKGIGPATLERLRPYVRP | 33-100 nM | - | 1-3.3 µM | - | 33-100 nM | - | 100-333 nM | 0.33-1 µM |
| ComEA4 | SSGGKINLNTADEAALQTILPGIGPTLARRIVEYRAKN GPFTSVEDLAKVPGIGPRRLEQLREYVCAP | 1-3.3 µM | - | 1-3.3 µM | - | 100-333 nM | - | 100-333 nM | 3.3-10 µM |

```
ComEA11    EKDDLLNINSADLSELQTLSGVGPSKAQSIISYREEPGPFKSIDQLLEVRGIGEKT-IEE    59
ComEA14    GSTEMVNVNTADEQAMQNLPGIGPAKAKAIIQYRDEHGPFNSLDELTDVSGIGEKS-LEK    59
ComEA5     -ELRVIELNAADSAQLVDIIGIGPVLALRIAKYRNRLGGFHSKEQLREIFGIDSLK-YAE    58
ComEA6     -ELRVVELNAADSAQLVDIIGIGPVLAVRIAKYRDRLGGFHTKEQLQEVFGIDSLK-YAE    58
ComEA3     --PEPISLNRASLEELEALPGIGPTLARRIVEGR------PYGKVEDLLRVKGIGPAT-LER    53
ComEA1     --GDGRIDLNTATADQLQTLPGIGPVLAQRIIDHPASIGGFTSVEQLHDVTGIGDRR-FAE    58
ComEA4     SSGGKINLNTADEAALQTLPGIGPTLARRIVEYRAKNGPFTSVEDLAKVPGIGPRR-LEQ    59
ComEA10    SPKHLVDLNRATIGDLEQLPGIGPQTAERVVRFREHNGPYPSIDDLKKVGGIGERT-LEK    59
ComEA2     VVAFPVELNTASLEDLMSIPGIGPVKAQRIIDYRESHGGFSSVEELKNVSGIGEKT-LEK    59
ComEA15    ADSAQINLNTASLEELQTISGIGAKRAQDIIDYRDNNGGFSSVDDLKNVSGIGEKT-LEK    59
ComEA7     --QLNKISFDEADSIVLQIVPGVGPATAGRIIKPRDAIGGMHTSEQLLDVYGMSFEV-MER    58
ComEA8     -SFNKITFSEATAIELQMVQGVGPFLSARIDDYRESLGGFHSPEQILEVYGVDAEL-AEK    58
ComEA9     --HLAIFDLNTADTTQLMQIRGIGRGISARIVAYRAPLGGFVPAEQMAEIYSLRDAPDLID    59
ComEA12    INYTVKDINNATAIDLQVVSGIGEKISSRIVKFRDRLGGFVVNEQLQDVYGLDKEV-LNR    59
ComEA13    KSIDIYDLNTATEEDLQKIKGIGPAYSERIVKYRNLLGGFSDTTQLHEVYGLKPET-ISR    59
                ..   *    :   :  *:*   :   :    *         ::   :  .:

ComEA11    WKDKIKFQ----  67  (SEQ ID NO: 11)
ComEA14    MKPNMSLQ---   67  (SEQ ID NO: 14)
ComEA5     IKNQVRVDQ--   67  (SEQ ID NO: 5)
ComEA6     IKNQVRVEQ--   67  (SEQ ID NO: 6)
ComEA3     LRPYVRP----   60  (SEQ ID NO: 3)
ComEA1     LRDLVYVGGAP   69  (SEQ ID NO: 1)
ComEA4     LREYVCAP---   67  (SEQ ID NO: 4)
ComEA10    ISPWVTV----   66  (SEQ ID NO: 10)
ComEA2     ISRYVTVEG--   68  (SEQ ID NO: 2)
ComEA15    LKAEVTVD---   67  (SEQ ID NO: 15)
ComEA7     VFEYFEFTP--   67  (SEQ ID NO: 7)
ComEA8     IYSVFAFES--   67  (SEQ ID NO: 8)
ComEA9     SLRKYTFVKA-   69  (SEQ ID NO: 9)
ComEA12    LLKQFKVI---   67  (SEQ ID NO: 12)
ComEA13    LLEQFRIL---   67  (SEQ ID NO: 13)
```

FIG. 12

```
GI:503303602|194-253    --------------------------------------------------------------    0
GI:15606502|180-241     --------------------------------------------------------------    0
GI:502729464|183-245    --------------------------------------------------------------    0
GI:502756584|179-241    --------------------------------------------------------------    0
GI:288832121|477-530    --------------------------------------------------------------    0
GI:289596582|111-163    --------------------------------------------------------------    0
GI:327400296|474-526    --------------------------------------------------------------    0
GI:284162061|486-537    --------------------------------------------------------------    0
GI:490183434|495-532    --------------------------------------------------------------    0
GI:15644349|495-532     --------------------------------------------------------------    0
GI:502660080|495-543    --------------------------------------------------------------    0
GI:501263013|495-532    --------------------------------------------------------------    0
GI:289596960|482-522    --------------------------------------------------------------    0
GI:503302539|507-546    --------------------------------------------------------------    0
GI:248103390|525-579    --------------------------------------------------------------    0
GI:390960450|525-580    --------------------------------------------------------------    0
GI:83589893|1129-1198   --------------------------------------------------------------    0
GI:760030306|1406-1449  --------------------------------------------------------------    0
GI:501435520|39-97      --------------------------------------------------------------    0
GI:501542092|303-361    -----------PQFFPIEINKATYEQLLRIPGIGPISAKKITKARKE-QKIRDIKDLKK    47
GI:752795678|309-345    -----------PQFFPVDVNRASYRELL&VPGIGPTIARRILEARKE-G---------    37
GI:752619530|477-541    --------------------------------------------------------------    0
GI:504063068|476-540    --------------------------------------------------------------    0
GI:752787433|458-522    --------------------------------------------------------------    0
GI:501003427|456-520    --------------------------------------------------------------    0
GI:499609813|492-556    --------------------------------------------------------------    0
GI:493910404|485-549    --------------------------------------------------------------    0
GI:489614004|480-544    --------------------------------------------------------------    0
GI:503553382|477-541    --------------------------------------------------------------    0
GI:503063630|477-541    --------------------------------------------------------------    0
GI:501226561|477-541    --------------------------------------------------------------    0
GI:502914941|477-541    --------------------------------------------------------------    0
GI:502759661|477-541    --------------------------------------------------------------    0
GI:502778332|41-100     --------------------------------------------------------------    0
GI:506219682|128-192    --------------------------------------------------------------    0
GI:752787889|141-201    --------------------------------------------------------------    0
GI:752790358|493-552    --------------------------------------------------------------    0
GI:22299382|505-564     --------------------------------------------------------------    0
GI:502780313|58-115     --------------------------------------------------------------    0
GI:753950367|129-188    --------------------------------------------------------------    0
GI:504329537|46-101     --------------------------------------------------------------    0
GI:502258539|50-262     TITNAAKSKAENTRDTELDLNTASNVDLTSLPGIGEVKASEIVKYRSEHGGFKAIDELIN    120
GI:755152313|102-162    --------------------------------------------------------------    0
GI:503040608|149-209    --------------------------------------------------------------    0
GI:83589434|160-222     --------------------------------------------------------------    0
GI:489614667|234-294    --------------------------------------------------------------    0
GI:217967490|122-186    --------------------------------------------------------------    0
GI:501543178|120-183    --------------------------------------------------------------    0
GI:503055614|155-217    --------------------------------------------------------------    0
GI:503803183|155-217    --------------------------------------------------------------    0
GI:503197882|155-217    --------------------------------------------------------------    0
GI:503163696|155-217    --------------------------------------------------------------    0
GI:503177334|155-217    --------------------------------------------------------------    0
GI:506388026|157-217    --------------------------------------------------------------    0
GI:503135740|157-217    --------------------------------------------------------------    0
GI:503589690|158-217    --------------------------------------------------------------    0
GI:503554242|143-203    --------------------------------------------------------------    0
GI:503082661|143-203    --------------------------------------------------------------    0
GI:499334810|132-194    --------------------------------------------------------------    0
GI:501225752|139-199    --------------------------------------------------------------    0
GI:503828681|139-202    --------------------------------------------------------------    0
GI:502759364|136-199    --------------------------------------------------------------    0
GI:502915162|136-199    --------------------------------------------------------------    0
GI:753908752|6-85       --------------------------------------------------------------    0
GI:760031704|172-231    --------------------------------------------------------------    0
GI:501268304|42-180     -----------VVAFPVELNTASLEDLMSIPGIGPVKAQRIIDYRESHGGFSSVEELKN    48
GI:506400261|42-180     -----------VTSFPIDLNSASVEDLMSIPGIGPVKAQRIVEYRRIRGNFSTVEELTN    48
GI:501004996|42-182     ----------AEQIIDINSATFEQLVSLPGIGPTKAKSIINYREKVGEFLSIDDLLN    47
GI:503697337|46-182     ----------EFPIDINKASYEELLVLPGIGPTKARAIVETRQKYGPFESLPDLAK    46
GI:503673264|26-85      --------------------------------------------------------------    0
GI:752791330|1-60       --------------------------------------------------------------    0
GI:490204927|51-189     -----------SQIIDLNKADLEQLMSLPGIGTVKAKATISYRQAHGNFNSIDDLIN    46
```

FIG. 13 (cont.)

```
GI:503303602|194-253   -----------------------------SGKVNVNSAG-----------KKLLMAL          17
GI:156066502|180-241   -----------------------------SKGKVNINTAP-----------LLVLYSL          18
GI:502729464|183-245   -----------------------------SSGKININTAN-----------SYILMAL          18
GI:502756584|179-241   -----------------------------SSGKININTAP-----------LIVLMAL          18
GI:288932121|477-530   --------------------------LDVNKAK-----------LYQLESI          14
GI:289596582|111-163   ------------------------------INVCP-----------LEELLST          12
GI:327400296|474-526   --------------------------EILDVNRAS-----------LQQLEAI          16
GI:284162061|486-537   --------------------------LRPNTAK-----------LYQLEAV          14
GI:490183434|495-532   ---------------------------INSMS-----------LEELTAI          12
GI:15644349|495-532    ---------------------------INSMS-----------LEELTAI          12
GI:502660280|495-543   ---------------------------INSMS-----------LEELTAI          12
GI:501268013|495-532   ---------------------------INSMS-----------LEELTAI          12
GI:289596960|482-522   -------------------------PLNVNSAS-----------PSTLESI          15
GI:503302539|507-546   -------------------------PLNVNEAS-----------VKLLSFI          15
GI:240103390|525-579   -------------------------VPINVNPES-----------PKVLQLI          16
GI:390960450|525-580   -------------------------IPVDTNRES-----------PKLLQYL          16
GI:83589893|1129-1198  -------------------------ERIDLQKADASRFLVEPGKLLPPLAAL          27
GI:760032306|1406-1449 ---------------------------------------------------L          1
GI:501435520|39-97     -----------------------NDLKIDINTAD-----------IITLQRI          18
GI:501542092|303-361   L----GI-QV---------------------------------------------          52
GI:752795678|309-345   ---------------------------------------------------........          37
GI:752619530|477-541   ------------------------VNYVGVRLNTAS-----------EHLLFYI          19
GI:504063088|476-540   ------------------------VRLVGVRLNTAS-----------AALLQYI          19
GI:752787433|458-522   ------------------------VNMVGVDLNTAS-----------AKLLEYV          19
GI:501003427|456-520   ------------------------VNQLGTDLNSAS-----------SKLLEHV          19
GI:492609813|490-556   ------------------------VNAVGVDVNTAS-----------VPLLSRV          19
GI:499510404|485-549   ------------------------VNAVGVDLNTAS-----------PSLLQYV          19
GI:489614004|480-544   ------------------------VNSVGVDLNTAS-----------PSLLSYI          19
GI:503553382|477-541   ------------------------VNSVGVDLNTAS-----------VSLLKYV          19
GI:503063630|477-541   ------------------------VNSVGVDLNTAS-----------VSLLKYV          19
GI:501226561|477-541   ------------------------VNSVGVDLNTAS-----------VSLLKYV          19
GI:502914941|477-541   ------------------------VNSVGVDLNTAS-----------VSLLKYV          19
GI:502759661|477-541   ------------------------VNSVGVDLNTAS-----------VSLLKYV          19
GI:502778332|41-100    -------------------------KIAPVHINTAP-----------LAQLETL          18
GI:506219682|128-192   -------------------------SSGGKININTAD-----------EAALQTL          19
GI:752787889|141-201   --------------------------RIDLNTAT-----------ADQLQTL          15
GI:752790358|493-552   --------------------------RVNLNTAT-----------AASLETL          15
GI:22299882|505-564    --------------------------RVNLNTAT-----------AASLETL          15
GI:502780313|58-115    -------------------------QKVNLNTAS-----------QAEIESL          16
GI:753950367|129-188   -------------------------PSRVKVSLNRAT-----------LEELEAL          19
GI:504309537|46-101    --------------------------ISLNRAS-----------LEELEAL          14
GI:502258539|50-262    VKGIGRATLDKIRNLVRVGSVSTN-VPDKSENSGKINVNTAT-----------LQELVAL          168
GI:755150313|102-162   --------------------------RIDINRAS-----------AAELEAL          15
GI:503040608|149-209   --------------------------RININTAG-----------LEELDKL          15
GI:83589434|160-222    --------------------------GGKVNINTAG-----------LAELDSL          17
GI:489614667|234-294   --------------------------KININTAT-----------VEELDSI          15
GI:217967490|122-186   -------------------------SKSDKVNINTAS-----------KEELESL          19
GI:501543178|120-183   -------------------------KKGKVNINTAS-----------KEELESL          18
GI:503055614|155-217   -------------------------EGKININTAT-----------KEELKTL          17
GI:503808183|155-217   -------------------------EGKININTAT-----------KEELKTL          17
GI:503197882|155-217   -------------------------EGKININTAT-----------KEELKTL          17
GI:503168696|155-217   -------------------------EGKININTAT-----------KEELKTL          17
GI:503177334|155-217   -------------------------EGKININTAT-----------KEELKTL          17
GI:506388026|157-217   --------------------------KININTAT-----------KEELKTL          15
GI:503195740|157-217   --------------------------KININTAT-----------KEELKTL          15
GI:503589690|158-217   ---------------------------YNINTAD-----------QKELETL          14
GI:503554242|143-203   --------------------------KININTAT-----------KEELDTL          15
GI:503062661|143-203   --------------------------KININKAT-----------KEELDTL          15
GI:499334810|132-194   -------------------------AKKVNINTAT-----------KEELQTL          17
GI:501225752|139-199   --------------------------KININTAT-----------REELQTL          15
GI:503828681|139-202   -------------------------KSEKININTAT-----------KEELQTL          18
GI:502759964|136-199   -------------------------KSEKININTAT-----------KEELETL          18
GI:502915162|136-199   -------------------------KSEKININTAT-----------KEELETL          18
GI:753908752|6-65      -------------------------EIKIDLYTAS-----------ETQLTKI          17
GI:760031704|170-231   ---------------------------YNINTAG-----------QASLETV          14
GI:501268304|42-180    VSGIGEKTLEKISRYVTVEGVEQ-----RIKREVTKLNVNTAS-----------VEELETL          93
GI:506400261|42-180    VSGIGEKTLEKISKYVTVEGVEQ-----PPPSEVTKLNVNTAS-----------LEELETL          93
GI:501004996|42-182    VSGIGESTLKKIKPFIKIKTANVITNSPSGSEDVKININRAS-----------VEELMKL          96
GI:503697337|46-182    VSGIGKKTVEPLANFVKTEGTVFVK----MEEFRRTNVNIAT-----------LEQLCEL          91
GI:503673264|26-85     --------------------------INLNVAG-----------QEELANL          14
GI:752791330|1-60      --------------------------KIDINQAT-----------VEELEKL          15
GI:490204927|51-189    VTGIGPSTLEKIRDYVFVSKTNEVQI-RHNNELKKININKAD-----------EKQLEKL          94
```

FIG. 13 (cont.)

```
GI:503303602|194-253    SDRITPTLADSIIEA----PPIRKLQDL-LDIPGPTRELYFEIRPIIT-         60
GI:15606502|180-241     DRDIDMELAK&IADYPKE-NPPKQLKDL-LMVDSMTLDILYRIQ@F-----       62
GI:502729464|183-245    DPRIDQALASKIIERRNR-EPPKKVEDL-LLVDGFTFDILYSVRDLV---       63
GI:502756584|179-241    DDPRIDEDLARRIIEPRDK-EPFRRVEDL-LLVEGFTLDILYSVRDLV---       63
GI:288932121|477-530    -PGIGKTTAAKIISAK----PFRSLEEL-KDLIGEEKF--KILLPYIS-        54
GI:289596582|111-163    -SLIGKKLAIRIMENR----PYESMEEL-RKVPGIGEK--RLSRLQARF        53
GI:327400298|474-526    -PGIGKATAAKIVANR----PFRNVEEI-ASLVE-NFD--EIKDFF---        53
GI:284162061|486-537    -PGIGKALAGKIIANR----PYSSLDEL-RDVLGDVFD--RVKHFF---        52
GI:490183434|495-532    --PSIGSALASKIILNR---PFRSWEDL-KKV----------------        38
GI:15644349|495-532     -PGIGSALARKIILNR---PPFRSWEDL-KKV----------------        38
GI:502660280|495-543    -PGIGNALAKKIILNR----PFRSWEDL-KKVVPAET-----VNFLRK-        49
GI:501268013|495-532    -PGIGRALAPKIILNR----PFRSWEDL-KKV----------------        38
GI:289596960|482-522    -PGMGEKKAAEIIRKR----PFKNMKSL-QEI----------------        41
GI:503302539|507-546    -PGISRKTASDIVLPR----PFKSKEEL-LK-----------------        40
GI:240103390|905-978    -PGIGKKTATRILAKR----PFRSPEEF-FEVVDPGVR---EVLRDLV--       55
GI:390960450|525-580    -PGIGKKTAVKILSKP-----PFKNKDEF-FSVVGEDKR--EMLGGIIR-       56
GI:83589893|1129-1198   -PGVGRAAAEAIVRARQE-RPFTSVEDL-QYRSRVSKTVIEALEKR---        70
GI:760032306|1406-1449  -PGLGDSAQAIVEARAQ-GPFHSKEDL-KNRARLNKAVMELLEGH---        44
GI:501435520|39-97      -PYIGEKTAELIIKDRKIRGGYTDINQL-KWV-----KNFDKIKPYIK-        59
GI:501542092|303-361    --------------------------------------ERCKNYI---        59
GI:752795676|309-345    ----------------------------------------------        37
GI:752619530|477-541    -SGLNARMARNIVEYRKQVGLFKKREDL-LKVKGIGNKAFEQAAGFCR-        65
GI:504063068|476-540    --SGITPKLAENIVKIREENGPFKERKEL-LKVEGPGPKAFEQAAGFLR-       65
GI:752787433|458-522    -SGITPSLAKKIVKIYREKHGKFIERNQL-LNIEGLGEKTFEQCAGFLR-       65
GI:501003427|456-520    -AGITPSLAKKIVNFRKKIGKFTERKQL-LEIEGLGQKTYTQCAGFLR-        65
GI:499609813|492-556    --SGITASLAQKIVAIRDANGPFRTRAQL-REVPRLGPKAFEQCAGFLR-       65
GI:489510404|485-549    -AGIKASVARAIVEYREKHGKFPSRREL-LKVSGLGPKAFEQCAGFLR-        65
GI:489614004|480-544    --SGINSVIAKNIVEIPETNGKSKRREEL-KKVKRLGDXTFEQCAGFLR-       65
GI:503553382|477-541    -AGINGTIAKNIVEYRNTVGKFRNRNEL-KKVKRLGEGTFTQCAGFLR-        65
GI:503063630|477-541    -SGINASTAKNIVEYREVGQFRNRNEL-KNVKRLGDATFTQCAGFLR-         65
GI:501226561|477-541    -SGINAAIAKNIVEYRNQIGKFTNREQL-KNVKRLGDTTFTQCAGFLR-        65
GI:502914941|477-541    -SGINTAIAKNIVEYRNQIGKFTSREQL-KNVKRLGEATFTQCAGFLR-        65
GI:502759661|477-541    -SGINTVIAKNIVEYRNQIGKFTSRQL-KNVKRLGBATFTQCAGFLR-         65
GI:502778332|41-100     -PGIGPKLAQEIIKHR-----PYKHAHDLQSKVKGISPSLWKKIAPHV--       60
GI:506019682|128-192    -PGIGPTLARRIVEYPAKNGPFTSVEDL-AKVPGIGPRRLEQLREYVC-        65
GI:752787889|141-201    -PGIGPVLAQRIIDKRASIGGFTSVEDL-RDVTGIGDRRFAELRDLVY-        61
GI:752798358|493-552    -PGVGPKLAAEIIRAREQK-PFNSLADL-DAVPGVGEKLLERLRDRVT-        60
GI:22299882|505-564     -PGVGSKLAAEIIPARERK-PFQSLADL-DAVPGVGPKLLERLRDPVT-        60
GI:502780313|58-115     -SGIGPALAQRIIEGR-----PYRTLEEL-ERVKGIGPKLLERLRPYVT-      58
GI:753958367|129-188    -PGIGPTKARRIMEXR------PYLRVEDL-LPVPGIGEXTLERLRPYV---    60
GI:504329537|46-101     -PGIGPTLAPRIVEGR----PYGKVEDL-LRVKGIGPATLEPLRPYVR-        56
GI:502258539|50-262     -PGIGPVLAERIIDPREHNGKFAKPEDL-LKVSGIGIKTLSKFREMI---       213
GI:755152313|102-162    -PGIGPALAQPIVADREVNGPFRRPQDL-SRVTGIGEKTLAPLLFYTT-        61
GI:503040608|149-209    -PGIGPALAQRIIDYRNQHGPFKSVEEL-KNVSGIGEKKFEELKDLVK-        61
GI:83589434|160-222     -PGIGPTLAQRILDYPTQKGPFRTIEDL-QNVSGIGAKKFADLKDLIT-        63
GI:489614667|234-294    -PGIGPAIAAKIVAYREQNGKFKSIEDI-MNVSGIGQSKPNNIKDFIT-        61
GI:217967490|122-186    -PGIGPTLAQRIIEYREENGPFGSAEDL-LNVEGIGEKKLERIRIQIT-        65
GI:501543178|120-183    -PGIGPTLAQRIIEYREENGVFTSAEDL-LNVKGIGEKKLERIIFDQIT-       64
GI:503055614|155-217    -DRIGDKLAERIIEYRQNHGPFKSTEEI-KNVNGIGEKIFESIKDFIT-        63
GI:503808183|155-217    -DRIGDKLAERIIEYRQKHGPFKSIEEI-KNVNGIGEKIFESIKDSIT-        63
GI:503197882|155-217    -DRIGDKLAERIIEYRQKHGPFKSIEEI-KNVNGIGEKIFESIKDSIT-        63
GI:503168696|155-217    -DRIGDKLAERIIEYRQKHGPFKSIEEI-KNVNGIGEKIFESIKDSIT-        63
GI:503177334|155-217    -DRIGDKLAERIIEYRQKHGPFKSIEEI-KNVNGIGEKIFESIKDSIT-        63
GI:506388026|157-217    -NRIGDKLAERIIEYPQKHGPFKSIEEI-KNVNGIGEKIFESIKDSIT-        61
GI:503195740|157-217    -NRIGDKLAERIIEYRQKHGPFKSIEEI-KNVNGIGEKIFESIKDSIT-        61
GI:503589690|158-217    -PGIGPSLAQRIIQYRETNGPFKVPEDI-KNVSGIGDKRFEQLKDYIT-        60
GI:503554242|143-203    -PGIGEVTAQKIIDFREQBHGNFQRIEDI-MNVSRIGPKLFEQIKDKIT-       61
GI:503062661|143-203    -PGIGEVTAQRIIDFREQHGNFQRIEDI-MNVSRIGPKLFEQIKDNIT-        61
GI:499334810|132-194    -PGIGPVTAERIIEPRETNGPFKKIEDI-MNVPRIGPKMFEQIKDKIT-        63
GI:501229752|139-199    -PGIGPVTAERIIEFRESKGPFKKIEDI-VNVSRIGPKMFEQIKDKIT-        61
GI:503828681|139-202    -PGIGPVTAERIIEFRESKGSPFKKIEDI-MNVPRIGPKMFEQIKDKIT-       64
GI:502759964|136-199    -PGIGPVTAERIIEFRENKGPFKKIEDI-MNVPRIGPKMFEQIKDKIT-        64
GI:502915162|136-199    -PGIGPVTAERIIEFRENKGPFKKIEDI-MNVPRIGPKMFEQIKDKIT-        64
GI:753908752|6-65       -PSIGEKTAKKIIQVREHYG-FSSVKDL-NKIKGIGEKTYEKIRKY----       60
GI:760031704|170-231    -PGIGPALARAIIYRTEHGPFQSVDDL-INVSGIGSKTLEKIRPYYT-        60
GI:501268304|42-180     -PYIGEVKAKAIVEXREFNGPFRSPEDL-LDVPGIGEKTLEKIRGKIT-        139
GI:506400261|42-188     -PYIGEKAPATIEYREEHGPFSSPEDL-LNVPGIGEKTLEPIPGKTT-         139
GI:501004996|42-182     -PGIGKVKAQEIIEFRKKPGNVQSFEDL-LKVKGIGKKTLEKIKPFI---       141
GI:503697337|46-182     -PGIGEVKASQIIKYRQENGPFKKPEDL-LKVPGIGPKTLEKIKDFIT-        137
GI:503673264|26-85      -PGVGPKIAAAIVEYREKYGPFKSVEDL-LKIKGIGMKKLEKIRKY----       60
GI:752791330|1-60       -PSIGPKIAKNIVEIPETNGPFKRSIEEL-LKVKGIGPKKLEQIKKYL--       60
GI:490204927|91-189     -PGIGPTKAFRIIEYREKNGKFNSLREL-LNVNGIGPKTLEFIKPYL--        139
```

ISOLATED NUCLEIC ACID BINDING DOMAINS

SEQUENCE LISTING

The instant application contains a Sequence Listing which has been submitted electronically in ASCII format and is hereby incorporated by reference in its entirety. Said ASCII copy, created on Apr. 15, 2020, is named LT01327PCT2_SL.txt and is 96,930 bytes in size.

DESCRIPTION

Field

This application pertains to nucleic acid binding domains, as well as methods for preparing and using them.

Background

Proteins can interact with nucleic acids, such as DNA and RNA, through a variety of physical forces, such as hydrogen bonding and electrostatic interactions. The interaction between a protein and nucleic acid can be dependent on the sequence of the nucleic acid, i.e., a sequence-dependent interaction. Alternatively, the interaction between a protein and nucleic acid can be independent on the sequence of the nucleic acid, i.e., a non-sequence dependent or non-specific interaction.

Nucleic acid binding proteins (NBPs) bind nucleic acid in a non-specific manner and have a wide range of applications. For example, nucleic acid binding proteins have been used in isolating nucleic acids from biological samples when coated on magnetic beads (see WO2009102632), preparing a population of fragmented polynucleotide sequences having a substantially uniform size (see US20090191563), or detecting the presence of DNA in a sample (see U.S. Pat. No. 4,963,658). When NBPs are attached covalently or non-covalently to a solid matrix, they provide an advantage in that immobilized NBPs are easier to manipulate even with the bound nucleic acid. However, in some instances, the bound nucleic acid can only be released from the protein by applying rather harsh conditions such as by heating to 95° C. for a certain amount of time for protein denaturation, or by protein digestion by a protease. In other cases, NBPs can only bind specific types of nucleic acids, for example, either single-stranded nucleic acids, or modified nucleic acids. Therefore, there exists a need for non-sequence specific nucleic acid binding proteins having a broader range of binding to different types of nucleic acids. Additionally, the nucleic acid should be easily released from the NBP without the need for protease digestion, thermal denaturation or other harsh extraction methods.

In some aspects, such nucleic acid binding domains of proteins may not form multimers and/or may be manipulated easily. Therefore, isolated nucleic acid binding domains that can interact with nucleic acids without requiring the full sequence of a naturally-occurring protein may have use in a wide range of applications.

SUMMARY

In accordance with the description, the present application demonstrates isolated nucleic acid binding domains that can be used to isolate nucleic acids. These domains may be coupled to solid matrices or surfaces. This isolation can have a number of uses, such as to facilitate downstream enzymatic or chemical reactions with the nucleic acid or for removal of nucleic acid from a sample. The present disclosure provides surface-immobilized isolated nucleic acid binding domains able to form and maintain stable complexes with nucleic acids without sequence specificity and under a broad range of conditions (such as temperature, ionic strength, and pH).

This application describes an isolated nucleic acid binding domain that comprises an amino acid sequence with at least 70%, 80%, 85%, 90%, 95%, 96%, 97%, 98%, or 99% identity to any of SEQ ID NOs: 1-24. Preferably, the domain comprises an amino acid sequence with at least 70%, 80%, 85%, 90%, 95%, 96%, 97%, 98%, or 99% identity to SEQ ID NO: 15, 10, 2, 9, 23 or 22. In some aspects, the domain comprises the amino acid sequence of any one of SEQ ID NOs: 1-24; preferably, the amino acid sequence comprises SEQ ID NO: 15, 10, 2, 9, 23 or 22.

The application also describes an isolated nucleic acid binding domain identified by an expectation value of less than or equal to e-05 in an alignment search for detecting sequence similarity using the amino acid sequence of SEQ ID NO: 2 or SEQ ID NO: 23. In some aspects, an isolated nucleic acid binding domain comprises an amino acid sequence with at least 30%, 35%, 40%, 45%, 50%, 55%, 60%, 65%, 70%, 75% or 80% identity to SEQ ID NO: 2 and is identifiable by an expectation value of less than or equal to e-05 in an alignment search for detecting sequence similarity using the amino acid sequence of SEQ ID NO: 2. In some aspects, an isolated nucleic acid binding domain that comprises an amino acid sequence with at least 30%, 35%, 40%, 45%, 50%, 55%, 60%, 65%, 70%, 75% or 80% identity to SEQ ID NO: 23 and is identifiable by an expectation value of less than or equal to e-05 in an alignment search for detecting sequence similarity using the amino acid sequence of SEQ ID NO: 23.

In some aspects, the amino acid sequence of an isolated nucleic acid binding domain comprises at least one motif with at least 90%, 95%, 96%, 97%, 98%, or 99% identity with $AX_4(L/M)X_4G(I/V)GX_6(I/V)X_3R$ (SEQ ID NO: 25) or with only 1, 2, or 3 amino acid differences from SEQ ID No: 25. In some aspects, such isolated nucleic acid binding domain comprises an amino acid sequence with at least 30%, 35%, 40%, 45%, 50%, 55%, 60%, 65%, 70%, 75% or 80% identity to SEQ ID NO: 2.

In some aspects, the amino acid sequence of an isolated nucleic acid binding domain comprises at least one motif with at least the amino acid sequence of the domain comprises at least one motif with at least 90%, 95%, 96%, 97%, 98%, or 99% identity with $NXAX_4(L/M)X_4G(I/V)GX_3AX_2(I/V)X_3RX_{7-11}LX_2VXGIG$ (SEQ ID No: 26) or with only 1, 2, or 3 amino acid differences from SEQ ID No: 26. In some aspects, such isolated nucleic acid binding domain comprises an amino acid sequence with at least 30%, 35%, 40%, 45%, 50%, 55%, 60%, 65%, 70%, 75% or 80% identity to SEQ ID NO: 2.

In some aspects, the amino acid sequence of the domain comprises a motif comprising any one of SEQ ID Nos: 25 or 26. In some aspects, the amino acid sequence of the domain comprises at least one amino acid mutation in a conserved amino acid position in SEQ ID NO: 25 or SEQ ID NO: 26 or within 2 amino acids from a conserved amino acid position in SEQ ID NO: 25 or SEQ ID NO: 26, and wherein the domain comprising at least one amino acid mutation is capable of releasing bound nucleic acid at lower temperature and/or in the presence of lower amount of salt compared to the same domain without a mutation.

In some aspects, said mutation is in the G(I/V)G sequence of SEQ ID NO: 25 or in the GIG sequence of SEQ ID NO: 26 or within 2 amino acids from any of said sequences.

In some aspects, the domain is non-sequence specific.

In some aspects, the isolated nucleic acid binding domain binds nucleic acid at temperature from 4° C. to 72° C., at a temperature from 25° C. to 65° C., at a temperature from 25° C. to 42° C., at a temperature from 25° C. to 37° C., or at a temperature from 18° C. to 25° C. In some aspects, the domain binds nucleic acid at 0 M to 2.5 M NaCl. In some aspects, the isolated nucleic acid binding domain binds nucleic acid in a solution with salt concentration from 50 to 1500 mM NaCl, in a solution with salt concentration from 50 to 500 mM NaCl, in a solution with salt concentration from 100 to 500 mM NaCl, or in a solution with salt concentration from 100 to 200 mM NaCl.

In some aspects, the isolated nucleic acid binding domain binds nucleic acid in a solution with salt concentration from 0 to 50 mM NaCl, from 0 to 20 mM NaCl, in a buffered solution, or in water.

In some aspects, the domain binds nucleic acid at a temperature of 4° C. or greater. In some aspects, the domain binds nucleic acid at a temperature of 25° C. or greater. In some aspects, the domain binds nucleic acid at a temperature of 37° C. or greater. In some aspects, the domain binds nucleic acid at a temperature of 42° C. or greater. In some aspects, the domain binds nucleic acid at a temperature of 65° C. or greater.

binding domain does not bind nucleic acid at a temperature of 65° C. or greater, at a temperature of 72° C. or greater, at a temperature of 80° C. or greater, at a temperature of 90° C. or greater, or at a temperature of 98° C. or greater. In some aspects, the isolated nucleic acid binding domain does not bind nucleic acid in a solution with salt concentration from 0 to 2.5 M NaCl, in a solution with salt concentration from 50 to 1500 mM NaCl, in a solution with salt concentration from 50 to 500 mM NaCl, in a solution with salt concentration from 100 to 500 mM NaCl, or in a solution with salt concentration from 100 to 200 mM NaCl.

In some aspects, the domain binds nucleic acid at 0 M to 2.5 M NaCl. In some aspects, the domain binds nucleic acid at 50 mM to 700 mM NaCl. In some aspects, the domain binds nucleic acid at 100 mM to 500 mM NaCl.

In some aspects, the isolated nucleic acid binding domain does not bind nucleic acid at a temperature from 25° C. to 65° C., at a temperature from 25° C. to 42° C., at a temperature 25° C. to 37° C., or at a temperature from 18° C. to 25° C. In some aspects, the isolated nucleic acid binding domain does not bind nucleic acid in a solution with salt concentration from 0 to 2.5 M NaCl, in a solution with salt concentration from 50 to 1500 mM NaCl, in a solution with salt concentration from 50 to 500 mM NaCl, in a solution with salt concentration from 100 to 500 mM NaCl, or in a solution with salt concentration from 100 to 200 mM NaCl. In some aspects, the isolated nucleic acid binding domain does not bind nucleic acid in a solution with salt concentration 0 to 50 mM NaCl, 0 to 20 mM NaCl, in a buffered solution, or in water.

In some aspects, the domain is tagged. In some aspects, the tag is a His-tag, AviTag (SEQ ID NO: 27), SNAP-tag, Strep-tag, T7-tag, FLAG-tag, S-tag, HA-tag, c-Myc tag, GST-tag, MBP-tag, CLIP-tag, ACP-tag or MCP-tag. In some aspects, the tag is fused to amino terminus of the domain. In some aspects, the tag is fused to carboxy terminus of the domain. In some aspects, the tag is used for purification of the domain. In some aspects, the tag facilitates binding of the domain to a solid matrix. In some aspects, the nucleic acid binding domain is chemically or enzymatically modified. In some aspects, the chemical modification is biotinylation. In some aspects, the chemical modification facilitates binding of the domain to a solid matrix.

This application also describes a nucleic acid encoding the isolated nucleic acid binding domain. In some aspects, the sequence is optimized for expression in bacteria, e.g. in *Escherichia coli*.

This application also describes a composition comprising an isolated nucleic acid binding domain immobilized to a solid matrix. In some aspects, the solid matrix is provided on a microchip or microcolumn. In some aspects, the solid matrix is magnetic particles, chemically modified agarose, dextran, polyacrylamide resin, silica gel, cellulose, glass, or a plastic surface. In some aspects, the magnetic particles are beads.

In some aspects, the isolated nucleic acid binding domain is immobilized to a solid matrix by covalent interactions, non-covalent interactions, passive adsorption, or entrapment.

In some aspects, the isolated nucleic acid binding domain is immobilized to the solid matrix by reaction of amine groups to N-hydroxysuccinimide (NHS), amine groups to carboxylic acid-, epoxy- or aldehyde-modified substrates, of thiols to maleimide-, disulfide-, pyridyl disulfide- or vinyl sulfone-modified substrates, of carboxylic acid groups to amine-modified substrates, of hydroxyl groups to epoxy-modified substrates, or via N,N'-dicyclohexyl carbodiimide-activated (DCC) carboxylic acid groups on amine-modified substrates.

In some aspects, the non-covalent interaction is between biotinylated isolated nucleic acid binding domain and a streptavidin-coated solid matrix. In some aspects, the non-covalent interaction is between streptavidin-tagged isolated nucleic acid binding domain and a biotinylated solid matrix.

In some aspects, the isolated nucleic acid binding domain of the composition is bound to nucleic acid.

This application also describes methods of identifying one or more candidate isolated nucleic acid binding domain using alignment search.

In some aspects, a method of identifying one or more candidate isolated nucleic acid binding domain comprises performing an alignment search for detecting sequence similarity using an amino acid sequence of any one of SEQ ID NOs: 1-24; reviewing results; and identifying one or more candidate isolated nucleic acid binding domain based on an expectation value of less than or equal to e-05. In some aspects, the amino acid sequence of SEQ ID NO: 2 or SEQ ID NO: 23 is used for performing an alignment search for detecting sequence similarity.

This application also describes a method of isolating nucleic acid from a sample comprising contacting one or more isolated nucleic acid binding domain with a sample comprising a nucleic acid under conditions suitable for binding, wherein the one or more isolated nucleic acid binding domain is bound to a solid matrix either before or after contacting it with a sample; and separating the sample from the solid matrix with the bound one or more isolated nucleic acid binding domain bound to nucleic acid.

This application also describes a method of isolating nucleic acid from a sample comprising providing a composition comprising one or more isolated nucleic acid binding domain immobilized to a solid matrix; combining the composition comprising the one or more isolated nucleic acid binding domain immobilized to a solid matrix with a sample comprising a nucleic acid under conditions suitable for binding; and separating the sample from the composition comprising the one or more isolated nucleic acid binding domain immobilized to a solid matrix bound to nucleic acid.

In some aspects, the conditions suitable for binding are incubation for less than or equal to 1 minute. In some aspects, the conditions suitable for binding are incubation for less than or equal to 5 minutes. In some aspects, the conditions suitable for binding are incubation for less than or equal to 10 minutes. In some aspects, the conditions suitable for binding are incubation for less than or equal to 60 minutes. In some aspects, the conditions suitable for binding are incubation for 60 minutes or more.

In some aspects, the solid matrix is magnetic beads. In some aspects, the sample comprises genomic DNA or cell-free DNA. In some aspects, the sample comprises blood, plasma, serum, urine, saliva, cell lysate, enzymatic reaction mixture, or a buffer. In some aspects, the sample comprises nucleic acids that have been run through an electrophoretic gel. In some aspects, the isolating of nucleic acids is performed after the sample exits an electrophoretic gel.

In some aspects, the nucleic acid is eluted from the one or more isolated nucleic acid binding domain before further steps. In some aspects, the elution is performed by heating to 65° C. or higher. In some aspects, the elution is performed by heating to 72° C. or higher. In some aspects, the elution is performed by heating to 80° C. or higher. In some aspects, the elution is performed by heating to 90° C. or higher. In some aspects, the elution is performed by heating to 98° C. or higher.

In some aspects, the nucleic acid is enzymatically or chemically modified without disrupting the binding of the nucleic acid to the isolated nucleic acid binding domain.

In some aspects, the enzymatic modification is performed by a DNA modification enzyme. In some aspects, the enzymatic modification is performed by a ligase, restriction enzyme, deoxyribonuclease, ribonuclease, polynucleotide kinase or polymerase. In some aspects, the enzymatic modification is ligation, phosphorylation, or dephosphorylation. In some aspects, the enzymatic modification is end blunting, tailing of ends, phosphorylation or dephosphorylation of nucleic acid ends, ligation of synthetic adapters to nucleic acid ends, or enzymatic fragmentation of nucleic acid. In some aspects, enzymatic modification is performed by a DNA modification enzyme immobilized to a solid matrix. In some aspects, the isolated nucleic acid binding domain and DNA modification enzyme are immobilized on the same solid matrix. In some aspects, the isolated nucleic acid binding domain and DNA modification enzyme are immobilized on at least two different solid matrices.

In some aspects, multiple steps of an enzyme modification or multiple enzymatic modifications to the nucleic acid are performed without disrupting the binding of the one or more nucleic acid to the isolated nucleic acid binding domain.

In some aspects, the nucleic acid is prepared for next generation sequencing by performing multiple steps of an enzyme modification or by performing multiple enzymatic modifications.

In some aspects, isolating nucleic acid from a sample is for depleting nucleic acid from a sample.

This application also describes a kit comprising one or more isolated nucleic acid binding domain and a suitable buffer for binding the one or more isolated nucleic acid binding domain with nucleic acid. In some aspects, one or more isolated nucleic acid binding domain is immobilized to a solid matrix. In some aspects, the kit further comprises a solid matrix not immobilized to the isolated nucleic acid binding domain. In some aspects, a solid matrix for immobilizing the isolated nucleic acid binding domain is provided separately from the one or more isolated nucleic acid binding domain. In some aspects, a kit further comprises an elution buffer for eluting nucleic acid from the one or more isolated nucleic acid binding domain.

Additional objects and advantages will be set forth in part in the description which follows, and in part will be obvious from the description, or may be learned by practice. The objects and advantages will be realized and attained by means of the elements and combinations particularly pointed out in the appended claims. It is to be understood that both the foregoing general description and the following detailed description are exemplary and explanatory only and are not restrictive of the claims. The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1 provides the amino acid sequences and the results of functional testing of several nucleic acid binding domains. ComEA1 is SEQ ID No: 1. ComEA2 is SEQ ID No: 2. ComEA3 is SEQ ID No: 3. ComEA4 is SEQ ID No: 4. dsDNA=double-stranded DNA; dsRNA=double-stranded RNA; ORF=open reading frame. ssDNA=single-stranded DNA; ssRNA=single-stranded RNA.

FIG. 4 shows the results of an analysis of 600 bp dsDNA NoLimits fragment capture efficiency depending on the amount of DNA used for binding. 500 ng, 1000 ng and 1500 ng DNA was incubated with 100 μg of streptavidin-coated magnetic beads (MB) with immobilized biotinylated nucleic acid (NA) binding domain (ComEA2) for 15 min in 25° C. "Bound" samples are those which bound to the MB, while "Unbound" samples are those from the supernatant. The DNA size marker was ZipRuler Express DNA Ladder 2 (Thermo Fisher Scientific, MA, USA).

FIGS. 8A-8B show electrophoresis (E-Gel) results. FIG. 8A shows E-Gel CloneWell II Agarose Gel where ZipRuler Express DNA Ladder was run. Magnetic beads with immobilized nucleic acid binding domain ComEA15 were added to different recovery wells (bottom well in the picture) at different times to bind a specific size of DNA fragment when it entered the recovery well. In FIG. 8A, beads can be seen in the recovery well in the bottom of lane 3. FIG. 8B shows results of binding DNA fragments of ZipRuler Express DNA Ladder 2 on ComEA15 coated magnetic beads in the E-Gel and elution of the fragments. Lane 1 shows ZipRuler Express DNA Ladder 2. Blocks of 200 bp (lanes 2-5), 400 bp (lanes 6-9), 700 bp (lanes 10-13), 1000 bp (lanes 14-17) and 1500 bp (lanes 18-21) denote the experiments where DNA Ladder fragments of different sizes were bound in the recovery wells. Lanes 6, 10, 14 and 18 denoted "Pre-binding" represent the contents of recovery well before loading the beads, where a portion of DNA fragments of smaller size that have crossed the recovery well remained. The light band at approximately 1500 bp in all E98 lanes corresponds to streptavidin, which was eluted from the magnetic beads under these conditions. E80=elution at 80° C. for 20 minutes; E98=elution with 0.1% SDS and at 98° C. for 10 minutes.

FIG. 9 shows results of binding and elution of GeneRuler DNA Ladder Mix on ComEA15 K55R coated magnetic beads under different elution conditions (65° C., 75° C., and 80° C.). The DNA size and amount marker was MassRuler DNA Ladder Mix (Thermo Fisher Scientific, MA, USA).

FIGS. 11A-11B shows results of binding and elution of GeneRuler 100 bp Plus DNA Ladder on DDE_Tnp1_assoc8 coated magnetic bead at different NaCl concentrations (50 mM, 100 mM, 200 mM, 300 mM, and 500 mM). FIG. 11A presents results at pH8.0. FIG. 11B presents results at pH 7.6.

FIG. 12 provides alignments of 15 ComEA domains (SEQ ID Nos: 1-15 for ComEA1-ComEA15, respectively). Dashes indicate where a particular sequence did not have an amino acid at a given position of the alignment; "*" (asterix)—the residues in that column are identical in all sequences in the alignment; ":" (colon) means that conserved substitutions have been observed; "." (period) means that semi-conserved substitutions are observed.

FIG. 14 shows results of binding and elution of phi6 dsRNA on DDE_Tnp1_assoc8 coated magnetic beads. The DNA size and amount marker was ZipRuler 2 (Thermo Fisher Scientific, MA, USA).

DESCRIPTION OF THE SEQUENCES

Figure 2:
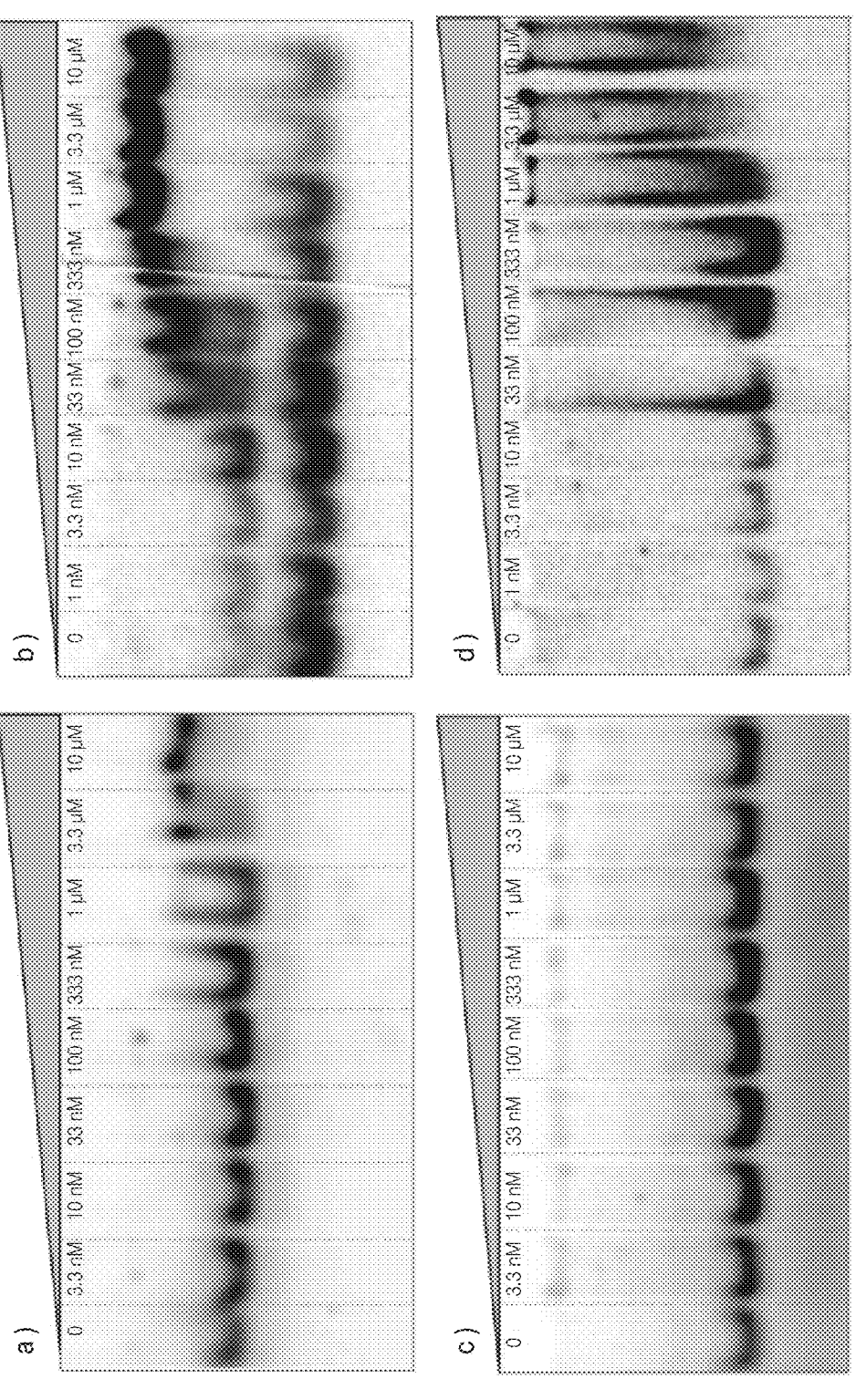
FIGS. 2A-2D show the results of electrophoretic mobility shift assay (EMSA) analysis of interactions between ComEA2 (SEQ ID No: 2) nucleic acid binding domain and double-stranded DNA in Tris-acetate buffer, pH 7.5 (FIG. 2A); double-stranded DNA in MES-His buffer, pH 6.0 (FIG. 2B); single-stranded DNA in Tris-acetate buffer, pH 7.5 (FIG. 2C); and single-stranded DNA in MES-His buffer, pH 6.0 (FIG. 2D). The numbers above the lanes indicate the concentration of ComEA2 in the substrate-domain complex formation reaction.
Figure 3:
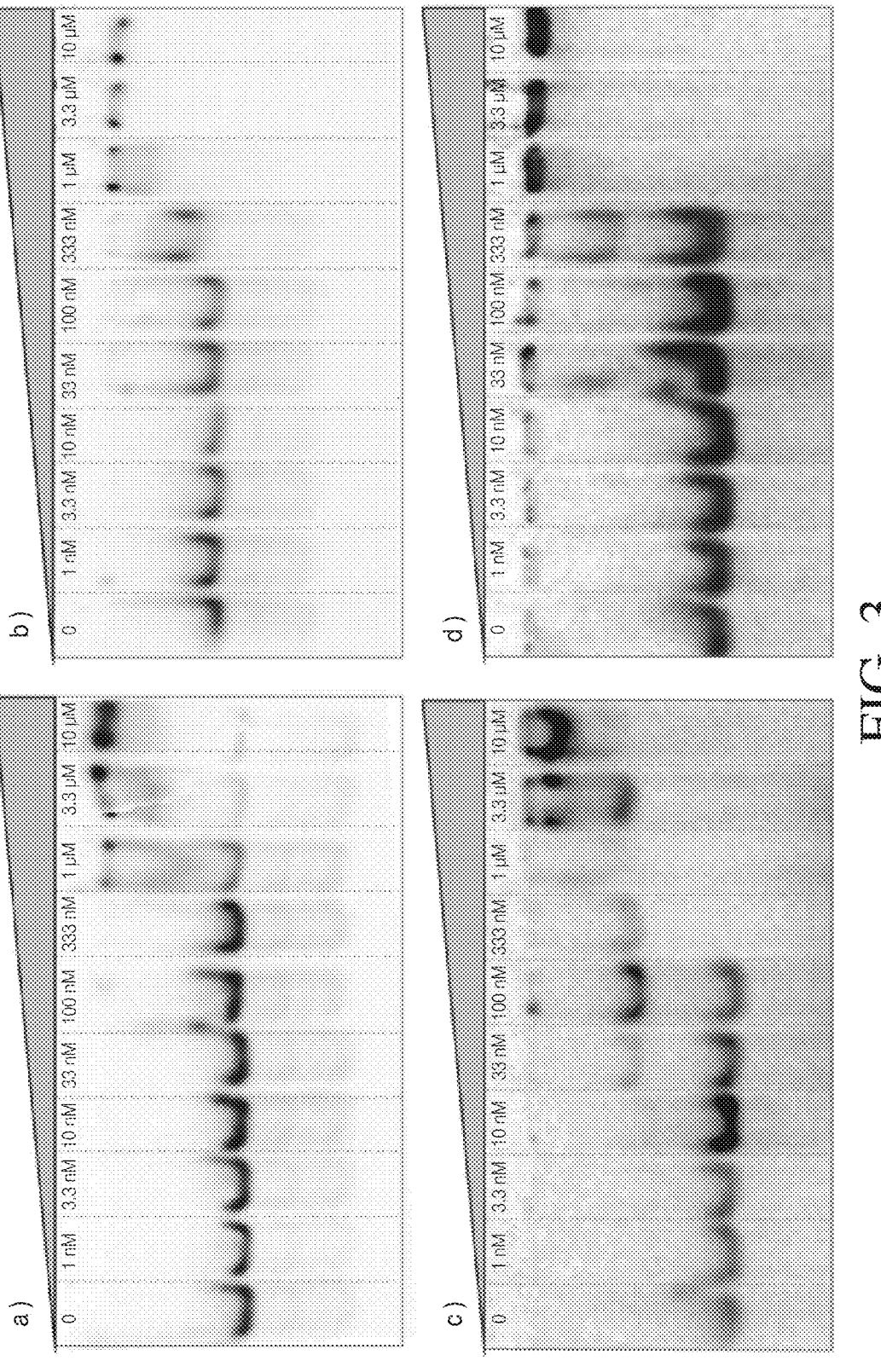
FIGS. 3A-3D show the results of EMSA analysis of interactions between ComEA2 (SEQ ID No: 2) nucleic acid binding domain and double-stranded RNA in Tris-acetate buffer, pH 7.5 (FIG. 3A); double-stranded RNA in MES-His buffer, pH 6.0 (FIG. 3B); single-stranded RNA in Tris-acetate buffer, pH 7.5 (FIG. 3C); and single-stranded RNA in MES-His buffer, pH 6.0 (FIG. 3D). The numbers above the lanes indicate the concentration of ComEA2 in the substrate-domain complex formation reaction.

Table 1 provides a listing of certain sequences referenced herein.

| Description | Sequences | SEQ ID NO |
|---|---|---|
| ComEA1 nucleic acid binding domain | GDGRIDLNTATADQLQTLPGIGPVLAQRIIDHPASIGGFTSVE QLHDVTGIGDRRFAELRDLVYVGGAP | 1 |
| ComEA2 nucleic acid binding domain | VVAFPVELNTASLEDLMSIPGIGPVKAQRIIDVRESHGGFSSV EELKNVSGIGEKTLEKISRYVTVEG | 2 |
| ComEA3 nucleic acid binding domain | PEPISLNRASLEELEALPGIGPTLARRIVEGRPYGKVEDLLRV KGIGPATLERLRPYVRP | 3 |
| ComEA4 nucleic acid binding domain | SSGGKINLNTADEAALQTLPGIGPTLARRIVEYRAKNGPFTSV EDLAKVPGIGPRRLEQLREYVCAP | 4 |
| ComEA5 nucleic acid binding domain | ELRVIELNAADSAQLVDIIGIGPVLALRIAKYRNRLGGFHSKE QLREIFGIDSLKYAEIKNQVRVDQ | 5 |
| ComEA6 nucleic acid binding domain | ELRVVELNAADSAQLVDIIGIGPVLAVRIAKYRDRLGGFHTKE QLQEVFGIDSLKYAEIKNQVRVEQ | 6 |
| ComEA7 nucleic acid binding domain | QLNKISFDEADSIVLQIVPGVGPATAGRIIKFRDAIGGMHTSE QLLDVYGMSPEVMERVFEYFEFTP | 7 |
| ComEA8 nucleic acid binding domain | SFNKITFSEATAIELQMVQGVGPFLSARIDDYRESLGGFHSPE QILEVYGVDAELAEKIYSVFAFES | 8 |
| ComEA9 nucleic acid binding domain | HLAIFDLNTADTTQLMQIRGIGRGISARIVAYRARLGGFVRAE QMAEIYSLRDAPDLIDSLRKYTFVKA | 9 |
| ComEA10 nucleic acid binding domain | SPKHLVDLNRATIGDLEQLPGIGPQTAERVVRFREHNGPYRSI DDLKKVGGIGERTLEKISPWVTV | 10 |
| ComEA11 nucleic acid binding domain | EKDDLLNINSADLSELQTLSGVGPSKAQSIISYREEFGPFKSI DQLLEVRGIGEKTIEEWKDKIKFQ | 11 |
| ComEA12 nucleic acid binding domain | INYTVKDINKATAIDLQVVSGIGEKISSRIVKFRDRLGGFVVN EQLQDVYGLDKEVLNRLLKQFKVI | 12 |
| ComEA13 nucleic acid binding domain | KSIDIYDLNTATEEDLQKIKGIGPAYSERIVKYRNLLGGFSDT TQLHEVYGLKPETISRLLEQFRIL | 13 |
| ComEA14 nucleic acid binding domain | GSTEMVNVNTADEQAMQNLPGIGPAKAKAIIQYRDEHGPFKSL DELTDVSGIGEKSLEKMKPNMSLQ | 14 |
| ComEA15 nucleic acid binding domain | ADSAQINLNTASLEELQTISGIGAKRAQDIIDYRDNNGGFSSV DDLKNVSGIGEKTLEKLKAEVTVD | 15 |
| DDE_Tnp1_assoc 1 | LVIAFVSVLCGSTSCAEMAAFGRAKESLFRNFLKLKHAIPSHD TFSEVFRIIDPKALDAAFSKVLADVT | 16 |
| DDE_Tnp1_assoc 2 | LFLAITAVISGCEGWEEIQDFGNDKLDWLRKYLPFSGGIPTDD TISRIFQLIDPKEFQKCFATWMKSC | 17 |
| DDE_Tnp1_assoc 3 | LFLTMVAVIGGCEGWEDIEDFGHCHLELLKKYGDFSAGIPVHD TIARIICKVDPEALQQAFISWMQAT | 18 |
| DDE_Tnp1_assoc 4 | MAFLARVDSLRGVERFARANPHLLPHLGLRNPPGHTILTLLLH RLDPKKLQEALLQVFPEVDLGG | 19 |
| DDE_Tnp1_assoc 5 | VALVLVAFVCRVDSLRGVARFAQANPFLCKPLGLRKAPGPSSI AQLIRRLDPQALGSALQQVFPELPLPA | 20 |
| DDE_Tnp1_assoc 6 | LGLILVAFLCRVDSLRGVARFARENPELLPLLGLRKPPGHYTV TTILHRLDPQDLQEALRSVFPEADLAA | 21 |
| DDE Tnp1_assoc 7 | MILAVMQGENSLRGIAQWMRLHWEEIAEPLNLWATKGAPSYGT LWNLLASLDPKELNQVLQGAEEGG | 22 |
| DDE_Tnp1_assoc 8 | LTLSLAAMLSGANDLRAVFRWGRRLPPEALFLLGLERAPCHAT YHYFFKALDVAATEAVLGAWVRGA | 23 |
| DDE_Tnp1_assoc 9 | LFIALLATLCGATACTDMALFARLKAYLWQDVLVLENGLPSHD TFSRVFRMLDPAAFEKAFQRFMKAFAQGA | 24 |

-continued

| Description | Sequences | SEQ ID NO |
|---|---|---|
| Artificial Motif 1<br>(X = any amino acid) | AX$_4$(L/M)X$_4$G(I/V)GX$_6$(I/V)X$_3$R | 25 |
| Artificial Motif 2<br>(X = any amino acid) | NXAX$_4$(L/M)X$_4$G(I/V)GX$_3$AX$_2$(I/V)X$_3$RX$_{7-11}$LX$_2$VXGIG | 26 |
| AviTag | GLNDIFEAQKIEWHE | 27 |
| ComEA1 nucleotide sequence from GenBank AAZ54864.1 entry, ComEA1 binding domain is coded by 859-1065 nt (underlined) of the sequence | ATGGCACGACACACTGCTCCTGAGCCCGCTGCCCCGGGAGCGC AGCAGCCGTCTCCCCTGCCGTCGTCTGAGGCCGCCTTGCCTGC CGAGTGGCGGGCAGCGGACGACGGGGACCCGACCCCACTGGAC TTCACTGTTCCTCCCCCGCCCTATGCCGTAGCCGACACGGTCC GCTCCCCGGTGCCCGTGCTTCCCGCGCCACGGCGTCCCCCGGC TCCCGAGGTGGGGAGGGACGAGGATGCGGCAGAGCGCCCTGCC CGGGCGGGCCGCGGTGCCCGTCCGGCCCCGCCCGCCGCACCTC AGCCGGACCGCGGCACGGGTCGGAACGACGGTTCGGCTCCCGC TCCCCCGCCCGGGTATGTGCGCATCCCGCCGCTCCCCGACCCG GCGGAGCGGCGGCTGCCTGCCCCGCTGGCGGCCCTTGTGGACC GCTGGAGGGGTGTCTCAGTGGAGCTGCGGCCCCGCGTGACCCT GTCCGGGGTGGCGGCGCTCGCCCTCGTGTGCCTGCTGGCCGCG GGGGTCACCGGCTGGTTCATGCTCAACGCCCGTCCCGCGTCCG CGCCCGCGCCGCCGCAGGAGGCCGTCCCGTCCGGTCCTCATCC GTCCCCGGCGGCGGAAGCGAGTCCTGCCGGCACGGTCGTGGTC CACGTGGGCGGTGACGTGGTCTCCCCGGGGATCGTGACCCTGC CCGCCGGGTCCCGGGTGGCCGATGCTCTCGACGCGGCGGGCGG CCCGCGCCCGGATGCGGATCTAGGGTTCCTGAACCTGGCCCGT CCCCTCGTCGACGGCGAGCAGATCCTCGTTGGGGGTCACCCCGT CGCCCATGGCCGGGGAAGGCGAGGGTCCGGGCCTGCCCGCC<u>GG GGACGGGCGGATCGACCTCAACACCGCTACCGCCGACCAGTTG CAGACCCTGCCGGGAATCGGCCCGGTGCTGGCCCAGCGCATCA TCGACCACCGCGCGTCCATCGGCGGTTTCACCTCGGTGGAGCA GCTCCACGACGTCACCGGTATCGGGGACCGCCGGTTCGCGGAG CTGCGCGACCTGGTCTACGTCGGCGGTGCCCCGTGA</u> | 28 |
| ComEA2 nucleotide sequence from GenBank KUK22668.1 entry, ComEA2 binding domain is coded by 85-288 nt (underlined) of the sequence | GTGGCACTTGTTTTCTTCATATTGCTTGGAATTGTTATGGAAC GAGAAACGAAAACAGAAGAGGACACAACATCCTCTCAGAAG<u>GT TGTCGCCTTTCCTGTGGAGCTGAACACCGCTTCTCTGGAAGAC TTGATGTCGATTCCAGGGATCGGGCCTGTGAAAGCCCAGAGGA TCATCGATTACAGAGAGTCACATGGTGGATTTTCGAGCGTGGA AGAATTGAAGAACGTCTCTGGAATCGGAGAAAAAACCCTGGAG AAGATTTCCAGATATGTGACCGTCGAAGGAGTTGAACAACATA</u> TCAAAAGAGAAGTCACAAAACTGAACGTGAACACAGCTTCGGT TGAAGAACTCGAAACCCTTCCCTACATAGGTGAGGTAAAGGCA AAAGCCATTGTCGAGTACCGAGAGAAAAACGGTCCCTTTCGTT CTCCCGAAGATCTTCTGGACGTGCCTGGAATAGGTGAAAAGAC GCTGGAGAAAATAAGAGGAAAAATCACATTTTGA | 29 |
| ComEA3 nucleotide sequence from GenBank AEV17292.1 entry ComEA3 binding domain is coded by 127-306 nt (underlined) of the sequence | GTGGTCCTTGGCTACCTCCTGGCGGTAGCCCTCCTGGGCCTCC TGGCCCTGTGGCCGAAGGTGGCCCCGGGACCCGGCCCCGTGGC AGTGGAGGTCTGGGCAGAGCCCCGCTTCACCCCTCCACCCCCG <u>GAGCCCATCAGCCTGAACCGGGCCAGCCTGGAGGAGCTGGAGG CCCTGCCCGGTATCGGCCCCACCCTGGCGCGGAGGGATCGTGGA GGGCCGGCCTTACGGGAAGGTGGAGGACCTCCTGCGGGTGAAG GGGATCGGGCCGGCCACCCTGGAGCGGCTCCGACCCTACGTGC GCCCCTGA</u> | 30 |
| ComEA4 nucleotide sequence from GenBank ACX5280.1entry, ComEA4 binding domain is coded by 382-582 nt (underlined) of the sequence | TTGACCTTCGGGAAGCGAGAATATTTCGTGGCCCTGGCGCTGG GGATAGCTTTGCTGTTAGGCTTAGGGGTCAGGGACCTCTTTTC CCGCCCGGTTGAGGTAACGCCTGCTCCTCCGGCAGTGGAGCGG GAGGAAAAGATAAGAGGTACGGTGTGGGTGCACGTGGCAGGGG AAGTTAGTCATCCCGGAGTTTACGAACTCCCTGCCGGCAGCCG GGTAAAGGATGCCCTGGAAAAGGCTGGCCTTCTTCCAACGGCC GACCCCCACGCCCTGAACTTGGCGCAGGTCTTGGTGGACGGGC AGAAGATCGTAGTCCCTCCCAAGCTTGCAGAGGGAAAAGAAGG CGAGGTAAATAACCCCTTTGCTACTCGGGTTTCTGCTTCCTCC <u>GGGGGGAAGATCAACCTCAATACCGCCGATGAGGCCGCGCTTC AGACCCTGCCTGGGATAGGCCCTACGCTGGCGCGCCGCATTGT GGAGTACCGGGCCAAGAACGGTCCGTTTACCTCGGTGGAGGAC CTGGCTAAGGTGCCAGGCATCGGTCCCAGGCGCCTGGAGCAGT TGCGCGAGTACGTGTGCGCCCCTTGA</u> | 31 |
| ComEA5 nucleotide sequence from GenBank WP_069660874.1entry, ComEA5 binding domain is coded by 607-807 | TTGAAAAAGTGGTTAAATGCATTTTTTGGTTTCACAAAGAAGG AGCAAAACGGATTATTGGTTCTATGTATTCTTATTTGTTTAGT TGCTTTATTCCCCTGGGTGTATGCTGCAGTCCAGTCGCCTGTT GTTTATCATTTTTCGGACTATTCCAAATTTGCTGAAACAGTCA GTGAGTCTTCCACAGGCAATCCAAATTCATCGTATCCAAATTC | 32 |

-continued

| Description | Sequences | SEQ ID NO |
|---|---|---|
| nt (underlined) of the sequence | GCCAGGGTATAATCATTCTTCCTATAGTAATTCTCACTCTTAT ACCCATTCTGGGGTTACAGGCCCCTCCGGATCGCGTATAAAAG CACAGTATTTTCTTTTTAACCCCAATCAGCTAGCCACAGCAGA CTGGAAGAAACTGGGGCTGTCCGAAAAACAGGTCCAGGTCATT CATCATTATGAAGATAAGGGTGGAAGCTTTCGGAAGAAGGAAG ATCTGAAGAAGATCTACTCCCTTTCAGCTTATGAATATGATCA TCTCGAGCCGTATATACGGATTCCCGAAACCTCATTTCCGAAC GCCTCTTTTAAAAAGAATGATTATACAGGATCAAAAACTAATC CTGATTACCATTTCGTCAAGAAAAGTTATCCCCAGTATGTAAA ACGTGAACTGAGGGTTATTGAATTAAATGCTGCAGACTCTGCT CAGTTAGTTGATATAATAGGGATCGGACCAGTGCTGGCTCTTC GCATTGCTAAATATAGAAACAGGTTAGGTGGATTCCATTCCAA GGAGCAGCTGCGGGAGATTTTCGGTATTGACTCCCTGAAGTAT GCTGAAATAAAGAACCAGGTACGCGTGGACCAAGTATCCCTGC ATCAGATCAATATCAATACGGCTACATTTGAGGACTTAAAAAA GATTCCCTATTTCAGTTACAAACAAATCAATGCCTTAATTCAG TATAAGAAGCAGCATGGAGAATATCATTCAATAGACGATTTGA GGCAGATAAGCATTCTTAACTCTGAAATTTTGCTTAAAATTGC ACCTTATTTAATTTTCCAA | |
| ComEA6 nucleotide sequence from GenBank EOR92537.1entry, ComEA6 binding domain is coded by 247-447 nt (underlined) of the sequence | TTGTCCGAAAAGCAGATCCAGGTCATTCATCACTATGAGGACA AGGGTGGAAGCTTTCGCAAGAAGGAAGATCTGCAAAAAATCTA TTCCATTTCTACTTTTGAATATGCTCATCTCGAACCCTATATC CGGATTCCCGAAACTTCTTATAATAATACCTCTTTTAAAAGGA ATGATTATGCCGGATCAAAAGCTAATCCTGATTACCATTATGT CAAGAAAAATTATCCTCCGAATGCAAAACGAGAACTGAGGGTT GTTGAATTAAATGCTGCACACTCTGCTCAATTAGTTGATATAA TAGGCATCGGACCAGTGCTGGCCGTTCGAATAGCCAAATACCG AGACCGTCTAGGTGGATTTCATACCAAAGAGCAACTTCAGGAA GTATTTGGGATCGACTCCCTGAAGTATGCAGAAATAAAGAACC AGGTACGCGTGGAACAGGGATCCCTGCATCAGCTCAATATCAA TACGGCTACATTTGAGGACTTAAAAAAGTTTCCCTATTTTAGT TATAAGCAAATAAATGCCTTAATTCAATATAAGAAGCAGCATG GAGAATATCATTCAATAGATGATTTGAGGCAGATTAGCATTCT TAACTCTGAAATTTTGCTTAAAATTGCACCTTATTTAATTTTC CAATGA | 33 |
| ComEA7 nucleotide sequence from GenBank AFL86171.1entry, ComEA7 binding domain is coded by 259-459 nt (underlined) of the sequence | ATGATTCGAAAAATGAAGTTTTTTCTCAAAAATTACCTTGGGT TTAGCAATAGAGAATCTAGAGGTTTTATCTTGTTAGTTCCTGC CTTATTACTTTTGTATGCAGTACCTGTGATTTACAATAACATT TTGGCGAAAAGGAATCAAATAGATTATGAAATCTATTTGGAGA AGATGGATAGTTTAGAAAGCGCTGGTTGGCATAAGGTCGAAAC TCAATATTTCATGAGTCAGGATACTTCAAAAAGAAGACAACCT CAGCTTAACAAAATATCTTTTGACGAAGCAGATTCGATTGTTT TACAAATAGTTCCCGGTGTTGGTCCGGCTACAGCAGGTAGGAT TATCAAATTCCGTGATGCAATTGGAGGAATGCATACTTCTGAG CAACTTCTTGATGTTTATGGAATGAGTCCTGAAGTCATGGAAA GAGTGTTTGAGTATTTTGAATTCACTCCGGGAATAAAAACTAA AATCAATATCAATACAGCAGATGTCCCAACTTTGGCGGCACAT CCTTATATTAATTATGGTAGTGCCAAAGTGATTGTAGCTTATA GAGATCAGCATGGAGCTTACACTACCGCTGATGATTTATTAAA AGTTAGAATCTTCAGCCAAGAGTGGATTGATAGAATCAGACCC TATTTAACTTATTAA | 34 |
| ComEA8 nucleotide sequence from GenBank AKP51876.1entry, ComEA8 binding domain is coded by 274-474 nt (underlined) of the sequence | TTGGGTTTTACCCGTAGGGAAATGCGGGGTTTCGTTTTTGTAA TCCCTATACTTTGCCTGCTATACGCTGGGCCATTTTTTATAGA ACGTATCACCACTCTTCTGATCAAGCTACTTATTTGGCTTAC ATTGCTGAAAACAATGAATTGCTAAGCCAAAAGGTTCCTTCTC GGATAGATTCTAGTCAGAAAAACCAAAAGCCAAGCCAGGAAAC AAAGAGGGAAGAAAAGAAAAGCAGCTCTTCATCATCACTAAAG AAACCTAGCAAGCCAAGTTTCAATAAAATAACTTTTTCTGAAG CTACTGCCATTGAATTGCAAATGGTACAAGGTGTAGGACCTTT TCTTTCTGCGCGAATTGATGATTACAGAGAAAGTTTAGGCGGT TTTCACAGTCCGGAGCAAATTCTGGAAGTTTATGGGGTAGATG CTGAACTCGCCGAGAAAATTTACTCTGTATTTGCTTTTGAATC CCATATAAGCCGTCAATTAAATATCAATTCAGCAGATTTTAAA CAATTGATAAAGCACCCTTATATAGACTATGGGGCCACTAAGG TGATTTTGGCTTATAGGAAACAACATGGGCCATACAAATCAGC AGAAGAGTTGTTGAATATTAAAATTTTCAATGAAGACTGGGTA AATAGAGTTTCCCCTTACCTGACTTTTTGA | 35 |
| ComEA9 nucleotide sequence from GenBank OUJ75377.1entry, ComEA9 binding domain is coded by 622-828 | ATGAAAGTCTAACAAGCTAGGCCTTCTACGCCGCCAGCTTCTT TTTTTAGGAAGAGCCAGACAGCGCTCCGGCGCTACTTCGGCTT TTCGCGTCGCGAGACGTCCGGTTTTGTGGTGCTGGTGGCTTTG CTACTGTTGTGGTTGTTTCTGCCGGCCCTGTTGCGTCCCGCCT TGCCCCAGTACGACCCAGCCGCCGATCAGCGCGCCAGTTAGAGCA | 36 |

| Description | Sequences | SEQ ID NO |
|---|---|---|
| nt (underlined) of the sequence | GGTAGCAACGGAGCTAGCGGTCCAGCGCCAGCCTCGGGCCTTC GCCGACCGGCGCTACCCGCGCCGCGGCTATGCCCCGCGCGTAC CCGTGCCACAGGTCCCCCTTGCTCCTTTCGACCCAAATAGTCT CACGCCGCTTGAGTGGGAAGCCCGCGGCTTGCCGCACTTCGTG GCCGAACGCATTGTGCACTTCCGCGACGTACTAGGCGGGTTCA AAGCCAAAGAGCAGATCCGACGCACCTATGGGCTTCCAGATTC GGTGTACGCGCGGCTAGCTCCGTACATGCTGCTGCCCGATCAG CTTCCGCCGCGCACGGCTCGCTCCTATCCTAGCTCCGAGCGCT TCGCTGGTAAGTTTACGGAACGTCCTAGCTTTCCCACCAGCAA GTTTGCCCGCAAGCCCGCGCACTTGGCTATTTTCGACTTGAAC ACCGCCGATACAACACAGCTCATGCAGATCCGGGGCATCGGGC GCGGCATTTCGGCGCGTATTGTAGCCTACCGGGCGCGACTCGG TGGTTTCGTACGAGCCGAGCAGATGGCCGAAATCTATAGCTTG CGCGACGCACCCGATCTCATAGACAGCCTGCGCAAATACACCT TCGTGAAGCTAGCTTTGCCCCAGCCTCACTCGACGTGAATAC GGCTAGCTTCGACGAGCTACAAAGTCATCCGTACATGGGCAAG CGATTGGCACGCGTAGTGGTGGCTTTCCGCCAGCAGCACGGCC CCTTCAAGCAACCCGACGACCTGCGCCAGATCCGTATTCTGGA CGAGGCCACGTTCGAAAAGCTTAAGCCATATTTACGCTTTTGA | |
| ComEA10 nucleotide sequence from GenBank CCQ94388.1entry, ComEA10 binding domain is coded by 466-663 nt (underlined) of the sequence | ATGGAACGGTTGATCCGGTTTGTAACTGAGCGGCGAAAACTTT TCATCGTCATCGTACTTGCGGCCGTGGGCTTTATTTATTTGCT GATCGCCAAAACAAAGGACGAGCAGAAATTTCTCCTTCCTCCC TATGACCAGGAGAGTGGGGGGACCGTGACGGAGACCGGTACGG GAAGTCCAGATTTCCCTAAGGAAAAAGGCGGGGAGGGACTTCC TGCGGTTCAATGGATTGAAGTAGATGTGAAAGGAGCGGTGAGA AATCCGGGAGTGTATAAAATCGAGGAGAATGCTCGGGTCCATG ATCTCCTGGAGAAGGCAGGGGGGACGGTAGAAGAGGCGGATCT TTCTCAGGTCAATTTGGCCGCTTTTTTTAAAAGACGGACAAGTG GTATATATCCCTCGGATAGGGGAACAAGGTGTGGGATGGAATC CCCCAATGGCCTCAACTTCGTCAAAGGGAGGAGATGCCGGAAA AACTCTAATCAATCTTAATTCCGCTACGCTGGAAGAGCTGGAT CAGCTCCCAGGCATTGGCCCCTCGAAGGCGGAGTCGATCCTTC GCTATCGAGAGGAACACGGGCCGTTTAAGGATGTGAATGAGCT AACCAACGTTTCCGGAATCGGTGAGAAGACACTGGAGAAACTT CTTCCCTATATCACTGTCCGGTAG | 37 |
| ComEA11 nucleotide sequence from GenBank OOE13681.1entry, ComEA11 binding domain is coded by 424-624 nt (underlined) of the sequence | ATGATTCAGCTGAAAAAGCATATAAACTTGGTGCTCGGAGCCA CTTTATTACTTTTAATTTTGATTGGAGTGTTCATTTACAAAAA TATAAACAGTCAGCCTGATTTGGTGATTTCACCCGAACAAATG CCTATGATAAAAGATGAAACTGAAACGATTGACTCTGAAACTG AAAAAAATGAGGAGGAATCTATTGTATCAGGTCGAATTATGGT CGATGTTCAGGGAAGTGTTAATCGACCTGGTGTGTATGAAATG AATAATGGTGATCGTGTGATTGACGTGATTAAAAAAAGCGGGTG GTTTTTTAGAAGAAGCAGAAGCTCGATCAGTAAATCAGGCTGA GAAAATTATTGATGAAATGATTATATATGTTGCAGCTAAAGGG GAAGAGGTTCATCCTTTATCTTCTAATAAGGGAAATGAAAAAG ATGATTTGTTAAATATTAATTCTGCTGATCTATCTGAACTTCA GACCCTTAGCGGTGTCGGCCCCTCTAAAGCTCAAAGTATTATT TCCTACCGTGAGGAATTTGGACCGTTCAAATCAATTGATCAGC TTTTAGAAGTTCGTGGAATTGGTGAGAAAACGATTGAAGAATG GAAAGATAAAATTAAATTCCAATAA | 38 |
| ComEA12 nucleotide sequence from GenBank EWH12801.1 entry, ComEA12 binding domain is coded by 455-666 nt (underlined) of the sequence | ATGAAGAATTTTAAATCCCACTTTCAGTTTGATAAAGAACAGA AAAGTGGGATTTTCTTTTTGTTATTATTAATTGTAATTTTTCA GGCTATATATTATTTGGTTTCAAATGGTGTATTTACTTCTAAA AATAATAGTTTACTACATAATAAAGAGCTTCAGGTTGCAATAG ATTCACTAAAAAATCAATCTGTAAAAAAGAATACATATAAAAT GTACCCTTTTAATCCTAATTATATAACAGATTATAAAGGTTAT AAATTGGGGATGTCTATTAAAGAAATAGATAGGTTGCATTTG TATAGGGAAACGGGTAAATATGTTAACTCTATAGAGGAGTTTA AGAAAGTAACAAATGTCTCAGATTCATTATTAAAAGCAATATC TCCATATTTTAAATTTCCAGATTGGAAAGCTTCAAAATTTGAC AAAAAAATAACTGTTGCAAATAAGTCTTCTAAAAACATCAATT ATACAGTTAAGGATATTAATAATGCCACTGCAATAGACTTGCA GGTGGTAAGTGGAATTGGAGAAAAAAATATCTTCCAGAATAGTT AAATTTAGAGATAGGCTAGGTGGTTTTGTGGTTAATGAGCAGT TGCAAGATGTTTATGGTTTAGATAAAGAAGTTTTAAATCGGTT GTTAAAGCAATTTAAGGTAATTGGTAAGCCTGTTATAAGTAAA ATTAATATAAACGAGGCTAGTGCTTATGAAATTTCTAAGTTGG TATATATAAAATATGATGTTGCTAAGGCTATTGTGGCTTACAG AGAAGAAATGGAAGATTTACATCTTTTAACGATTTGGTAAAT ATTGAGGGTTTTACTGTGAATAAGATTGATAGAATTAAGTTAT ATTTGAGCATTGATTAA | 39 |

-continued

| Description | Sequences | SEQ ID NO |
|---|---|---|
| ComEA13 nucleotide sequence from GenBank SNS57745.1 entry, ComEA13 binding domain is coded by 313-513 nt (underlined) of the sequence | ATGTTGAAATTTTTAATCAACGCCATTTCTCGTGCAATCGGCT TCAGCAGAACTGAAGCACAAGGATCATTAATCCTTATTCTATT GATCTCAATCACTATTTTTCTTTACAACACAAGGGTTGCCAGC ATCAAGCATCAAGTCGAAATCAGATCAGATAGTTCCGCGATAG AATGGATTAAGTCTGTCCATGCTTCTTAGCAGATAAAAGAAAA CAAACCCAAGTTTGAAAAAAGCATATTCCTACCGAAGAAAACT ACTTATGAAAATAGAAAGACAGATAAATGAAGTAGTGTCAACC CAAACAAGAACAAATCAATTGACATCTATGATCTCAATACTGC <u>AACTGAAGAAGATTTACAGAAAATTAAAGGCATTGGACCAGCC TACTCAGAACGCATAGTCAAATACAGAAACTTACTAGGAGGCT TTTCAGACACTACGCAGCTACATGAAGTATACGGATTGAAGCC CGAAACCATTTCAAGATTATTAGAGCAGTTCAGGATTTTAAGC</u> CCAGTGAACCAGTTCAATATTAATTCCGATTCAATAAAGCATT TAGCAAAGCATCCTTATGTTTCATATGACCTGGCTTGGGTAAT TATCAATTACAGAAGAGAGCATGGTGACATTATGAGTCCCCAA GAGTTAAAAAAAAATAAAAGCACTGGACGACAGTACTTTCATAA GATTAAAGCCATATTTGGAATAG | 40 |
| ComEA14 nucleotide sequence from GenBank SFG08046.1 entry, ComEA14 binding domain is coded by 442-642 nt (underlined) of the sequence | TTGAGAGAGCGCTTGAATAAATTTAGAGTATGGGTGATTATCG GCGTAGTCGCGGCCCTTCTCATCTTTTGGCTGCTTTATCAGCA TCAAAACAATCTCAAGCGATCAGCGGAAGTGCGGAAAACCGAT CAGCTCTTTTCGAAGCAACAGAAAAGTAACGGTATATCCGAAA GCCCAATCAGCAAGCAAAATAGTTTACCTTCAGAACTTGTTAT CGATGTAAAAGGGGCCGTACGAAATCCGGGCATTTATCATGCG CAAGCATCTGACCGTGTCATTGATGGTATTAAGCAGGCTGGCG GTTTCAGCAAAAAAGCGGATCGCGACAAAATCAATCTGGCCCA GAAATTGGCCGATGAGATGGTAATTTATGTGCCGGAGAAAGGT GAAGAGATGCAGGTGTCTGCCGGCGGGGCACCGGGAGCGGTGT CTGGGCAGCAGGGGAGCACAGAGATGGTGAATGTAAATACGGC <u>GGATGAACAAGCGATGCAGAATCTGCCCGGAATCGGTCCTGCA AAAGCGAAGGCGATTATTCAGTATCGAGATGAGCATGGACCTT TCAATAGCCTGGATGAGTTGACAGATGTTTCAGGAATTGGTGA</u> GAAGTCTTTGGAGAAGATGAAACCAAATATGTCACTCCAGTAA | 41 |
| ComEA15 nucleotide sequence from GenBank EFW89502.1 entry, ComEA15 binding domain is coded by 478-678 nt (underlined) of the sequence | ATGATTGAAGAGATGAAAGAAAAAATTTTAGAGCATAAAACTG TGGCATCAGTTTTGGGGACAGTACTTATTATGCTAGTGATGTT TTTTGCTTGGTCTAGTATGGAAAGCCACAAAGCTGAAGTGCAA AATGATTTACCAGCATTGAGCACTAGCTTTTCAACAAGCAGTG TGGAAATATCTCAGCCAAAAACAGCGAAGTCTGCTTCAAAATC TGAATCAGATAAGATTTTCGTTGATATAAAAGGTGCCGTGAGA AAAGAAGGCGTTTATGAATTGATATCAGGTAGTCGTGTGACAG ATGTGGTCAAATTAGCTGGCGGTTTTACAGATGATGCGGATAA GAAATCTGTTAATTTAGCTGAAAAAGTAGCGGACGAATCAGTG ATTTACGTGGCAAGAGTTGGTGAAGAGGTCACACCAGAAAGTA CCACGTCTCAAATCAAAAATACAGCAGCTAGTGGAGCACTGCA <u>GGATGCAGACTCAGCACAAATCAATCTTAATACTGCGTCTTTA GAAGAACTTCAGACGATTTCTGGCATCGGCGCCAAACGGGCTC AAGACATCATCGATTATCGTGATAACAACGGTGGATTTTCGTC AGTTGATGATTTGAAAAATGTGTCAGGTATTGGTGAGAAGACC</u> TTAGAAAAACTAAAAGCTGAGGTGACAGTTGATTAA | 42 |
| DDE_Tnp1_assoc_1 nucleotide sequence from GenBank AGI72635.1 entry, DDE_Tnp1_assoc_1 binding domain is coded by 112-318 nt (underlined) of the sequence | ATGGGTGGTTGTTCTCATGCGGGTGCTCATCGCCATGCATATT TTCTATCCGCCTTCGACGAAGTTCCTGATCCGCGCGCCAGTAA CGTGCGCCACGACCTTGGTGAACTG<u>CTCGTTATCGCCTTCGTG TCGGTCTTATGTGGATCGACCTCCTGCGCCGAGATGGCCGCAT TTGGCCGTGCAAAAGAGAGCCTTTTCAGGAACTTCCTGAAACT CAAGGATGCCATTCCATCGCATGATACCTTCTCGGAGGTCTTC CGGATCATCGACCCGAAGGCACTCGATGCGGCCTTCAGTAAGG TACTTGCCGATGTGACCAAGCTCCTCAAAGACGGTGATATCAT</u> CGCGATTGACGGCAAAGCGTTACGGGGTGCGCGCGACCCGGGC GAAAGCGCACGGACCCGCATGATGGTCTCAGCCTATGCCTCGC GGCTGCGCCTGACGTTGGCGACAGTACCTGCCGACCGAGGCAC AGAACTCAGCGCGGCCATAGAGGCGCTTGAGTTGATCGATCTG CGGGGCAAGGTGGTCACCGGTGATGCATTACATTGCAACCGCC GCACGGTTGCCGCAATCAACGCAGGCGGCGGTGATTGGTGCCT CGCCCTCAAGGGTAACCAGGAATCCCTGTTGTCTGACGCCCGT GGATGTTTCAGCAAGGGGCACAAAAGCGATCCAACAGCCGTTA CGGAAAATACCGGCCATGGAAGAAAAGAAACCCGTAAGGCGGT CGTGGTATCGGCTAAGGCATTGGCAGAATACCACGAATTCCCT GGCCTCAAGGGGTTCGGTCGCATCGAGGCGACGAGAGAGATGG GCGGAAAGGTGACCTCAGAGACCCGCTACTTCGCGCTGTCTTG GGTTCCCACACCTGAGGTGCTGTTGGCCGCTGTCCGCGACCAT | 43 |

-continued

| Description | Sequences | SEQ ID NO |
|---|---|---|
| | TGGGCCATCGAAAATGCCCTTCATTGGCAGTTGGATGTGTCTT TCCGCGAGGACGCCGCACGCAATCGGAAAGACAACGGTCCCGG CAACATCGCCGTTCTACGTCGCCGCGCACTCGACGTCCTCCGG CGTGACACATCCAAGGGCTCTCTCTCCATAAAAATCAAACGTG CAGGCTGGGACACCACCTTCTTACGCAGCATTCTCAGTGACTT GGCAACAACATGA | |
| DDE_Tnp1_assoc 2 nucleotide sequence from GenBank ABM03799.1 entry, DDE_Tnp1_assoc 2 binding domain is coded by 88-291 nt (underlined) of the sequence | ATGTCCCAAATAACCTTGATAAACCAGCTCTCAATCATCCGTG ATACCCGACAACCGAGGAAAGTGCATCAGAATTTAGTTGATGT TTTATTTTTGGCAATTACAGCCGTCATATCGGGCTGTGAGGGT TGGGAAGAAATACAAGATTTCGGCAACGATAAGTTAGATTGGC TGAGAAAGTATTTACCATTTTCAGGCGGAATACCTACGGACGA CACAATTTCTCGTATTTTTCAGTTGATTGACCCAAAAGAATTT CAAAAGTGCTTTGCTACTTGGATGAAAAGTTGCTGTGAAATGA GTCATGGAGATGTCATTGTTATTGATGGAAAAACATTAAGAGG TTCATTTAATAAGAAAGATAAATCAGATACTATTCATATGGTT AGTGCTTTTGCAGCCGCTAATTCGGTTGTGTTAGGGCAAGTTA AGACAAATGCTAAGTCTAATGAAATTACAGCGATTCCTAAGTT ATTAGATTTATTGGATGTACGTGGATGCCTCGTAACTATTGAT GCAATGGGATGCCAAACTAAAATAGCTAAAAAAATCGTAGATA AAGGTGGTGATTATCTTTTTCCTGTTAAAGGTAACCAAGAACG ATTACAAACAGCATTAGACGGTATATTTTCAATTGGCCGATTA GAGTTACCAGAAACAGAAGTCTATACGACTAAAAAAAAGGCAG GGTAA | 44 |
| DDE_Tnp1_assoc 3 nucleotide sequence from GenBank AQS3972.1 entry, DDE_Tnp1_assoc 3 binding domain is coded by 88-291 nt (underlined) of the sequence | ATGAGCCTTCTTACTCTTACTAAGTACTTTGAAATTATTGAAG ATCATCGTCAAGCCACTAAAGTTACTTATCCCTTGTTCGATGT ATTGTTTTTAACCATGGTAGCGGTTATTGGGGGCTGCGAGGGT TGGGAAGATATTGAAGATTTTGGCCATTGTGACTTAGAGTTAC TCAAAAAGTACGGGCATTTTAGCGCAGGGATCCCAGTCCATGA CACCATTGCTAGAATTATTTGCAAAGTCGACCCAGAAGCCCTG CAACAAGCGTTTATCTCATGGATGCAGGCAACCGAGCAACTGT CTCAAGGTCAAGTTATTGCCATTGATGGCAAGACTTTGCGTGG CTCTTATAATAGAGATGATCGTCAATCCGCCATTCATATGGTG AATGCTTTCTCTGTCGCCAATGGTGTCGTGATGGGACAACTTA AAACAGATTCGAAGTCCAATGAGATCACTGCTATTCCTGAATT ATTAGCCCTATTAGATATTCAAGGAGCATTGGTAACCATCGAT GCTATGGGGACTCAAGCCAATATTGCACATACCATCATAGACA AGGGAGCAGACTTCCTGTTAGCAGTCAAAGGCAATCAAAATTC TTTACATCAGCTAGTAAAAGAAACCTTCGCAGATCAGCTTGAT TATGCTGAAAAATATCACTCAAATTGAGGCGCAGCATGGCAGGA AAGAATTTAGGG7ATACCAAACTATTGAGGCACCTAAGGAGCT GATTGACGCCAAATGGCGAACAATACAAACCTTTGGAAAAGTA ATTACCTATCGAATAGGCCTTGTTTCCTAA | 45 |
| DDE_Tnp1_assoc 4 nucleotide sequence from GenBank ETN87911.1 entry, DDE_Tnp1_assoc 4 binding domain is coded by 81-285 nt (underlined) of the sequence | ATGACCCTACGCGAGGCCTTGTCCCAAGTCCCCGACCCCAGGG CCCGCAACCGGCGGTATCCCTTGTGGGGCTTGTTGGCCCTCAT CTTGGTGGCCTTTCTCGCCCGCGTCAACTCCCTGCGCGGCGTG GAACGTTTCGCCCGGGCCAACCCTCACCTCTTGCCCCACCTGG GCCTGCGCAACCCCCCGGGCCACACCATCCTCACCCTCCTCCT TCACCGTCTGGACCCAAAGAAGCTCCAGGAGGCCCTCCTCCAG GTCTTCCCCGAGGTGGACCTGGGAGGGGTCCTGGTGGTGGACG GGAAGCACCTCCGGGGAAGCGGCAAGGGGAAGAGCCCCCAGGT CAGGCTCGTGGAGGTCCTGGCCCTGCACCTCAAGACCACCCTG GCCCAGGCCCGGGTGGAGGGGAGGGAGGACCAAGCGCTTCTGG AGCTCCTGGACCGCCTGGGGGCGGAGGGACTCAAAGGGAAGGT AGTGGTGGGGGACGCGGGGTACCTGTACCCGGAGGTGGCGGGG AAGGTGGTGGAAAAAGGGGGGCATACCTCTTCGTCCTGA | 46 |
| DDE_Tnp1_assoc 5 nucleotide sequence from GenBank KIQ53990.1 entry, DDE_Tnp1_assoc 5 binding domain is coded by 76-285 nt (underlined) of the sequence | ATGAACTTACGCGAAGCCTTAGCCTCATTGGACGATCCACGCT ACCAGAACCGGCGCTATCCGCTGTGGGGGGTGGTGGCATTGGT GCTGGTGGCCTTTGTGTGCCGGGTGGACTCCCTGCGGGGTGTG GCCCGCTTTGCCCAAGCCAATCCCTTCCTGTGTAAGCCCCTGG GCTTGCGCAAGGCCCCAGGACGCAGCTCAATCGCCCAGCTCAT CCGCCGCTTGGACCCGCAAGCGCTGGGTTCAGCCCTGCAACAG GTCTTTCCCGAACTCCCCCTTCCCGCCTCTTTCCCTACCTCTA CCGCTACTACCTCTGCCCTGGTCGCGGATGGCAAGGTCTTGCG GGGGAGTGCTAAAGGCGAGAGCCCGGTGGTGCGGGTGGTGGAG CTGTGGTGTGAGCAAGCCCGCCACAGCCTGGCCCAGGCCCAAG TCGGTGGGCGGGAGGATGAGGCCTTGCTGGGTCTGCTGGAGCG CATGGGGCTGGAGGGTTTAGCCGGTCGGGTGGTGGTGGCCGAC GCGGGCTTCCTCTACCCCCGGGTGGCCGAAGCCATCCGGGCTA AGGGGGGGATTACCTGCTGA | 47 |
| DDE_Tnp1_assoc 6 nucleotide sequence | ATGAAGCTCAAAGAGGCCTTGACCAAGATCCCCGACCCCCGCG CCCAAAACCGGGAGTACCCCCTCTGGGGACTCCTGGGCCTCAT | 48 |

-continued

| Description | Sequences | SEQ ID NO |
|---|---|---|
| from GenBank KGQ22827.2 entry, DDE_Tnp1_assoc 6 binding domain is coded by 76-285 nt (underlined) of the sequence | CCTGGTGGCCTTCCTTTGCCGCGTAGACTCCCTTCGCGGTGTC<br>GCCCGCTTCGCCCGCGAAAACCCTGAGCTTCTCCCCCTCCTGG<br>GCCTGCGTAAGCCCCCAGGCCACTACACCGTGACCACCATCCT<br>GCACCGCCTGCACCCTCAGGACCTTCAGGAGGCTTTGCGCTCC<br>GTCTTCCCGGAAGCCGATCTCGCAGCGGTCCTCGTCGCCGACG<br>GGAAGGTCCTGAGGAACAGCCGCAAGGGGAACGCTCCCCAGGT<br>CAAGCTGGTGGAGGTGCTCGCCCTTCACCTGCACACCACCCTG<br>GCCCAGGCCCGGGCAGAGGGGAGGGAGAGCGAGGCCCTTCTGG<br>AGCTCCTCGGGCGCCTTGGGGCCGAGGGGCTTGCGGGAAGGCT<br>GGTGGTGGGGGACGCGGGCTACCTGTACCCGAAGGTCGCCCGG<br>AAGGTGGTGGAAAAAGGGGGGACTACCTCTTCGTCCTGA | |
| DDE_Tnp1_assoc 7 nucleotide sequence from GenBank OUC09230.1 entry, DDE_Tnp1_assoc 7 binding domain is coded by 1-201 nt (underlined) of the sequence | ATGATTTTAGCGGTCATGCAGGGGGAGAATAGTCTACGGGGCA<br>TTGCGCAATGGATGCGGCTACACTGGGAGGAAATTGCGGAACC<br>CTTGAATCTCTGGGCGACCAAAGGAGCGCCCTCCTACGGGATCC<br>TTATGGAATCTGCTGGCCAGCCTGGACCCCAAGGAGCTCAACC<br>AGGTTCTGCAGGGGGCAGAGGAAGGGGGAGGTTATACGCTGGA<br>TGGCAAACATTTGCGTGGGAGCAAACGCCAGAGCCAAGCAGCC<br>CTGCAGGTGGTAACCCTAGCGGGTGCCAGGTACGGCCAGATCC<br>TGGCCCAACAGGAAGTGGAGGCGGGCAATGAGCTGGCGGCAGC<br>CTTGCGGTTGTTACAGGAGGTGCCTGTGGCGGGCAAGCTGGTG<br>AGCATGGATGCGGGCCTTTTGCAGCGGGAGACGGTGGCAACCG<br>TGGCCCAAAAAGGGGGGCCTACATGGGGTTCGTCAAGGGCAAC<br>CATGGGGCTCTCTATGCGCTTATAG | 49 |
| DDE_Tnp1_assoc 8 nucleotide sequence from GenBank BAQ49359.1 entry, DDE_Tnp1_assoc 8 binding domain is coded by 127-327 nt (underlined) of the sequence | GTGATGATCCTGGAGGTCGGCGTGTCCGAAGCACTGGAGGTCG<br>GTCCTGCCAGCCTGTGGGAACACCTGGCTGCCATCCCGGATCG<br>GCGCGGCCGCAAAGGGCGGCAGTACGGCCTGCCCGCCATCCTG<br>ACCCGTCTCTCGCCGCCATGCTGTCGGGGGCCAACGATCTGC<br>GCGCCGTGTTCCGGTGGGGCCGACGGCTGCCGCCCGAGGCGCT<br>ATTCCTGCTCGGCCTGGAGCGGGCGCCCTGCCACGCCACGTAC<br>CATTACTTCTTCAAGGCCCTCGACGTGGCGGCGACCGAGGCGG<br>TGCTGGGGGCCTGGGTGCGCGGTGCGGCCGAACCGGATCAGGG<br>CCTGGGTCACGTGGCGCTCGATGGCAAACGGCTGCGCGGCTCG<br>GCTGGCGCGGACCACGACGGCAGCGGCGGCGCGCATCTGGTGG<br>CGGCCTTCGCCATCAGATTGGGCGGGGTGATCGGCCAGTTGCA<br>GGTGGCACCCGACGCCAACGAGATCACGGCGGCCCTGACACTG<br>CTCAAAGGGCTGCCGCTGCACGGCGCCCTCGTCACCGGCGACG<br>CGATGTTCTGCCAGCGGGCGATCTGCCAGGGCCTGCGCGACCA<br>GCACGGGGACTATCTGTTTGCCGTCAAAGCCAACCAGCCCGAG<br>TTGATGGCTGATCTGGCTCTCGCCTTCGGCGACGCCTTTCCCC<br>CCGGCGCTGCTCAAGGCGCTCAAGACGAGCGGCGGCGTCCGCC<br>CATCCGCTGA | 50 |
| DDE_Tnp1_assoc 9 nucleotide sequence from GenBank ABD87624.1 entry, DDE_Tnp1_assoc 9 binding domain is coded by 91-306 nt (underlined) of the sequence | ATGGAGCAGCCGATGGATCGATTTGCGGAGTGCTTCGAAGACC<br>TGCCCGACCCGCGGGCGGGGAATGCGTTGCACGATCTGACCGA<br>GATCTTGTTCATTGCCCTGATGGCGACGCTGTGCGGGGCGACC<br>AGTTGCACCGAGATGGCGCTGTTTGCCGGATGAAGGCCTATC<br>TTTGGCGGGATGTGCTGGTCCTGAAGAACGGCCTTCCGAGCCA<br>CGACACGTTCAGTCGGGTGTTCCGCATGCTGGACCCGGAGGCG<br>TTCGAGAAGGCGTTCCAACGCTTCATGAAAGCCTTTGCCAAAG<br>GCGCCAAGATCAAGCCGCCGAAAGGGGTGATCGCCCTCGACGG<br>CAAGGCGCTGCGGCGCGGCTACGAAAGCGGCAGAAGCCACATG<br>CCGCCCGTGATGGTGACGGCCTGGGCGGCGCAGACCCGCATGG<br>CGCTGGCCAATGTGCAGGCCCCGAACAACAACGAAGCCGCCGG<br>TGCCTTGCAACTGATCGAACTTCTGCAGCTCAAAGGCTGCGTC<br>GTGACGGCCGATGCGCTGGATTGCCATCGTGGCATGGCCGAAG<br>CGATCAAGGCCCGGGCGGCGATTATGTGCTGGCCGTGAAGGA<br>CAACCAGCCAGCGCTGATGCGGGATGCGAAGGCGGCAATCCGC<br>GCCGCCACGCGCCAGGGCAAGCCATCGACGATCACCGTCGATG<br>CCGGTCATGGACGCAAGGAAAAGCGCCGTGCTGTCGTCGCCGC<br>TGTCCCGCAGATGGCGCAAGACCACGACTTTGCCGGGCTCAAA<br>GCGGTGGCCAGGATCACCAGCAAGCGCGGCACCGACAAGACCG<br>TCGAGCGTTACTTTCTGATGAGCCAGGCCTATCCCCCCAAAGA<br>CGTCCTGCGCATCGTCCGGACCCACTGGACCATCGAAAACAGC<br>CTGCATTGGCCGCTCGACGTCGTGCTCGACGAGGACTTGGCGC<br>GCAATCGCAAGGACAACGCCCCCGCCAACCTCGCCGTGCTCAG<br>ACGCCTGGCCCTCAACGTCGCAAGGGCACATCCAGACAACACC<br>ACATCGCTGCGTGGAAAGCTGAAACGTGCAGGATGGAACGATA<br>CGTTCCTCTTCGAACTCATCCAACACATGCGATAG | 51 |
| GI: 503303602\|194-253 | SGKVNVNSAGKKLLMALSDRITPTLADSIIEARPIRKLQDLLD IPGFTRELYFEIRPIIT | 52 |
| GI: 15606502\|180-241 | SKGKVNINTAPLLVLYSLDRDIDMELAKRIADYRKEKPFKQLK DLLMVEGMTLDILYRIQNF | 53 |

| Description | Sequences | SEQ ID NO |
|---|---|---|
| GI: 502729464\|183-245 | SSGKININTANSYILMALDPRIDQALASKIIERRNREPFKKVE DLLLVDGFTFDILYAIKNLV | 54 |
| GI: 502756584\|179-241 | SSGKINVNTAPLYVLMALDDRIDEDLARRIIERRDKEPFRRVE DLLLVEGFTLDILYSVRDLV | 55 |
| GI: 288932121\|477-530 | LDVNKAKLYQLESIPGIGKTTAAKIISAKPFRSLKELKDLIGE EKFKILLPYIS | 56 |
| GI: 289596582\|111-163 | INVCPLEELLSTSLIGKKLAIRIMENRPYESMEELRKVRGIGE KRLSRLQARF | 57 |
| GI: 327400296\|474-526 | EILDVNRASLQQLEAIPGIGKATAAKIVANRPFRNVEEIASLV ENFDEIKDFF | 58 |
| GI: 284162061\|486-537 | LNPNTAKLYQLEAVPGIGKALAGKIIANRPYSSLDELRDVLGD VFDRVKHFF | 59 |
| GI: 490183434\|495-532 | INSMSLEELTAIPGIGSALARKIILNRPFRSWEDLKKV | 60 |
| GI: 15644349\|495-532 | INSMSLEELTAIPGIGSALARKIILNRPFRSWEDLKKV | 61 |
| GI: 502660280\|495-543 | INSMSLEELTAIPGIGNALAKKIILNRPFRSWEDLKKVVPAET VNFLRK | 62 |
| GI: 501268013\|495-532 | INSMSLEELTAIPGIGNALARKIILNRPFRSWEDLKKV | 63 |
| GI: 289596960\|482-522 | PLNVNSASFSTLKSIPGMGSKKAAEIIRKRPFKNMKSLQEI | 64 |
| GI: 503302539\|507-546 | PLNVNEASVKLLSFIPGISRKTASDIVLRRPFKSKEELLK | 65 |
| GI: 240103390\|525-579 | VPINVNRESPKVLQLIPGIGKKTATRILAKRPFRSREEFFEVV DPGVREVLKDLV | 66 |
| GI: 390960450\|525-580 | IPVDINRESPKLLQYLPGIGKKTAVKILSKRPFKNKDEFFSVV GEDKREMLGGIIR | 67 |
| GI: 83589893\|1129-1198 | ERIDLQKADASRFLVEPGKLLPPLAALPGVGRAAAEAIVRARG ERPFTSVEDLQYRSRVSKTVIEALEKH | 68 |
| GI: 760032306\|1406-1449 | LPGLGDSAAQAIVEARAQGPFHSKEDLKNRARLNKAVMELLEG H | 69 |
| GI: 501435520\|39-97 | NDLKIDINTADIITLQRIPYIGEKTAELIIKDRKIRGGYTDIN QLKWYKNFDKIKPYIK | 70 |
| GI: 501542092\|303-361 | PQFFPIEINKATYEQLLRIPGIGPISAKKIIKARKEQKIRDIK DLKKLGIQVERCKNYI | 71 |
| GI: 752795678\|309-345 | PQFFPVDVNRASYRELLRVPGIGPTIARRILEARKEG | 72 |
| GI: 752619530\|477-541 | VNYVGVNLNTASEHLLKYISGLNARMARNIVEYRKQVGLFKKR EDLLKVKGIGNKAFEQAAGFCR | 73 |
| GI: 504063068\|476-540 | VNLVGVNLNTASAALLQYISGITPKLAENIVKYREEWGFFKER KELLKYKGFGPKAFEQAAGFLR | 74 |
| GI: 75278743\|458-522 | VNMVGVNLNTASAKLLEYVSGITPSLAKKIVKYREKHGKFIER NQLLNIEGLGEKTFEQGAGFLR | 75 |
| GI: 501003427\|456-520 | VNQLGIDLNSASSKLLEHVAGITPSLAKKIVNFRKKIGKFTER KQLLEIEGLGQKTYTQCAGFLR | 76 |
| GI: 499609813\|492-556 | VNAVGVDVNTASVPLLSRVSGITASLAQNIVAYRDANGPFRTR AQLREVPRLGPKAFEQCAGFLR | 77 |
| GI: 49951040\|485-549 | VNAVGVDLNTASPSLLQYVAGIKASVARAIVEYREKHGKFRSR RELLKVSGLGPKAFEQGAGFLR | 78 |
| GI: 489614004\|480-544 | VNSVGVDLNTASPSLLSYISGINSVIAKNIVEYRETNGKFKRR EELKKVKKLGDKTFEQCAGFLR | 79 |
| GI: 503553382\|477-541 | VNSVGVDLNTASVSLLKYVAGINGTIAKNIVEYRNTVGKFRNR NELKKVKRLGEGTFTQCAGFLR | 80 |

-continued

| Description | Sequences | SEQ ID NO |
|---|---|---|
| GI: 503063630\|477-541 | VNSVGVDLNTASVSLLKYVSGINASIAKNIVEYRNEVGQFRNR NELKNVKRLGDATFTQCAGFLR | 81 |
| GI: 501226561\|477-541 | VNSVGVDLNTASVSLLKYVSGINAAIAKNIVEYRNQIGKFTNR EQLKNVKRLGDTTFTQCAGFLR | 82 |
| GI: 502914941\|477-541 | VNSVGVDLNTASVSLLKYVSGINTAIAKNIVEYRNQIGKFTSR EQLKNVKRLGEATFTQCAGFLR | 83 |
| GI: 5022759661\|477-541 | VNSVGVDLNTASVSLLKYVSGINTVIAKNIVEYRNQIGKFTSR EQLKNVKRLGEATFTQCAGFLR | 84 |
| GI: 502778332\|41-100 | KIAPVHINTATLAQLETLPGIGPKLAQEIIKHRPYKNAHDLQS KVKGISPSLWKKIAPKV | 85 |
| GI: 506219682\|128-192 | SSGGKINLNTADEAALQTLPGIGPTLARRIVEYRAKNGPFTSV EDLAKVPGIGPRRLEQLPEYVC | 86 |
| GI: 752787889\|141-201 | RIDLNTATADQLQTLPGIGPVLAQRIIDHRASIGGFTSVEQLH DVTGIGDRRFAELPDLVY | 87 |
| GI: 752790358\|493-552 | RVNLNTATAAELETLPGVGPKLAAEIIRAREQKPFNSLADLDA VPGVGPKLLEPLRDRVT | 88 |
| GI: 22299882\|505-564 | RVNLNTATAAELETLPGVGSKLAAEIIRAREHKPFQSLADLDA VPGVGPKLLERLRDRVT | 89 |
| GI: 502780313\|58-115 | QKVNLNTASQAEIESLPGIGPALAQRIIEGRPYRTLEDLERVK GIGPKLLERLRPLVT | 90 |
| GI: 753950367\|129-188 | PSRVKVSLNRATLEELEALPGIGPTKARRIMEYRPYLRVEDLL RVPGIGEKTLERLRPYV | 91 |
| GI: 504329537\|46-101 | ISLNRASLEELEALPGIGPTLARRIVEGRPYGKVEDLLRVKGI GPATLERLRPYVR | 92 |
| GI: 502258539\|50-262 | PIDLNTATVEILQLLPGIGETRAKAIVTFRESNGGFSSTEELL QVKGIGNSTYEKLKDLVTITNAAKSKAENTRDTRLDLNTASKV DLTSLPGIGEVKAAEIVKYREEHGGFKAIDELINVKGIGRATL DKIRNLVRVGSVSTNVPDKSENSGKINVNTATLQELVALPGIG PVLAERIIDYREHNGKFHKPEDLLKVSGIGIKTLSKFREMI | 93 |
| GI: 755152313\|102-162 | RIDINRASAAELEALPGIGPALAQRIVADREVNGPFRRPQDLS RVTGIGEKTLARLLPYIT | 94 |
| GI: 503040608\|149-209 | RININTAGLEELDKLPGIGPALAQRIIDYRNQHGPFKSVEELK NVSGIGEKKFEELKDLVK | 95 |
| GI: 83589434\|160-222 | GGKVNINTAGLAELDSLPGIGPTLAQRILDYRTQKGPFRTIED LQNVSGIGAKKFADLKDLIT | 96 |
| GI: 489614667\|234-294 | KININTATVEELDSLPGIGPAIAAKIVAYREQNGKFKSIEDIM NVSGIGQSKFNNIKDFIT | 97 |
| GI: 217967490\|122-186 | SKSDKVNINTASKEELESLPGIGPTLAQRIIEYREENGPFGSA EDLLNVKGIGEKKLERIRDQIT | 98 |
| GI: 501543178\|120-183 | KKGKVNINTASKEELESLPGIGPTLAQRIIEYREENGVFTSAE DLLNVKGIGEKKLEKIKDQIT | 99 |
| GI: 503055614\|155-217 | EGKININTATKEELKTLDRIGDKLAERIIEYRQNHGPFKSIEE IKNVNGIGEKIFESIKDFIT | 100 |
| GI: 503808183\|155-217 | EGKININTATKEELKTLDRIGDKLAERIIEYRQKHGPFKSIEE IKNVNGIGEKIFESIKDSIT | 101 |
| GI: 503197882\|155-217 | EGKININTATKEELKTLDRIGDKLAERIIEYRQKHGPFKSIEE IKNVNGIGEKIFESIKDSIT | 102 |
| GI: 503168696\|155-217 | EGKININTATKEELKTLDRIGDKLAERIIEYPQKHGFKSIEE IKNVNGIGEKIFESIKPSIT | 103 |

-continued

| Description | Sequences | SEQ ID NO |
|---|---|---|
| GI: 503177334\|155-217 | EGKININTATKEELKTLDRIGDKLAERIIEYRQKHGPFKSIEE<br>IKNVNGIGEKIFESIKDSIT | 104 |
| GI: 506388026\|157-217 | KININTATKEELKTLNRIGDKLAERIIEYRQKHGPFKSIEEIK<br>NVNGIGEKIFESIKDSIT | 105 |
| GI: 503195740\|157-217 | KININTATKEELKTLNRIGDKLAERIIEYPQKHGPFKSIEEIK<br>NVNGIGEKIFESIKDSIT | 106 |
| GI: 503589690\|158-217 | VNINTADQKELETLPGIGPSTAQRIIQYRETNGPFKVPEDIKN<br>VSGIGDKRFEQLKDYIT | 107 |
| GI: 503554242\|143-203 | KININTATKEELDTLPGIGEVTAQRIIDFREQHGNFQRIEDIM<br>NVSRIGPKLFEQIKDKIT | 108 |
| GI: 503062661\|143-203 | KININKATKEELDTLPGIGEVTAQRIIDFREQHGNFQKIEDIM<br>NVSRIGPKLFEQIKDKIT | 109 |
| GI: 499334810\|132-194 | AKKVNINTATKEELQTLPGIGPVTAERIIEFRETKGPFKKIED<br>IMNVPRIGPKMFEQIKPKIT | 110 |
| GI: 501225752\|139-199 | KININTATREELQTLPGIGPVTAERIIEFRESKGPFKKIEDIV<br>NVSRIGPKMFEQIKDKIT | 111 |
| GI: 503828681\|139-202 | KSEKININTATKEELQTLPGIGPVTAERIIEFRESKGSFKKIE<br>DIMNVPRIGPKMFEQIKDKIT | 112 |
| GI: 502759964\|136-199 | KSEKININTATKEELETLPGIGPVTAERIIEFRENKGFFKKIE<br>DIMNVPRIGPKMFEQIKDKIT | 113 |
| GI: 502915162\|136-199 | KSEKININTATKEELETLPGIGPVTAERIIEFRENKGFFKKIE<br>DIMNVPPIGPKMFEQIKDKIT | 114 |
| GI: 753908752\|6-65 | EIKIDLYTASETQLTKIPGIGPKTAKKIIQYREKYGFSSVKDL<br>MKIKGIGEKTYEKIRKY | 115 |
| GI: 760031704\|172-231 | VNINTAGQAELETVPGIGPALAPAIITYRTEHGPFQSVDDLIN<br>VSGIGSKTLEKIRPYVT | 116 |
| GI: 501268304\|42-180 | VVAFPVELNTASLEDLMSIPGIGPVKAQRIIDYRESHGGFSSV<br>EELKNVSGIGEKTLEKISRYVTVEGVEQHIKREVTKLNVNTAS<br>VEELETLPYIGEVKAKAIVEYREKNGPFRSPEDLLDVPGIGEK<br>TLEKIPGKIT | 117 |
| GI: 506400261\|42-180 | VTSFPIDLNSASVEDLMSIPGIGPVKAQRIVEYRRIRGKFSTV<br>EELTNVSGIGEKTLEKISKYVTVEGVEQPFRSEVTKLNVNTAS<br>LEELETLPYIGEAKARAIIEYREEHGPFSSPEDLLNVPGIGEK<br>TLERIRGKIT | 118 |
| GI: 501004996\|42-182 | AEQIIDINSATFEQLVSLPGIGPTKAKSIINYREKVGEFLSID<br>DLLNVSGIGPSTLKKIKPFIKIKTANVITNSPSGSEDVKININ<br>NASVEELMKLPGIGKVKAQEIIEFRKKFGNVQSFEDLLKVKGI<br>GKKTLEKIKPFI | 119 |
| GI: 503697337\|46-182 | EFPIDINKASYEELLVLPGIGPTKARAIVEYRQKYGPFESLPD<br>LAKVSGIGKKTVERLANFVKIEGTVFVKMEEKRRINVNIATLE<br>QLCELPGIGEVKASQIIKYRQENGPFKKPEDLLKVPGIGPKTL<br>EKIKDFIT | 120 |
| GI: 503673264\|26-85 | INLNVAGQEELANLPGVGPKIAAAIVEYREKYGPFKSVDELLE<br>IKGIGPKKLEKIRPLVT | 121 |
| GI: 752791330\|1-60 | KIDINQATVEELEKLPGIGPKIAKNIVEYREKNGPFRSIEELL<br>KVKGIGPKKLEQIKKYL | 122 |
| GI: 490204927\|51-189 | SQIIDLNKADLEQLMSLPGIGTVKAKAIISYRQAHGNFNSIDD<br>LINVTGIGPSTLEKIPDYVTVSKTNEVQINMNNELKKININKA<br>DEKQLEKLPGIGPTKAKRIIEYREKNGKFNSLNELLNVNGIGP<br>KTLEKIKNYL | 123 |
| Motif in ComEA15 K55R mutant; amino acid residues of motif of SEQ ID NO; 26 are underlined, K55R mutation is in bold | <u>NTAS</u>LEEL<u>QTI</u>S<u>GIGA</u>K<u>R</u>A<u>QDI</u>IDY<u>R</u>DNNGGFSSVDDL<u>KNVSG</u><br><u>IG</u>ER | 124 |

-continued

| Description | Sequences | SEQ ID NO |
|---|---|---|
| Motif in ComEA15 I52F mutant; amino acid residues of motif of SEQ ID NO; 26 are underlined, I52F mutation is in bold | NTASLEELQTISGIGAKRAQDDIIDYRDNNGGFSSVDDLKNVSG FGEK | 125 |
| Motif in ComEA9 A31N mutant; amino acid residues of motif of SEQ ID NO: 25 are underlined, A31N mutation is in bold | ADTTQLMQIRGIGRGISARIVAYR | 126 |
| Motif in ComEA15 mutant; amino acid residues of motif of SEQ ID NO: 26 are underlined, one or more mutation positions {corresponding to positions 10, 16, 20, 23, 27, 41 , 45, 51, 52, 54, 55, or 56 of SEQ ID NO: 15) are in bold | NTASLEELQTISGIGAKRAQDIIDYRDNNGFSSVDDLKNVSG IGEKT | 127 |
| Motif in ComEA9 mutant; amino acid residues of motif of SEQ ID NO: 25 are underlined, one or more mutation positions (corresponding to positions 19, 23, 27, 31, 33, 38, 39, 40, 41, or 42 of SEQ ID NO: 9) are in bold | ADTTQLMQIRGIGRGISARIVAYRARLGGFVRA | 128 |
| Motif in ComEA2 mutant; amino acid residues of motif of SEQ ID NO: 26 are underlined, one or more mutation positions (corresponding to positions 11, 16, 21, 26, 28, 29, 30, 32, 33, 40, 45, 46, 49, 51, 52, 58 or 59 of SEQ ID NO: 2) are in bold | NTASLEDLMSIPGIGPVKAQRIIDYRESHGGFSSVEELKNVSG IGEKTLEK | 129 |
| DNase I with an N-terminal tag (5-10 - Histag sequence; 11-30 - linker sequence; 31-45 - Avitag; 46-305 - sequence of bovine DNase I) | MAGSHHHHHHGMASMTGGQQMGRSGDDDDKGLNDIFEAQKIEW HELKIAAFNIRTFGETKMSNATLASYIVRIVRRYDIVLIQEVR DSHLVAVGKLLDYLNQDDPNTYHYVVSEPLGRNSYKERYLFLF RPNKVSVLDTYQYDDGCESCGNDSFSREPAVVKFSSHSTKVKE FAIVALHSAPSDAVAEINSLYDVYLDVQQKWHLNDVMLMGDFN ADCSYVTSSQWSSIRLRTSSTFQWLIPDSADTTATSTNCAYDR IVVAGSLLQSSVVPGSAAPFDFQAAYGLSNEMALAISDHYPVE VTLT | 130 |

DETAILED DESCRIPTION

This application describes isolated nucleic acid binding domains that may be used in a variety of methods. In some embodiments, these domains bind to nucleic acids in a non-sequence specific manner.

I. Definitions

"Non-specific" or "non-sequence specific," as used herein, refers to binding of a nucleic acid binding domain to a nucleic acid that occurs without the need for a specific nucleic acid sequence.

A "motif" as used herein, refers to an amino acid sequence shared by related domains. As used in this application, a motif is a sequence shared by non-sequence specific nucleic acid binding domains.

A "nucleic acid binding domain," as used herein, refers to a unit of a protein, comprising a polypeptide subsequence or a complete polypeptide sequence where that unit has a nucleic acid binding function.

An "isolated nucleic acid binding domain," as used herein, refers to a nucleic acid binding domain that binds nucleic acid without the need for other amino acids that it is expressed together with in naturally expressed proteins. For example, the isolated nucleic acid binding domain may be a domain that is normally comprised within a larger protein that contains other domains. In this case, "isolated" means that the nucleic acid binding domain is sufficient to bind nucleic acid without the need for other domains that it may be expressed together with in naturally expressed proteins. The isolated nucleic acid binding domain may comprise additional amino acids that are not expressed naturally together with the nucleic acid binding domain, such as His-tag, Strep-tag and other known tags.

"Nucleic acid," as used herein, refers to any molecules used by organisms to transfer genetic information from one generation to the next. Nucleic acids include DNA and RNA and may consist of multiple nucleotides linked together. Nucleic acids may refer to naturally occurring forms, such as DNA or RNA from cells, or may refer to synthetic forms that do not occur in any organism. Nucleic acids would comprise both single-stranded and double-stranded nucleotides.

"Thermolability," as used herein, refers to release of bound nucleic acid at lower temperature. For example, a mutant nucleic acid binding domain (i.e., a domain comprising a mutation) with greater thermolability would release bound nucleic acid at a lower temperature compared with a non-mutated domain.

II. Nucleic Acid Binding Domains

The isolated nucleic acid binding domains described in this application can bind nucleic acids without the need for additional domains, that is, such isolated nucleic acid binding domain has nucleic acid binding activity. Preferably, the domain has non-sequence specific nucleic acid binding activity.

In some aspects, the isolated nucleic acid binding domain has homology to an amino acid sequence expressed naturally by an organism. In some aspects, the isolated nucleic acid binding domain has homology to the amino acid sequence domain of a naturally-occurring ComEA or DDE transposase protein.

In some aspects, an isolated nucleic acid binding domain comprises an amino acid sequence with at least 70%, 80%, 85%, 90%, 95%, 96%, 97%, 98%, or 99% identity to any of SEQ ID NOs: 1-24.

In some aspects, an isolated nucleic acid binding domain comprises an amino acid sequence with at least 70%, 80%, 85%, 90%, 95%, 96%, 97%, 98%, or 99% identity to SEQ ID NO: 15. In some aspects, an isolated nucleic acid binding domain comprises an amino acid sequence with at least 70%, 80%, 85%, 90%, 95%, 96%, 97%, 98%, or 99% identity to SEQ ID NO: 10. In some aspects, an isolated nucleic acid binding domain comprises an amino acid sequence with at least 70%, 80%, 85%, 90%, 95%, 96%, 97%, 98%, or 99% identity to SEQ ID NO: 2. In some aspects, an isolated nucleic acid binding domain comprises an amino acid sequence with at least 70%, 80%, 85%, 90%, 95%, 96%, 97%, 98%, or 99% identity to SEQ ID NO: 9. In some aspects, an isolated nucleic acid binding domain comprises an amino acid sequence with at least 70%, 80%, 85%, 90%, 95%, 96%, 97%, 98%, or 99% identity to SEQ ID NO: 23. In some aspects, an isolated nucleic acid binding domain comprises an amino acid sequence with at least 70%, 80%, 85%, 90%, 95%, 96%, 97%, 98%, or 99% identity to SEQ ID NO: 22.

In some aspects, an isolated nucleic acid binding domain comprises an amino acid sequence with at least 80% identity to a sequence selected from SEQ ID NO: 15, 2, 9, 1 to 14, 23, 22, 16 to 21, and 24. In some aspects, an isolated nucleic acid binding domain comprises the amino sequence of SEQ ID NOs: 1-24. In some aspects, an isolated nucleic acid binding domain comprises the amino sequence of SEQ ID NO: 15. In some aspects, an isolated nucleic acid binding domain comprises the amino sequence of SEQ ID NO: 2. In some aspects, an isolated nucleic acid binding domain comprises the amino sequence of SEQ ID NO: 9. In some aspects, an isolated nucleic acid binding domain comprises the amino sequence of SEQ ID NO: 10. In some aspects, an isolated nucleic acid binding domain comprises the amino sequence of SEQ ID NO: 23. In some aspects, an isolated nucleic acid binding domain comprises the amino sequence of SEQ ID NO: 22. In some aspects, the isolated nucleic acid binding domain amino acid sequence length is from about 37 to about 213 amino acids. Preferably, the isolated nucleic acid binding domain amino acid sequence length is from about 50 to about 160 amino acids. More preferably, the amino acid sequence length is from 60 to 80 amino acids.

In some aspects, the isolated nucleic acid binding domain has homology to the amino acid sequence domain of a naturally-occurring ComEA and has amino acid length from 60 to 70 amino acids. In some aspects, the isolated nucleic acid binding domain has homology to the amino acid sequence domain of a naturally-occurring DDE transposase protein and has amino acid length from 65 to 72 amino acids.

In some aspects, the isolated nucleic acid binding domain further comprises additional amino acids, such as His-tag, Strep-tag and other known tags.

In some aspects, the amino acid sequence of the isolated nucleic acid binding domain comprises one or more mutations compared to the amino acid sequence of the non-mutated nucleic acid binding domain.

In some aspects, the amino acid sequence of the isolated nucleic acid binding domain comprises the amino acid sequence of SEQ ID NO: 15 (ComEA15), but with one or more mutations at positions corresponding to positions 10, 16, 20, 23, 27, 41, 45, 51, 52, 54, 55, or 56 of SEQ ID NO: 15. In some examples, the amino acid sequence of the isolated nucleic acid binding domain comprises the amino acid sequence of SEQ ID NO: 15 (ComEA15), with an amino acid substitution T10K, L16F, S20K, A27T, S41N, D44G, K55R, E54Q, D44Y, I52F, D45Q, S41R or E54A or T56I. In further examples, the amino acid sequence of the isolated nucleic acid binding domain comprises the amino acid sequence of SEQ ID NO: 15 (ComEA15), with an amino acid substitution K55R, E54Q, D44Y, I52F, D45Q, S41R or E54A.

In some aspects, the amino acid sequence of the isolated nucleic acid binding domain comprises the amino acid sequence of SEQ ID NO: 9 (ComEA9), but with one or more mutations at positions corresponding to positions 19, 23, 27, 31, 33, 38, 39, 40, 41, or 42 of SEQ ID NO: 9. In some examples, the amino acid sequence of the isolated nucleic acid binding domain comprises the amino acid sequence of SEQ ID NO: 9 (ComEA9), with an amino acid substitution R19Y, R19N, R23P, A27R, A31D, A31N, R33G, G38N, F39Y, V40H, V40Y, R41N, A42T, or A42F. In further examples, the amino acid sequence of the isolated nucleic acid binding domain comprises the amino acid sequence of SEQ ID NO: 9 (ComEA9), with an amino acid substitution A31N.

In some aspects, the amino acid sequence of the isolated nucleic acid binding domain comprises the amino acid sequence of SEQ ID NO: 2 (ComEA2), but with one or more mutations at positions corresponding to positions 11, 16, 21, 26, 28, 29, 30, 32, 33, 40, 45, 46, 49, 51, 52, 58 or 59 of SEQ ID NO: 2. In some examples, the amino acid sequence of the isolated nucleic acid binding domain comprises the amino acid sequence of SEQ ID NO: 2 (ComEA2), with an amino acid substitution A11S, L16F, G21R, K26V, Q28K, R29D, I30L, D32A, Y33F, Y33H, F40L, E45A, L46V, L46V, V49A, G51R, G51D, I52V, E58D, K59R. In further examples, the amino acid sequence of the isolated nucleic acid binding domain comprises the amino acid sequence of SEQ ID NO: 2 (ComEA2), with an amino acid substitution R29D.

A. Motifs Comprised in Nucleic Acid Binding Domains

The isolated nucleic acid binding domains described in this application may comprise an amino acid motif. A motif comprises amino acids that are generally maintained in motifs from different naturally-occurring non-sequence specific nucleic acid binding domains. Amino acids that are generally present in the motifs across domains are termed "conserved" in this application. Conserved positions may generally show a single amino acid at this position of the motif across domains, or conserved positions may allow a fixed range of amino acids at a given position of the motif across domains.

A motif may also comprise amino acid positions that allow a range of amino acids at this position of the motif while retaining the ability to bind nucleic acid. In other words, some amino acid positions may be sequence flexible for what amino acid is comprised in the motif.

In some aspects, a motif is shared by naturally-occurring nucleic acid binding domains. In some aspects, a motif may be used to identify nucleic acid binding domains that are comprised in naturally-occurring proteins. Motifs may also be used to design isolated nucleic binding domains that do not occur naturally.

Exemplary motifs include $AX_4(L/M)X_4G(I/V)GX_6(I/V)X_3R$ (SEQ ID NOs: 25) and $NXAX_4(L/M)X_4G(I/V)GX_3AX_2(I/V)X_3RX_{7-11}LX_2VXGIG$ (SEQ ID NO: 26).

In these sequences, some amino acid positions are conserved, such that a specific amino acid or one of a range of amino acids (denoted by a slash) is present in most identified nucleic acid binding domains of this group. At other positions, the motif must comprise a set number of amino acids, but the position is flexible for a range of amino acids (denoted by X). At flexible positions, a certain number of amino acids may be required (such as $X_{4=4}$ amino acids).

In some aspects, the amino acid sequence of an isolated nucleic acid binding domain comprises SEQ ID NO: 25. In some aspects, the motif may comprise 1, 2, or 3 amino acid differences from SEQ ID NO: 25. In some aspects, the amino acid sequence of an isolated nucleic acid binding domain comprises at least one motif with at least 90%, 95%, 96%, 97%, 98%, or 99% identity to SEQ ID NO: 25.

In some aspects, the amino acid sequence of an isolated nucleic acid binding domain comprises SEQ ID NO: 26. In some aspects, the motif may comprise 1, 2, or 3 amino acid differences from SEQ ID NO: 26. In some aspects, the amino acid sequence of an isolated nucleic acid binding domain comprises at least one motif with at least 90%, 95%, 96%, 97%, 98%, or 99% identity to SEQ ID NO: 26.

SEQ ID NO: 26 comprises all motifs of SEQ ID NO: 25. In comparing SEQ ID NO: 26 to SEQ ID NO: 25, SEQ ID NO: 26 is a more stringent motif with additional requirements that SEQ ID NO: 25. As such, all motifs with homology to SEQ ID NO: 26 will also have homology to SEQ ID NO: 25.

In some aspects, a motif is used to design non-natural isolated nucleic acid binding domains. In particular, mutations to naturally-occurring motifs may be used to design isolated nucleic acid binding domains with different sequences than the natural motif. These nucleic acid binding domains with mutations may have unique properties not shared with naturally-occurring nucleic acid binding domains.

In some aspects, the amino acid sequence of the isolated nucleic acid binding domain comprises at least one amino acid mutation in a conserved amino acid position in SEQ ID NO: 25 or SEQ ID NO: 26. Exemplary isolated nucleic acid binding domain comprising at least one amino acid mutation in a conserved amino acid position in SEQ ID NO: 25 or SEQ ID NO: 26 is the isolated nucleic acid binding domain comprising the amino acid sequence of SEQ ID NO: 15 (ComEA15), but with one or more mutations at positions corresponding to positions 16, 23, 27, 51 or 52 of SEQ ID NO: 15, the isolated nucleic acid binding domain comprising the amino acid sequence of SEQ ID NO: 9 (ComEA9), but with a mutation at position corresponding to position 33 of SEQ ID NO: 9, or the isolated nucleic acid binding domain comprising the amino acid sequence of SEQ ID NO: 2 (ComEA2), but with one or more mutations at positions corresponding to positions 11, 16, 21, 30, 46, 49, 51 or 52 of SEQ ID NO: 2. In some aspects, the amino acid sequence of the domain comprises at least one amino acid mutation within 2 amino acids from a conserved amino acid position in SEQ ID NO: 25 or SEQ ID NO: 26. By "within 2"—it is meant that the one or more amino acid mutation occurs at the amino acid directly 5' or 3' to the conserved amino position or at the second amino acid 5' or 3' to the conserved amino acid position. Exemplary isolated nucleic acid binding domain comprising at least one amino acid mutation within 2 amino acids from a conserved amino acid position in SEQ ID NO: 25 or SEQ ID NO: 26 is the isolated nucleic acid binding domain comprising the amino acid sequence of SEQ ID NO: 15 (ComEA15), but with one or more mutations at positions corresponding to positions 10, 20, 41, 45, 54 or 55 of SEQ ID NO: 15, the isolated nucleic acid binding domain comprising the amino acid sequence of SEQ ID NO: 9 (ComEA9), but with one or more mutations at positions corresponding to positions 19, 23, 27 or 31 of SEQ ID NO:

9, or the isolated nucleic acid binding domain comprising the amino acid sequence of SEQ ID NO: 2 (ComEA2), but with one or more mutations at positions corresponding to positions 26, 28, 29, 32, 33 or 45 of SEQ ID NO: 2. In some aspects, the amino acid sequence of the domain comprises at least one amino acid mutation within 3, 4, 5, 6, 7, 8, or 9 amino acids from a conserved amino acid position in SEQ ID NO: 25 or SEQ ID NO: 26.

B. Nucleic Acids that can Bind Nucleic Acid Binding Domains

The nucleic acid binding domains described in this application can bind a range of nucleic acids. The nucleic acid may be single-stranded or double-stranded.

In some aspects, the isolated nucleic acid domain binds one or more nucleic acid with a Kd of less than or equal to 10 μM, less than or equal to 5 μM, less than or equal to 1 μM, less than or equal to 100 nM, or less than or equal to 50 nM.

In some aspects, the nucleic acid is DNA. In some aspects, the DNA is double-stranded. In some aspects, the DNA is single-stranded. In some aspects, the DNA is blunted. In some aspects, the DNA is dA-tailed.

In some aspects, the nucleic acid is RNA. In some aspects, the RNA is double-stranded. In some aspects, the RNA is single-stranded.

In some aspects, an isolated nucleic acid binding domain may bind one type of nucleic acid with a higher affinity that other types of nucleic acid.

The nucleic acid may be of any length.

For single-stranded nucleic acid, in some aspects, the nucleic comprises 20 or more nucleotides, 100 or more nucleotides, 1,000 or more nucleotides, 10,000 or more nucleotides, or 100,000 or more nucleotides. In some aspects, the nucleic acid comprises less than 100,000 nucleotides, less than 10,000 nucleotides, less than 1,000 nucleotides, less than 100 nucleotides, or less than 20 nucleotides. In some aspects, the nucleic acid comprises 20-10,000 nucleotides. In some aspects, the nucleic acid comprises 100-1,000 nucleotides.

For double-stranded nucleic acid, in some aspects, the nucleic comprises 20 or more base pairs, 100 or more base pairs, 1,000 or more base pairs, 10,000 or more base pairs, or 100,000 or more base pairs. In some aspects, the nucleic acid comprises less than 100,000 base pairs, less than 10,000 base pairs, less than 1,000 base pairs, less than 100 base pairs, or less than 20 base pairs. In some aspects, the nucleic acid comprises 20-10,000 base pairs. In some aspects, the nucleic acid comprises 100-1,000 base pairs.

C. Non-Sequence Specific Binding to Nucleic Acids

In some aspects, an isolated nucleic acid binding domain binds one or more nucleic acid in a non-specific or non-sequence specific manner. In other words, the isolated nucleic acid binding domain of this disclosure can bind to a nucleic acid without selecting for specific sequences of nucleotides/base pairs.

As will be described in this application, an isolated nucleic acid binding domain that displays non-specific binding to nucleic acid can be used for a range of applications that cannot be performed by a binding domain that displays sequence specific binding to nucleic acids. In some aspects, a non-sequence specific nucleic acid binding domain can isolate nucleic acid without selecting nucleic acids with specific sequences.

For example, a non-sequence selective nucleic acid binding domain could be used to isolate and remove DNA from a sample. A sequence-specific nucleic acid binding domain that could only bind DNA with certain sequences would not be as useful for this type of application, since it would not be able to isolate and/or remove all DNA in a sample.

D. Temperatures for Binding and not Binding of Nucleic Acids

The isolated nucleic acid binding domains described in this application may bind or not bind nucleic acids at a range of different temperatures. Specific temperatures for binding to nucleic acids could be important for different uses. For example, a specific temperature may be needed if other reactions (e.g. enzymatic reactions) are taking place during the binding. Binding or not binding of an isolated nucleic acid binding protein to a nucleic acid may occur at a range of different temperatures and/or different solutions comprising different salt concentrations.

Temperatures for Binding

In some aspects, the isolated nucleic acid binding domain can bind nucleic acid at any temperature above 0° C. In some aspects, the isolated nucleic acid binding domain binds nucleic acid at a temperature of 4° C. or greater, 25° C. or greater, 37° C. or greater, 42° C. or greater, or 65° C. or greater.

In some aspects, the isolated nucleic acid binding domain binds nucleic acid at a temperature from 4° C. to 72° C. In some examples, the isolated nucleic acid binding domain binds nucleic acid at a temperature from 25° C. to 65° C., preferably at a temperature from 25° C. to 42° C., more preferably at a temperature from 25° C. to 37° C. In further examples, the isolated nucleic acid binding domain binds nucleic acid at ambient or room temperature (i.e. at about 18° C. to 25° C.). Exemplary isolated nucleic acid domains that bind nucleic acid at listed temperatures may comprise amino acid sequence having at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24. Further exemplary isolated nucleic acid domains that bind nucleic acid at listed temperatures may comprise amino acid sequence selected from SEQ ID NO: 15, 10, 2, 9, 1, 3 to 8, 11 to 14, 23, 22, 16 to 21, and 24.

The isolated nucleic acid binding domains described in this application may have a number of profiles for tolerance to salt concentration. In other words, the isolated nucleic acid binding domains may be more or less permissive to changes in salt concentration when binding nucleic acid. The salt may be any salt. In some aspects, the salt may be any one of chloride salts, sulfate salts, phosphate or acetate salts. In some examples, the salt may be any one of chloride salts, sulfate salts, phosphate or acetate salts, that comprise sodium, potassium, magnesium, manganese or ammonium ions; the listed salts may also comprise different metal ions. In some examples, combination of salts may be used.

In some aspects, the salt is NaCl. In some aspects, an isolated nucleic acid binding domain binds nucleic acid at 0 M to 2.5 M NaCl. In some aspects, an isolated nucleic acid binding domain binds nucleic acid at 50 M to 2.5 M NaCl. In some aspects, an isolated nucleic acid binding domain binds nucleic acid at 50 to 1500 mM NaCl. In some aspects, an isolated nucleic acid binding domain binds nucleic acid at 50 mM to 700 mM NaCl. In some aspects, an isolated nucleic acid binding domain binds nucleic acid at 50 mM to 500 mM NaCl. In some aspects, an isolated nucleic acid binding domain binds nucleic acid at 100 mM to 500 mM NaCl, in particular, an isolated nucleic acid binding domain binds nucleic acid at 100 mM to 200 mM NaCl. In other examples, various suitable concentrations as provided herein may be of another salt or combination thereof; for example, the salt may be any one of chloride salts, sulfate salts, phosphate or acetate salts, that comprise sodium, potassium, magnesium, manganese or ammonium ions; the listed salts may also comprise different metal ions.

The isolated nucleic acid domain may bind the nucleic acid at temperatures for binding as described above, in a solution with salt concentration as described above, that is, the domain binds nucleic acid at conditions where a combination of binding temperature and incubation in a solution with a salt concentration is used. Exemplary nucleic acid binding domains are isolated nucleic acid binding domains comprising an amino acid sequence with at least 70%, 80%, 85%, 90%, 95%, 96%, 97%, 98%, or 99% identity to any of SEQ ID NOs: 1-24. Further exemplary domains are isolated nucleic acid binding domains comprising an amino acid sequence of any of SEQ ID Nos: 1-24. In some aspects, when the amino acid sequence of isolated nucleic acid binding domain comprises one or more amino acid mutation, the domain comprising at least one amino acid mutation is capable of binding nucleic acid at a similar temperature (as compared to the same domain without a mutation). In some aspects, when the amino acid sequence of isolated nucleic acid binding domain comprises one or more amino acid mutation, the domain comprising at least one amino acid mutation is capable of binding nucleic acid at a different temperature to the same domain without a mutation.

Temperatures for not Binding

Specific temperatures at which an isolated nucleic acid binding domain does not bind nucleic acid are also important. If an isolated nucleic acid binding domain bound to nucleic acid is incubated at or heated to a temperature at which the domain does not bind nucleic acid, the nucleic acid will be released. A temperature at which a domain does not bind nucleic acid thus would be a temperature at which nucleic acid is released or eluted from the isolated nucleic acid binding domain. A temperature at which a domain does not bind nucleic acid also may be referred to as an "elution temperature" or a "release temperature."

Isolated nucleic acid binding domains with lower elution temperatures would have a number of advantages. As used herein, "a lower elution temperature" is a temperature that is lower than 66° C., in particular, a lower elution temperature is from 25° C. to 65° C., from 25° C. to 42° C., more particularly from 25° C. to 37° C., or at ambient or room temperature (i.e. at about 18° C. to 25° C.), or at 22° C., 23° C., 24° C., 25° C., 26° C., 27° C., 28° C., 29° C., 30° C., 31° C., 32° C., 33° C., 34° C., 35° C., or 36° C. A lower elution temperature would allow ease of use for a scientist who wants to collect nucleic acid that has been bound to an isolated nucleic acid binding domain. A lower elution temperature may avoid damage to nucleic acids or other components of a buffer or reaction solution. Thus, a lower elution temperature may allow nucleic acid to be directly eluted into a reaction solution appropriate for downstream reactions (as will be described in the Methods of Use section), since components of the reaction solution will not be degraded at this lower elution temperature. A lower elution temperature may avoid melting, denaturation and/or degradation of nucleic acids.

Isolated nucleic acid binding domains with elution solution with low salt concentration or having no salt (e.g. water solution) would have a number of advantages. As used herein, "solution with low salt concentration or having no salt" is a solution that comprises from 0 to 50 mM NaCl salt, preferably, 0 to 20 mM NaCl salt. In some examples, the salt may be any one of chloride salts, sulfate salts, phosphate or acetate salts. In some examples, the salt may be any one of chloride salts, sulfate salts, phosphate or acetate salts, that comprise sodium, potassium, magnesium, manganese or ammonium ions; the listed salts may also comprise different metal ions. In some examples, combination of salts may be used. A "solution with low salt concentration or having no salt" may further comprise other components such as a buffering agent (e.g. Tris-HCl, Tris-acetate and other; for example, with a pH 5-9) or a chelating agent (e.g. EDTA) or other. A low salt or no salt elution solution may allow nucleic acid to be directly eluted into a reaction solution appropriate for downstream reactions (as will be described in the Methods of Use section), since many components of the reaction solution (e.g. enzymes) may tolerate only low salt concentrations. A no salt elution solution (e.g. water solution or a buffered solution) may allow nucleic acid to be conveniently used in any downstream methods or to be stored. In some examples, the nucleic acid binding domain that does not bind nucleic acid (i.e. nucleic acid is eluted from the nucleic acid binding domain) in a solution with low salt concentration or having no salt may be selected from the isolated nucleic acid domain comprising amino acid sequence SEQ ID NO: 10, the isolated nucleic acid domain comprising amino acid sequence SEQ ID NO: 15 with a mutation T10K, L16F, S20K, A27T, S41N, D44G, K55R, E54Q, D44Y, I52F, D45Q, S41R, E54A, or T56I, or the isolated nucleic acid domain comprising amino acid sequence SEQ ID NO: 2 with a mutation R29D. Preferably, the isolated nucleic acid binding domains (for example, the domains exemplified in this paragraph) do not bind nucleic acid in a solution with low salt concentration or having no salt (e.g. a buffer comprising 10 mM Tris-HCl, pH 8.0 or water, respectively) at 25° C. temperature. In other examples, the isolated nucleic acid binding domains (for example, the domains exemplified in this paragraph) do not bind nucleic acid in a solution with low salt concentration or having no salt at ambient or room temperature. In other examples, the isolated nucleic acid binding domains (for example, the domains exemplified in this paragraph) do not bind nucleic acid in a solution with low salt concentration or having no salt at 37° C. temperature.

In some embodiments, the isolated nucleic acid binding domain does not bind nucleic acid at a temperature of 60° C. or greater, of 65° C. or greater, 72° C. or greater, 80° C. or greater, 90° C. or greater, or 98° C. or greater.

In some aspects, the isolated nucleic acid binding domain does not bind nucleic acid at elevated temperatures, such as greater than 65° C., 72° C. or greater, 80° C. or greater, 90° C. or greater, or 98° C. or greater. Exemplary isolated nucleic acid domains that do not bind nucleic acid at listed temperatures may comprise amino acid sequence having at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24. Further exemplary isolated nucleic acid domains that bind nucleic acid at listed temperatures may comprise amino acid sequence selected from SEQ ID NO: 15, 10, 2, 9, 1, 3 to 8, 11 to 14, 23, 22, 16 to 21, and 24. When described elevated temperatures are used, a solution with salt concentration that is the same as salt concentration used for nucleic acid binding by an isolated nucleic acid binding domain, may be used. For example, if a solution with 200 mM NaCl was used for binding a nucleic acid by an isolated nucleic acid binding domain at an ambient temperature, elution may be performed by incubating in a solution with 200 mM NaCl at elevated temperature, e.g. greater than 65° C., 72° C. or greater, 80° C. or greater, 90° C. or greater, or 98° C. or greater.

In some aspects, when the amino acid sequence of isolated nucleic acid binding domain comprises one or more amino acid mutation, the domain comprising at least one amino acid mutation is capable of releasing bound nucleic acid at lower temperature compared to the same domain without a mutation. In other words, an isolated nucleic acid binding domain may be more thermolabile (i.e., have greater thermolability) than the domain without a mutation. In some aspects, when the amino acid sequence of isolated nucleic acid binding domain comprises one or more amino acid mutation, the domain comprising at least one amino acid mutation is capable of releasing bound nucleic acid at lower temperature and/or in the presence of lower amount of salt compared to the same domain without a mutation.

In some examples, the domains comprising at least one amino acid mutation that are capable of releasing bound nucleic acid at lower temperature and/or in the presence of lower amount of salt compared to the same domain without a mutation are selected from the isolated nucleic acid domain comprising amino acid sequence SEQ ID NO: 15 with a mutation K55R, E54Q, D44Y, I52F, D45Q, S41R or E54A, and the isolated nucleic acid domain comprising amino acid sequence SEQ ID NO: 2 with a mutation R29D. Preferably, the isolated nucleic acid binding domains do not bind nucleic acid in a solution with low salt concentration or having no salt (e.g. a buffer comprising 10 mM Tris-HCl, pH 8.5 or water, respectively) at 25° C. temperature.

In some aspects, an amino acid sequence of an isolated nucleic acid binding domain comprises at least one amino acid mutation in a conserved amino acid position in SEQ ID NO: 25 or SEQ ID NO: 26 or within 2 amino acids from a conserved amino acid position in SEQ ID NO: 25 or SEQ ID NO: 26, wherein the domain comprising at least one amino acid mutation is capable of releasing bound nucleic acid at lower temperature and/or in the presence of lower amount of salt compared to the same domain without a mutation. In other words, an isolated nucleic acid binding domain comprising at least one amino acid mutation in a conserved amino acid position in SEQ ID NO: 25 or SEQ ID NO: 26 or within 2 amino acids from a conserved amino acid position in SEQ ID NO: 25 or SEQ ID NO: 26 may have a lower elution temperature and/or elution solution with less or no salt for releasing bound nucleic acid compared to the same domain without the mutation.

In some aspects, this mutation is in the G(I/V)G sequence of SEQ ID NO: 25 or in the GIG sequence of SEQ ID NO: 26 or within 2 amino acids from any of said sequences.

E. Other Conditions for Binding Nucleic Acids

The isolated nucleic acid binding domains described in this application may have a number of profiles for binding one or more nucleic acid.

In some aspects, an isolated nucleic acid binding domain binds nucleic acid at relatively neutral, that is, at a non-denaturing, physiological pH. In some aspects, an isolated nucleic acid binding domain binds nucleic acid at pH 5-pH 9. In some aspects, an isolated nucleic acid binding domain binds nucleic acid at pH 7-pH 8.

Some isolated nucleic acid binding domains may not require salt to bind to nucleic acid, e.g. such domains may bind nucleic acid in water or buffered solution, at a binding temperature as listed above. Water or buffered solution may have other components such as chelating agent and other additives. Exemplary isolated nucleic acid binding domain that can bind nucleic acid in a water solution or in a buffered solution is a nucleic acid binding domain comprising an amino acid sequence of SEQ ID NO: 2. Further exemplary nucleic acid binding domains may be nucleic acid binding domains comprising amino acid sequence having at least 70%, 80%, 85%, 90%, 95%, 96%, 97%, 98%, or 99% identity to a sequence selected from SEQ ID Nos: 16-24, or nucleic acid binding domains comprising amino acid sequence of any of SEQ ID Nos: 16-24. Conditions when such nucleic acid binding domains do not bind nucleic acid, i.e. elute nucleic acid, may be incubation in water or buffered solution at elevated temperatures, such as 80° C. or greater, 90° C. or greater, or 98° C. or greater. In some examples, for example, when a nucleic acid binding domain comprising an amino acid sequence of SEQ ID NO: 2 is used, additives may be required for elution of nucleic acid, such as SDS, Urea, DMSO or proteinase. In some examples, additives may be used in combination with incubation at elevated temperatures. In some example, temperatures lower than 80° C. (for example, 62° C., 65° C., 72° C.) may be used.

The isolated nucleic acid binding domains may be more or less permissive to changes in salt concentration when binding nucleic acid. The salt may be any salt. In some aspects, the salt may be any one of chloride salts, sulfate salts, phosphate or acetate salts. In some examples, the salt may be any one of chloride salts, sulfate salts, phosphate or acetate salts, that comprise sodium, potassium, magnesium, manganese or ammonium ions; the listed salts may also comprise different metal ions. In some examples, combination of salts may be used.

In some embodiments, the salt is NaCl. In some embodiments, an isolated nucleic acid binding domain binds nucleic acid at 0 M to 2.5 M NaCl. In some embodiments, an isolated nucleic acid binding domain binds nucleic acid at 50 mM to 700 mM NaCl. In some embodiments, an isolated nucleic acid binding domain binds nucleic acid at 100 mM to 700 mM NaCl. In some embodiments, an isolated nucleic acid binding domain binds nucleic acid at 50 mM to 500 mM NaCl. In some embodiments, an isolated nucleic acid binding domain binds nucleic acid at 100 mM to 500 mM NaCl.

In some embodiments, the isolated nucleic acid binding domain does not require salt to bind to nucleic acid. In some embodiments, the isolated nucleic acid binding domain can bind nucleic acid in a water solution. Preferably, such isolated nucleic acid binding domain comprises an amino acid sequence with at least 70%, 80%, 85%, 90%, 95%, 96%, 97%, 98%, or 99% identity to SEQ ID NO: 2.

F. Tagging and Other Modifications of Nucleic Acid Binding Domains

In some aspects, the isolated nucleic acid binding domain is tagged. "Tagged," as used herein, refers to a peptide sequence attached to the domain. The peptide sequence of the tag is not meant to alter nucleic acid binding properties, but to serve a different purpose.

In some aspects, the tag is a His-tag, AviTag (SEQ ID NO: 27), SNAP-tag, Strep-tag T7-tag FLAG-tag S-tag HA-tag, c-Myc tag, GST-tag MBP-tag, CLIP-tag ACP-tag or MCP-tag.

In some aspects, the tag is fused to amino terminus of the domain. In some aspects, the tag is fused to carboxy terminus of the domain.

In some aspects, the tag is used for purification of the domain. In some aspects, the tag facilitates binding of the domain to a solid matrix.

In some aspects, the isolated nucleic acid binding domain is chemically or enzymatically modified. In some aspects, the chemical modification is biotinylation. In some aspects, chemical modification facilitates binding of the domain to a solid matrix.

G. Nucleic Acids Encoding Isolated Nucleic Acid Binding Domains

In some aspects, a nucleic acid encodes an isolated nucleic acid binding domain. In some aspects, a nucleic acid encodes an isolated nucleic acid binding domain comprising amino acid sequence having at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24. In some aspects, a nucleic acid encodes an isolated nucleic acid binding domain comprising amino acid sequence selected from SEQ ID NO: 15, 10, 2, 9, 1, 3 to 8, 11 to 14, 23, 22, 16 to 21, and 24. In some aspects, a nucleic acid sequence is optimized for expression in bacteria.

III. Compositions Comprising Isolated Nucleic Acid Binding Domains

This application also describes compositions comprising an isolated nucleic acid binding domain immobilized to a solid matrix. Compositions comprising isolated nucleic acid binding domains immobilized to a solid matrix may ease use in a variety of methods. For example, if the solid matrix of the composition is magnetic beads, the composition may be easy to separate out of a sample after the isolated nucleic acid binding domain has bound nucleic acids in the sample, because the magnetic beads of the composition are easily collected, e.g. by using magnetic stand.

In some aspects, the solid matrix is provided on a microchip or microcolumn. In some aspects, the solid matrix is magnetic particles, chemically modified agarose, dextran, polyacrylamide resin, silica gel, cellulose, glass, or a plastic surface. In some aspects, the magnetic particles are beads.

In some aspects, the isolated nucleic acid binding domain is immobilized to a solid matrix by covalent interactions, non-covalent interactions, passive adsorption, or entrapment.

A wide variety of chemical reactions for immobilizing proteins to substrates have been described (see Steen Redeker et al. *Bioconjugate Chemistry* 24(11):1761-77 (2013)). Any of these well-known methods may be used to immobilize isolated nucleic acid binding domains to a solid matrix.

In some aspects, the immobilization of an isolated nucleic acid binding domain to a solid matrix is by reaction of amine groups to N-hydroxysuccinimide (NHS), amine groups to carboxylic acid-, epoxy- or aldehyde-modified substrates, of thiols to maleimide-, disulfide-, pyridyl disulfide- or vinyl sulfone-modified substrates, of carboxylic acid groups to amine-modified substrates, of hydroxyl groups to epoxy-modified substrates, or via N,N'-dicyclohexyl carbodiimide-activated (DCC) carboxylic acid groups on amine-modified substrates.

In some aspects, the non-covalent interaction is between biotinylated isolated nucleic acid binding domain and a streptavidin-coated solid matrix. In some aspects, the non-covalent interaction is between streptavidin-tagged isolated nucleic acid binding domain and a biotinylated solid matrix.

In some aspects, the isolated nucleic acid binding domain of the composition is bound to nucleic acid.

In some aspects, a composition comprising an isolated nucleic acid binding domain immobilized to a solid matrix further comprises an enzyme immobilized to a solid matrix. In some aspects, the enzyme is immobilized to a solid matrix by the same or different interactions as an isolated nucleic acid binding domain. In some aspects, an isolated nucleic acid binding domain and an enzyme are immobilized on the same solid matrix. In some aspects, an isolated nucleic acid binding domain and an enzyme are immobilized on at least two different solid matrices. In some aspects, the enzyme is a modification enzyme. In further aspects, the enzyme is a DNA modification enzyme. In some aspects, the DNA modification enzyme is selected from ligase, restriction enzyme, deoxyribonuclease, ribonuclease, polynucleotide kinase and/or polymerase. In some aspects, the DNA modification enzyme is a deoxyribonuclease.

In some aspects, a composition comprises an isolated nucleic acid binding domain and a deoxyribonuclease (DNase) immobilized to a solid matrix. A deoxyribonuclease may be a wild type bovine DNase I or a variant thereof (e.g. halophilic mutant DNase I, hyperactive mutant DNase I), a human DNase I or a variant thereof, an equine DNase I or a variant thereof, a DNase from Pandalus borealis or a variant thereof. In some aspects the deoxyribonuclease is a bovine DNase I.

An isolated nucleic acid binding domains used in a composition comprising an isolated nucleic acid binding domain immobilized to a solid matrix and further comprising an enzyme immobilized to a solid matrix may be an isolated nucleic acid binding domain comprising amino acid sequence having at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24. The isolated nucleic acid binding domain may comprise amino acid sequence of any of SEQ ID NO: 15, 10, 2, 9, 1, 3 to 8, 11 to 14, 23, 22, 16 to 21, and 24. In general, it would be beneficial to use an isolated nucleic acid binding domain that does not elute nucleic acid under the same conditions as reaction conditions of an enzyme immobilized to a solid matrix. In some examples, a composition comprising an isolated nucleic acid binding domain immobilized to a solid matrix, wherein the isolated nucleic acid binding domain comprises amino acid sequence of SEQ ID NO: 2, and further comprises an enzyme immobilized to a solid matrix, wherein an enzyme is a modification enzyme, preferably, a DNA modification enzyme. In further examples, the DNA modification enzyme is selected from ligase, restriction enzyme, deoxyribonuclease, ribonuclease, polynucleotide kinase and/or polymerase. In further examples, a modification enzyme is a deoxyribonuclease. In particular, a deoxyribonuclease may be a wild type bovine DNase I or a variant thereof (e.g. halophilic mutant DNase I, hyperactive mutant DNase I), a human DNase I or a variant thereof, an equine DNase I or a variant thereof, a DNase from Pandalus borealis or a variant thereof. In some aspects the deoxyribonuclease is a bovine DNase I.

The immobilization of the enzyme to a solid matrix may be performed by using the interactions as described above for the nucleic acid binding domain.

In some aspects, the isolated nucleic acid binding domain of the composition is bound to nucleic acid.

IV. Methods of Identifying Candidate Isolated Nucleic Acid Binding Domains

This application also comprises methods of identifying one or more candidate isolated nucleic acid binding domain using alignment search. By "candidate," it is meant that the identified nucleic acid binding domain is selected for further evaluation.

As used herein, "alignment search," refers to aligning two or more amino acid sequences by similarity in sequence. An alignment search may involve aligning sequences and also inserting gaps between residues so that identical or similar amino acids are aligned. Using an alignment search, one skilled in the art could test for additional isolated nucleic acid binding domains in other proteins based on sequence similarity to known amino acid sequences of nucleic acid binding proteins or isolated nucleic acid binding domains. In this way, one skilled in the art can select new isolated nucleic acid binding domains for study based on previously selected domains.

In some aspects, a method of identifying one or more candidate isolated nucleic acid binding domain comprises performing an alignment search for detecting sequence similarity using an amino acid sequence of a nucleic acid binding protein or an isolated nucleic acid binding domain: reviewing results; and identifying one or more candidate isolated nucleic acid binding domain based on an expectation value of less than or equal to e-05.

As used herein, an "expectation value" or "expect value" refers to a parameter that describes the number of hits one can expect to see by chance when searching a database of a particular size. The lower the expectation value, or the closer it is to zero, the more "significant" the match is. In other words, when the expectation value is. e.g., e-02, e-05 or less, this means that the match between two sequences is unlikely to have occurred by chance, and such sequence match can be predictably identified as having relation and/or homology to the query sequence.

Setting a threshold for the degree of match, such as setting an expectation value threshold, limits the range of sequences that are identified. If too low an expectation value is used, then no matches will be found. In other words, too low an expectation value can be excessively stringent, and few candidate isolated nucleic acid binding domains would meet this criteria.

Conversely, if too high an expectation value is used, a large pool of candidate sequences could be selected. Too large a group of candidate sequences would lead to an unmanageable number of domains for further testing.

In some aspects, identifying one or more candidate isolated nucleic acid binding domain based on an expectation value of less than or equal to e-05 leads to selection of a group of candidate isolated nucleic acid binding domains that have a high likelihood to bind nucleic acid while not selecting a range of other domains that cannot bind nucleic acid with further testing.

The one or more candidate isolated nucleic acid binding domain can then be tested for nucleic acid binding properties. One skilled in the art may want certain characteristics of the isolated nucleic acid binding domain for different types of uses, such as lower elution temperature, preference for a particular type of nucleic acid versus others, or any other property. Candidate isolated nucleic acid binding domains could be expressed and tested for desired characteristics using standard binding assays and electrophoresis to determine the amount of various nucleic acid that was bound and eluted under certain conditions.

Alignment searching is also critically dependent on the sequences used for searching. As there are wide ranges of different nucleic acid binding domains in different naturally-occurring proteins, the starting point selected will highly impact the candidate isolated nucleic acid binding domains identified. An alignment search with a different starting point will obviously yield different candidate isolated nucleic acid binding domains.

In some aspects, the amino acid sequence of any one of SEQ ID NOs: 1-24 is used for performing an alignment search for detecting sequence similarity. In some aspects, the amino acid sequence of SEQ ID NO: 2 or SEQ ID NO: 23 is used for performing an alignment search for detecting sequence similarity.

Any alignment search that can evaluate amino acid similarity can be used. In some aspects, the alignment search is a BLAST search.

V. Methods of Use of Nucleic Acid Binding Domains

The isolated nucleic acid binding domains and compositions comprising these domains can be used in a wide variety of methods. In some aspects, these methods are for isolating nucleic acids.

In some aspects, a method of isolating nucleic acid from a sample comprises contacting one or more isolated nucleic acid binding domain with a sample comprising a nucleic acid under conditions suitable for binding, wherein the one or more isolated nucleic acid binding domain is bound to a solid matrix either before or after contacting it with a sample; and separating the sample from the solid matrix with the bound one or more isolated nucleic acid binding domain bound to nucleic acid.

In some aspects, a method of isolating nucleic acid from a sample comprises providing a composition comprising one or more isolated nucleic acid binding domain immobilized to a solid matrix; combining the composition comprising the one or more isolated nucleic acid binding domain immobilized to a solid matrix with a sample comprising a nucleic acid under conditions suitable for binding; and separating the sample from the composition comprising the one or more isolated nucleic acid binding domain immobilized to a solid matrix bound to nucleic acid. Using one or more isolated nucleic acid binding domain of the disclosure allows working with diluted nucleic acid samples, e.g. all nucleic acid from 2 ml volume of sample with concentration as low as 0.25 ng/μl can be bound. Preferably, the nucleic acid is DNA; for example, plasma sample may comprise low amounts of cell-free DNA.

"Conditions suitable for binding" may be any type of incubation needed for the nucleic acid to bind to an isolated nucleic acid binding domain. A variety of conditions may be suitable for binding. In some aspects, the conditions suitable for binding are incubation for less than or equal to 1 minute, less than or equal to 5 minutes, less than or equal to 10 minutes, less than or equal to 30 minutes, or less than or equal to 60 minutes. In some aspects, the conditions suitable for binding are incubation for 60 minutes or more. Other conditions suitable for binding are incubation in a solution with salt concentration from 0 to 2.5 M NaCl, incubation in a solution with salt concentration from 50 to 1500 mM NaCl, incubation in a solution with salt concentration from 50 to 500 mM NaCl, incubation in a solution with salt concentration from 100 to 500 mM NaCl, or, in particular, incubation in a solution with salt concentration from 100 to 200 mM NaCl. Conditions suitable for binding may be also incubation in a solution with the above listed salt concentrations of any one of chloride salts, sulfate salts, phosphate or acetate salts. In some examples, the salt may be any one of chloride salts, sulfate salts, phosphate or acetate salts, that comprise sodium, potassium, magnesium, manganese or ammonium ions; the listed salts may also comprise different metal ions. In some examples, combination of salts may be used. A solution may further comprise other components such as a buffering agent (e.g. Tris-HCl, Tris-acetate and other; for example, with a pH 5-9, preferably with a pH 7.0, 7.5, 8.0 or 8.5) or a chelating agent (e.g. EDTA) or other. In further aspects, conditions suitable for binding are incubation at a temperature from 4° C. to 72° (C, incubation at a temperature from 25° C. to 65° C., incubation at a temperature from 25° C. to 42° C., or incubation at a temperature from 25° C. to 37° C. In yet further aspects, conditions suitable for binding are incubation in a solution with salt concentration from 50 to 1500 mM NaCl at a temperature from 4° C. to 72° C. for less than or equal to 60 minutes. That is, the isolated nucleic acid binding domains of the current disclosure may bind nucleic acid at any of the indicated salt concentration range at any of the indicated temperature range after incubation for any of indicated time period.

Therefore, in some examples, a method of isolating nucleic acid from a sample comprises contacting one or more isolated nucleic acid binding domain comprising an amino acid sequence with at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24, with a sample comprising a nucleic acid under conditions suitable for binding, wherein the one or more isolated nucleic acid binding domain is bound to a solid matrix either before or after contacting it with a sample; and separating the sample from the solid matrix with the bound one or more isolated nucleic acid binding domain bound to nucleic acid, wherein the conditions suitable for binding are incubation in a solution with salt concentration from 100 to 500 mM NaCl at a temperature of 25° C. for less than or equal to 60 minutes. The incubation may be for less than or equal to 30 minutes, less than or equal to 10 minutes, less than or equal to 5 minutes, or less than or equal to 1 minute. Preferably, incubation is less than or equal to 30 minutes, more preferably, less than or equal to 10 minutes. In other examples, the conditions suitable for binding are incubation in a solution with salt concentration from 100 to 200 mM NaCl at a temperature of 25° C. for less than or equal to 30 minutes. In further examples, the conditions suitable for binding are incubation in a solution with salt concentration from 100 to 200 mM NaCl at a temperature of 37° C. for less than or equal to 30 minutes.

In some aspects, conditions suitable for binding may be incubation in a solution with low salt concentration or having no salt (i.e. a solution that comprises from 0 to 50 mM NaCl, preferably, from 0 to 20 mM NaCl), and which solution may further comprise other components such as a buffering agent (e.g. Tris-HCl) or a chelating agent (e.g. EDTA) or other) at a temperature from 4° C. to 65° C. for less than or equal to 60 minutes. In some examples, a method of isolating nucleic acid from a sample comprises contacting one or more isolated nucleic acid binding domain, with a sample comprising a nucleic acid under conditions suitable for binding, wherein the one or more isolated nucleic acid binding domain is bound to a solid matrix either before or after contacting it with a sample; and separating the sample from the solid matrix with the bound one or more isolated nucleic acid binding domain bound to nucleic acid, wherein the conditions suitable for binding are incubation in a solution with salt concentration from 0 to 50 mM NaCl at a temperature of 25° C. for less than or equal to 30 minutes, wherein the isolated nucleic acid binding domain comprises an amino acid sequence with at least 70%, 80%, 85%, 90%, 95%, 96%, 97%, 98%, or 99% identity to SEQ ID NO: 2. In particular, the isolated nucleic acid binding domain comprising an amino acid sequence of SEQ ID NO: 2 is useful in the method. In some aspects, the conditions suitable for binding are incubation in a solution with salt concentration 0 mM NaCl at a temperature of 25°

C. for less than or equal to 30 minutes, wherein the isolated nucleic acid binding domain comprises an amino acid sequence with at least 70%, 80%, 85%, 90%, 95%, 96%, 97%, 98%, or 99% identity to SEQ ID NO: 2.

In some aspects, a solid matrix of magnetic beads is used in the method.

In some aspects, the sample comprises genomic DNA or cell-free DNA. In some aspects, the sample comprises blood, plasma, serum, urine, saliva, cell lysate, enzymatic reaction mixture, or a buffer. In some aspects, the sample is an electrophoretic gel or an agarose gel. In some aspects, the sample is any solution that comprises nucleic acid.

In some aspects, the buffer is an electrophoretic buffer. In some aspects, the sample comprises nucleic acids that have been run through an electrophoretic gel. In some aspects, the isolating of nucleic acids is performed after the sample exits an electrophoretic gel. Using the isolated nucleic acid binding domain immobilized to a solid matrix to isolate the nucleic acid that has been run through an electrophoretic gel is beneficial, as sample and elution volumes can be controlled, also no purification steps of nucleic acid are required once the composition comprising the one or more isolated nucleic acid binding domain immobilized to a solid matrix bound to nucleic acid are separated from the sample. Additionally, when the composition comprising the one or more isolated nucleic acid binding domain immobilized to a solid matrix have been provided to the sample comprising nucleic acids that exits an electrophoretic gel, the nucleic acid binding domains may bind nucleic acid of selected specific length or they may bind to a range of nucleic acids of different sizes. This depends on the chosen time of running electrophoresis. The composition comprising the one or more isolated nucleic acid binding domain immobilized to a solid matrix can be used to bind nucleic acid during running electrophoresis. This is especially useful when pre-cast electrophoretic gels that have recovery wells are used, such as, for example, E-Gel (Invitrogen), FlashGel Recovery Cassette (Lonza), Pre-Cast Agarose Gel Cassettes for DNA Size Selection (Sage Science). When such type of electrophoretic gels is used, the composition comprising the one or more isolated nucleic acid binding domain immobilized to a solid matrix (solid matrix being, for example, magnetic beads) is loaded into the recovery well before the target size nucleic acid enters the recovery well and electrophoresis continues until all target nucleic acids (a specific size or a range of sizes of nucleic acids or fragments of nucleic acids) have entered the recovery well comprising the composition comprising the one or more isolated nucleic acid binding domain immobilized to a solid matrix. Then the composition comprising the one or more isolated nucleic acid binding domain immobilized to a solid matrix bound to target nucleic acid is collected from the recovery well. Thus the method of such isolation of nucleic acid from the sample is very convenient, as, e.g. nucleic acid fragments of certain size range can be isolated for further use, e.g. in NGS sequencing library preparation. In some examples, the isolated nucleic acid binding domains for use in isolating of nucleic acids from the above described sample that is an electrophoretic gel, an agarose gel or an electrophoretic buffer, are selected from nucleic acid domains comprising an amino acid sequence with at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24 or comprising an amino acid sequence of any of SEQ ID NO: 15, 10, 2, 9, 1, 3 to 8, 11 to 14, 23, 22, 16 to 21, and 24.

In some aspects, the isolating of nucleic acids from a sample that is an electrophoretic gel or an agarose gel is performed. In such cases, the isolation using the composition comprising the one or more isolated nucleic acid binding domain immobilized to a solid matrix is performed after the agarose gel comprising nucleic acids is melted by heating to a temperature of 37° C., 42° C., 50° C., 55° C., or 65° C. Preferably, the agarose gel is a low melting point agarose gel.

In some aspects, the nucleic acid is eluted from the one or more isolated nucleic acid binding domain before further steps. This provides flexibility to control eluted nucleic acid concentration—a preferred volume of elution solution can be provided, with a possibility to use very small volumes of elution solution. In some aspects, the elution is performed by heating to elevated temperature greater than 65° C., 72° C. or higher, 80° C. or higher, 90° C. or higher, or 98° C. or higher. In some aspects, the elution is performed by incubation in a solution with salt concentration from 0 to 2.5 M NaCl, incubation in a solution with salt concentration from 50 to 1500 mM NaCl, incubation in a solution with salt concentration from 50 to 500 mM NaCl, incubation in a solution with salt concentration from 100 to 500 mM NaCl, or incubation in a solution with salt concentration from 100 to 200 mM NaCl, at temperature greater than 65° C., 72° C. or higher, 80° C. or higher, 90° C. or higher, or 98° C. or higher. Incubation may be performed for less than or equal to 1 minute, less than or equal to 5 minutes, less than or equal to 10 minutes, less than or equal to 30 minutes, or less than or equal to 60 minutes. In some aspects, the conditions suitable for binding are incubation for 60 minutes or more. Such elution conditions may be used for example when isolated nucleic acid binding domain comprising an amino acid sequence with at least 70%, 80%, 85%, 90%, 95%, 96%, 97%, 98%, or 99% identity to a sequence selected from SEQ ID NO: 15, 10, 2, 9, 1, 3 to 8, 11 to 14, 23, 22, 16 to 21, and 24 is used in the method. When described elevated temperatures are used, a solution with salt concentration that is the same as salt concentration used for nucleic acid binding by an isolated nucleic acid binding domain, may be used. For example, if a solution with 200 mM NaCl was used for binding a nucleic acid by an isolated nucleic acid binding domain at an ambient temperature, elution may be performed by incubating in a solution with 200 mM NaCl at elevated temperature, e.g. 80° C.

In some aspects the elution in the method is performed by incubation in a solution with salt concentration 0 to 50 mM NaCl, by incubation in a buffered solution, or by incubation in water, at temperature of 65° C. or higher, 72° C. or higher, 80° C. or higher, 90° C. or higher, or 98° C. or higher. In further aspects, by incubation in a solution with salt concentration 0 to 20 mM NaCl is used. Incubation may be performed for less than or equal to 1 minute, less than or equal to 5 minutes, less than or equal to 10 minutes, less than or equal to 30 minutes, or less than or equal to 60 minutes. In some aspects, the conditions suitable for binding are incubation for 60 minutes or more. When described elevated temperatures are used, a solution with salt concentration that is the same as salt concentration used for nucleic acid binding by an isolated nucleic acid binding domain, may be used.

In other aspects, elution step in a method is by incubation in solution with low salt concentration or having no salt is performed at temperatures from 25° C. to 65° C., from 25° C. to 42° C., more particularly from 25° C. to 37° C., or at ambient or room temperature (i.e. at about 18° C. to 25° C.), or at 22° C., 23° C., 24° C., 25° C., 26° C., 27° C., 28° C., 29° C., 30° C., 31° C., 32° C., 33° C., 34° C., 35° C., or 36° C. In such case, preferably, the elution is performed by incubation in a solution with low salt concentration or having no salt (i.e. a solution that comprises from 0 to 50 mM NaCl, preferably from 0 to 20 mM NaCl, and which solution may further comprise other components such as a buffering agent (e.g. Tris-HCl) or a chelating agent (e.g. EDTA) or other) at the same temperature as compared to the temperature of the conditions suitable for binding (i.e. without changing the temperature as compared to the temperature of the conditions suitable for binding) for less than or equal to 1 minute, less than or equal to 5 minutes, less than or equal to 10 minutes, less than or equal to 30 minutes, or less than or equal to 60 minutes. For example, the nucleic acid is eluted from the isolated nucleic acid binding domain selected from the isolated nucleic acid domain comprising amino acid with at least 70%, 80%, 85%, 90%, 95%, 96%, 97%, 98%, or 99% identity to a sequence from: SEQ ID NO: 10, a SEQ ID NO: 15 with a mutation K55R, E54Q, D44Y, I52F, D45Q, S41R or E54A, or SEQ ID NO: 2 with a mutation R29D, by incubation in a solution that comprises from 0 to 20 mM NaCl, at temperature of 25° C. for less than or equal to 30 minutes. In particular, the nucleic acid is eluted from the isolated nucleic acid binding domain selected from the isolated nucleic acid domain comprising amino acid with a sequence from: SEQ ID NO: 10, a SEQ ID NO: 15 with a mutation K55R, E54Q, D44Y, I52F, D45Q, S41R or E54A, or SEQ ID NO: 2 with a mutation R29D. In further examples, elution may be by incubation in water or a buffered solution (e.g. TE buffer: 10 mM Tris-HCl, pH 8.0, 1 mM EDTA), at temperature of 25° C. for less than or equal to 30 minutes. In further examples, ambient or room temperature may be used for elution. Incubation may be performed for less than or equal to 1 minute, less than or equal to 5 minutes, less than or equal to 10 minutes, less than or equal to 30 minutes, or less than or equal to 60 minutes. In some aspects, the conditions suitable for binding are incubation for 60 minutes or more.

In some aspects, the nucleic acid is enzymatically or chemically modified without disrupting the binding of the nucleic acid to the isolated nucleic acid binding domain.

A wide variety of chemical modifications can be performed. In some aspects, the chemical modification is bisulfite modification, alkylation, click chemistry, or chemical ligation.

A wide variety of enzymatic modifications also can be performed. In some aspects, the enzymatic modification is performed by a ligase, restriction enzyme, or polymerase. In some aspects, the enzymatic modification is ligation, phosphorylation, or dephosphorylation. In some aspects, the enzymatic modification is end blunting, tailing of ends, phosphorylation or dephosphorylation of nucleic acid ends, ligation of synthetic adapters to nucleic acid ends, or enzymatic fragmentation of nucleic acid (e.g. by using deoxyribonuclease or transposase).

In some aspects, multiple steps of an enzyme modification or multiple enzymatic modifications to the nucleic acid are performed without disrupting the binding of the one or more nucleic acid to the isolated nucleic acid binding domain. In other words, the nucleic acid may remain bound to the isolated nucleic acid binding domain through a series of more than one enzymatic modification.

In some aspects, the nucleic acid is prepared for next generation sequencing by performing multiple steps of an enzyme modification or by performing multiple enzymatic modifications.

In some aspects, a method of isolating nucleic acid from a sample comprises contacting a composition comprising an isolated nucleic acid binding domain and an enzyme immobilized to a solid matrix, with a sample comprising a nucleic acid under conditions suitable for binding; and separating the sample from the solid matrix with the bound one isolated nucleic acid binding domain bound to nucleic acid. In some aspects, an isolated nucleic acid binding domain and an enzyme are immobilized on the same solid matrix. In some aspects, an isolated nucleic acid binding domain and an enzyme are immobilized on at least two different solid matrices.

In some aspects the method comprises a step, wherein the nucleic acid is enzymatically modified without disrupting the binding of the nucleic acid to the isolated nucleic acid binding domain. The nucleic acid may be enzymatically modified before or after separating the sample from the solid matrix with the bound isolated nucleic acid binding domain bound to nucleic acid. In some aspects, the nucleic acid is enzymatically modified by the enzyme immobilized to the solid matrix. In some aspects, the conditions suitable for binding are also suitable for enzymatic reaction by the enzyme immobilized to the solid matrix. That way, the nucleic acid is bound by a nucleic acid binding domain and modified by an enzyme at the same conditions of buffer, temperature and incubation time. This is beneficial, as, for example, no additional steps of washing and changing a buffer are needed. Also, if downstream steps of enzymatic modification require conditions different that those suitable for the enzyme immobilized to a solid matrix, the reaction buffer can be easily removed, and a new buffer can be provided. In some aspects, further steps of an enzyme modification to the nucleic acid are performed without disrupting the binding of the one or more nucleic acid to the isolated nucleic acid binding domain. In some aspects, the nucleic acid is eluted from the one or more isolated nucleic acid binding domain before further steps.

In some aspects, the enzyme is a modification enzyme. In further aspects, the enzyme is a DNA modification enzyme. In some aspects, the DNA modification enzyme is selected from ligase, restriction enzyme, deoxyribonuclease, ribonuclease, polynucleotide kinase and/or polymerase. In some aspects, the DNA modification enzyme is a deoxyribonuclease. In some aspects, a deoxyribonuclease is a DNase I. In particular, a deoxyribonuclease may be a wild type bovine DNase I or a variant thereof (e.g. halophilic mutant DNase I, hyperactive mutant DNase I), a human DNase I or a variant thereof, an equine DNase I or a variant thereof, a DNase from Pandalus borealis or a variant thereof. In some aspects the deoxyribonuclease is a bovine DNase I. Using a deoxyribonuclease and a nucleic acid binding domain as in the described method provides additional advantage of fragmenting the nucleic acid bound to the nucleic acid binding domain. Such way of nucleic acid fragmentation may additionally provide fragmented nucleic acid molecules of certain length. For example, higher deoxyribonuclease immobilization density on solid matrix may produce shorter nucleic acid fragment size range, whereas lower deoxyribonuclease immobilization density may produce longer nucleic acid fragment size range.

In some aspects, the nucleic acid binding domain has at least 80% identity to a sequence selected from SEQ ID NO: 15, 2, 9, 1 to 14, 23, 22, 16 to 21, and 24. In some aspects, the nucleic acid binding domain has at least 80% identity to a sequence selected from SEQ ID NO: 15, 2, 9, or 10.

In some aspects, a method of isolating nucleic acid from a sample comprises contacting a composition comprising an isolated nucleic acid binding domain having at least 80% identity to a sequence selected from SEQ ID NO: 15, 2, 9, or 10 and a DNA modification enzyme immobilized to a solid matrix, with a sample comprising a nucleic acid under conditions suitable for binding; and separating the sample from the solid matrix with the bound one isolated nucleic acid binding domain bound to nucleic acid. In some aspects, an isolated nucleic acid binding domain and an enzyme are immobilized on the same solid matrix. In some aspects, the DNA modification enzyme is a deoxyribonuclease. In some aspects, the isolated nucleic acid binding domain is ComEA2 (SEQ ID NO: 2), and deoxyribonuclease is bovine DNase I or a variant thereof.

In some aspects, isolating nucleic acid from a sample is for depleting nucleic acid from a sample. In some aspects, the sample is a water solution. In some aspects, the sample is not a water solution.

Depletion of nucleic acid may be useful for a number of different types of samples. The presence of one or more nucleic acid in a variety of samples would be considered a contaminant. As such, removal of nucleic acid may be a "decontamination" of the sample. Any type of sample could undergo nucleic acid decontamination using an isolated nucleic acid binding domain.

In some aspects, the method is for DNA decontamination of a sample. In some aspects, the one or more isolated nucleic acid binding domain binds single-stranded DNA for depleting single-stranded DNA from a sample. In some aspects, the method depletes more single-stranded DNA than double-stranded DNA from a sample comprising double-stranded and single-stranded DNA.

In some aspects, the one or more isolated nucleic acid binding domain binds RNA for depleting RNA from a sample. In some aspects, the sample is formalin-fixed paraffin-embedded (FFPE) tissue.

VI. Kits Comprising Isolated Nucleic Acid Binding Domains

Kits comprising isolated nucleic acid binding domains may also have a variety of uses.

In some aspects, a kit comprises one or more isolated nucleic acid binding domain and a suitable buffer for binding the one or more isolated nucleic acid binding domain with nucleic acid. In some aspects, kits comprise one or more isolated nucleic acid binding domain is immobilized to a solid matrix.

In some aspects, a kit further comprise a solid matrix not immobilized to the isolated nucleic acid binding domain.

In some aspects, a solid matrix for immobilizing the isolated nucleic acid binding domain is provided separately from the one or more isolated nucleic acid binding domain.

In some aspects, a kit further comprises an elution buffer for eluting nucleic acid from the one or more isolated nucleic acid binding domain.

In some aspects, a kit further comprises one or more buffer or reagent for additional chemical or enzymatic modifications. In some aspects, the additional enzyme modifications are one or more of ligation, phosphorylation, or dephosphorylation. In some aspects, the additional enzymatic modifications are one or more of end blunting, tailing of ends, phosphorylation or dephosphorylation of nucleic acid ends, ligation of synthetic adapters to nucleic acid ends, or enzymatic fragmentation of nucleic acid (e.g. by using deoxyribonuclease or transposase).

In some aspects, a kit comprises one or more isolated nucleic acid binding domain and a suitable buffer for binding the one or more isolated nucleic acid binding domain with nucleic acid. In some aspects, kits comprise an isolated nucleic acid binding domain immobilized to a solid matrix and an enzyme immobilized to a solid matrix. In some aspects, an isolated nucleic acid binding domain and an enzyme are immobilized on the same solid matrix. In some aspects, an isolated nucleic acid binding domain and an enzyme are immobilized on at least two different solid matrices. In some aspects, the enzyme is a modification enzyme, for example, a DNA modification enzyme. In some aspects, the DNA modification enzyme is selected from ligase, restriction enzyme, deoxyribonuclease, ribonuclease, polynucleotide kinase and/or polymerase. In some aspects, the deoxyribonuclease is a bovine DNase I.

In some aspects, the kit is for use in depleting one or more nucleic acid from a sample.

EXAMPLES

Example 1: Computational Design of Nucleic Acid Binding Domains

The following examples are provided to illustrate certain disclosed examples and are not to be construed as limiting the scope of this disclosure in any way.

A total of 19 representative sequences of nucleic acid binding proteins were selected based on a literature review (fee Doherty et al. *Nucleic Acids Res.* 24(13):2488-97 (1996) and Alzbutas et al., *Front Microbiol.* 6:661 (2015)). Selected sequences were used as an input for the PSI-BLAST iterative search tool (Altschul et al., *Nucleic Acids Res.* 25:3389-402 (1997)), which constructed multiple sequence alignments with cutoff E-value of 0.001. Eight search iterations were performed against the protein database of thermophilic bacteria (ExtremophileDB, http://extremophiledb.igib.res.in, 2015; Majihi et al., *PLoS One* 8(5):e63083 (2013); and Majhi et al., PLoS ONE 12(6): e0179119 (2017). The most promising candidates among the identified proteins or isolated domains were selected by preserving key homologous sequences. Selection criteria for choosing proteins or isolated domains were:

1) protein/isolated domain size about 10 kDa;
2) protein/isolated domain should show the potential to interact with nucleic acids (e.g. nucleic acid-binding motifs found in other proteins like HhH);
3) protein/isolated domain interaction with nucleic acids should be sequence non-specific; and
4) theoretical dissociation constant value of protein- or isolated domain-nucleic acid interaction should be in the range of 0.1-50 nM.

Figure 13:
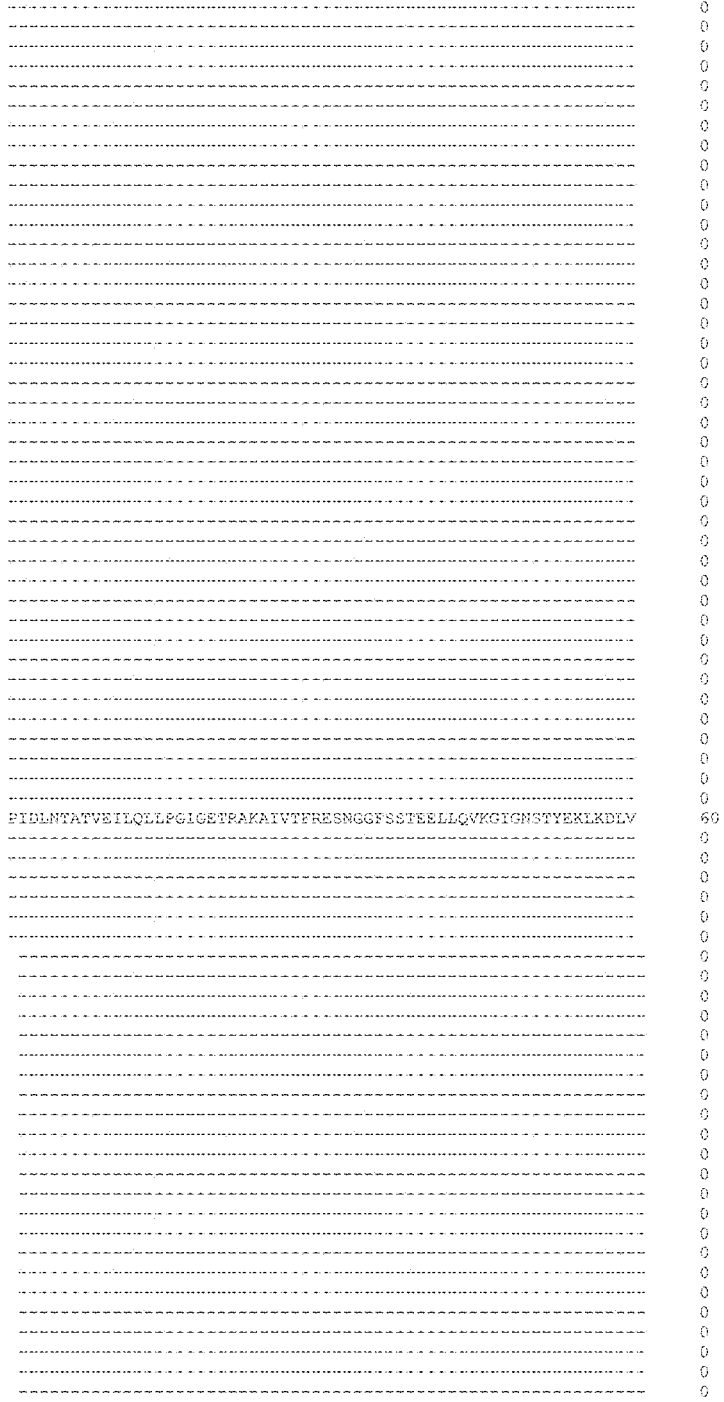
FIG. 13 provides an alignment of 72 ComEA type domains as discussed in Example 1. Dashes indicate where a particular sequence did not have an amino acid at a given position of the alignment. Because the sequences in FIG. 13 span multiple pages, Applicant provided a SEQ ID NO: for each sequence on the first page of the four-page FIG. 13.

FIG. 13 shows alignment of 72 ComEA type domains identified by this method. The sequences of these candidate domains are SEQ ID Nos: 52-123 and the SEQ ID Nos are provided in the first page of the four-page FIG. 13.

All SEQ ID NOs: 52-123 comprise at least one conserved sequence comprising $AX_4(L/M)X_4G(I/V)GX_6(I/V)X_3R$ (SEQ ID NO: 25) or $NXAX_4(L/M)X_4G(I/V)GX_3AX_2(I/V)X_3RX_{7-11}LX_2VXGIG$ (SEQ ID NO: 26).

FIG. 12 shows detailed alignment of ComEA1-ComEA15. All sequences have the motif of SEQ ID NO: 25

Example 2: Cloning and Purification of In Vivo Biotinylated Isolated Nucleic Acid Binding Domains Candidate nucleic acid binding domains were engineered to contain an amino-terminal 6-His-tag (SEQ ID NO: 131)

for purification adjacent to the site-specific biotinylation site AviTag™ (SEQ ID No: 27). Genes encoding candidate nucleic acid binding domains were de novo synthesized using DNA 2.0 commercial gene synthesis service (Newark, CA, USA). Gene sequences were optimized for expression in *Escherichia coli. Genes were cloned into a pTTQ*18 plasmid vector (Stark, 1987) under the control of $P_{taq}$ promoter and expressed in *E. coli* strain (Avidity, CO, USA) in the presence of 50 µM D-biotin. Growth medium comprising 6 g/L $KH_2PO_4$, 4 g/L $K_2HPO_4$, 1.5 g/L $NH_4Cl$, 10 g/L glycerol, 10 g/L tryptone, 5 g/L yeast extract, and 2.68 g/L $(NH_4)_2SO_4$. pH 7.0 was used for fermentation. Cells were grown at 37° C. with 200 rpm shaking. The expression of genes encoding nucleic acid binding domains was induced when bacterial culture has reached $OD_{600\ nm}$ ~5.0 upon addition of isopropylthio-β-galactoside (IPTG) to the final concentration of 1 mM. The expression of chromosomally encoded BirA ligase was simultaneously induced upon addition of L-arabinose to the final concentration of 0.4%. After 3 hours of post-induction incubation at 37° C. with 200 rpm shaking, cells were harvested and resuspended in 50 mM Tris-HCl, pH 8.5, 300 mM NaCl solution. Bacterial cells were disintegrated by ultrasonic treatment. Lysate was heated to 65° C. for 10 min, then chilled to 4° C. Cellular nucleic acids were precipitated by titration with polyethyleneimine (PEP) to the final concentration of 0.4%. Soluble domains were salted out upon addition of ammonium sulfate to the final concentration of 80%. The precipitate was collected by centrifugation, resuspended in 20 mM Tris-HCl, pH 8.0, 300 mM NaCl, and 25 mM imidazole and then dialyzed overnight against the same buffer.

His-tagged nucleic acid binding domains were purified using HisPur™ Ni-NITA resin (2 mL of resin per grain of biomass) (Thermo Scientific, MA, USA). Domain purification was performed with ÄKTA purifier (GE Healthcare Life Sciences, MA, USA) system with a flow speed of 0.3 mL/min. After domain binding to the resin, the column was washed with 5 column volumes of 20 mM Tris-HCl, pH 8.0, 300 mM NaCl, 25 mM imidazole solution. Target nucleic acid binding domains were eluted by an imidazole gradient of 25-400 mM. The physical purity of domain fractions was assessed by SDS-PAGE. Samples were tested for nuclease contamination by incubation with $^{33}$P-labelled short double-stranded DNA fragment. Fractions with >90% purity of target nucleic acid binding domains and exhibiting no detectable nuclease activity were concentrated in 20 mM Tris-HCl, pH 8.0, 150 mM NaCl, 0.1 mM EDTA, 50% glycerol, 0.5% Triton X-100 buffer and used in further experiments. Greater than 90% nucleic acid binding domain in vivo biotinylation efficiency was confirmed by mass spectrometric analysis.

Example 3: Functional Characterization of Nucleic Acid Binding Domains

Predicted nucleic acid-domains interactions were tested by electrophoretic mobility shift assay (EMSA). 25 bp double-stranded DNA fragment (GC content 52%), 40 nucleotide (nt) single-stranded DNA oligonucleotide (GC content 33%), 193 bp double-stranded RNA fragment, and 100 nt single-stranded RNA were radioactively labelled and used as substrates. The formation of nucleic acid-domain complexes was tested in Tris-acetate (40 mM Tris-acetate, pH 7.5, 10% glycerol) and MES-His (30 mM MES, 21 mM L-histidine, pH 6.0, 10% glycerol) buffers in the presence of 1 nM of the nucleic acid under investigation and increasing concentrations of nucleic acid binding domains. The resulting samples were resolved on a native 8% polyacrylamide gel (for RNA-nucleic acid binding domains complex formation reaction mixtures) or 15% SDS-PAGE (for DNA-nucleic acid binding domains complex formation reaction mixtures). FIGS. 2A-2D show DNA results and FIG. 3A-3D show RNA results. Dissociation constant values of tested nucleic acid-domain interactions ranged from 10 nM-3.3 μM (as summarized in FIG. 1).

Example 4: Coupling of Nucleic Acid Binding Domains to Solid Surfaces

Biotinylated nucleic acid binding domain ComEA2 (SEQ ID NO: 2) was immobilized on streptavidin-coated magnetic beads (Invitrogen Dynabeads™ MyOne™ Streptavidin, Thermo Scientific, MA, USA) following manufacturer's recommendations for coupling of biotinylated peptides. Functional activity of nucleic acid binding domains coupled to magnetic beads (MB) was confirmed by incubation of different amounts of DNA with nucleic acid binding domains coupled to magnetic beads (MB) in TE buffer (10 mM Tris-HCl, pH 8.0, 1 mM EDTA) at room temperature (25° C.) for 5 min, followed by electrophoretic analysis.

Figure 4:
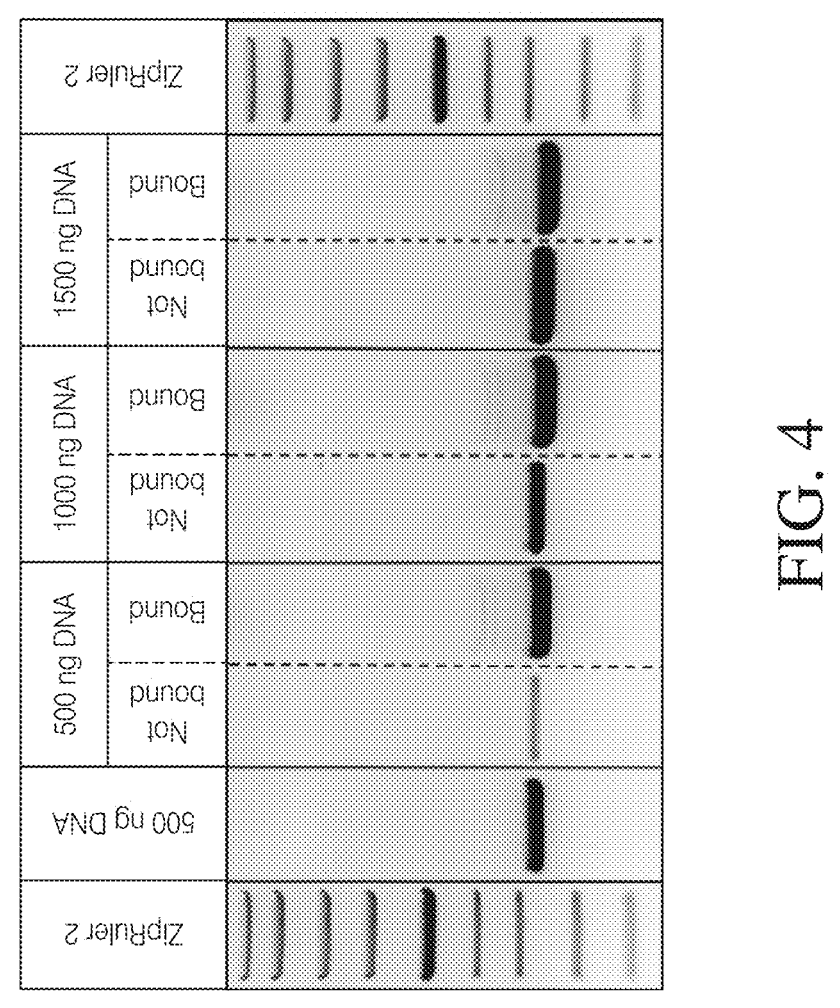

The amount of unbound nucleic acid (measured by the amount of DNA not bound) increased with increasing amounts of DNA (FIG. 4).

Example 5: Transfer and Enzymatic Modifications of Nucleic Acids Bound to Nucleic Acid Binding Domains A nucleic acid binding domain was assessed for the ability to capture DNA in enzymatic reaction mixture. Further, it was assessed whether the ends of captured nucleic acid fragments were then accessible for DNA-modifying enzymes.

The experiment was conducted using 250 ng, 500 ng and 1 μg of 260 base pair (bp) double-stranded DNA fragment as an input and in vivo biotinylated ComEA2 (SEQ ID No: 2, as shown in FIG. 1) nucleic acid binding domain immobilized on streptavidin-coated magnetic beads as the interaction partner, binding was performed in TE buffer at room temperature (25° C.) for 10 minutes Then the DNA fragment was blunted and dA-tailed following standard DNA end conversion protocol in 50 μL of 1× End Conversion Master Mix (ClaSeek™ NGS Library Preparation Kit, Thermo Scientific, MA, USA). 250 μg of streptavidin-coated magnetic beads with immobilized ComEA2 nucleic acid binding domain and bound DNA was added to the end conversion reaction mixture and incubated at room temperature (25° C.) for 5 min. Beads were collected on side of the tube using rack magnet, and the supernatant was discarded. Beads were resuspended in 50 μL of 1× Rapid Ligation buffer (Thermo Scientific, MA, USA) containing 35 U of T4 DNA ligase (Thermo Scientific, MA, USA) and 70 pmol of double-stranded synthetic adapters. The ligation reaction was performed for 30 min at room temperature (25° C.). Beads were collected on side of the tube, and supernatant was discarded. To elute DNA, beads were resuspended in 20 μL of TE buffer (10 mM Tris-HCl, pH 8.0, 1 mM EDTA) supplemented with 1×DNA Loading Dye & SDS Solution (Thermo Scientific, MA, USA) and heated at 70° C. for 10 min. Sodium dodecyl sulphate (SDS) was used additive in order to release DNA bound to ComEA2 domain.

Figure 5:
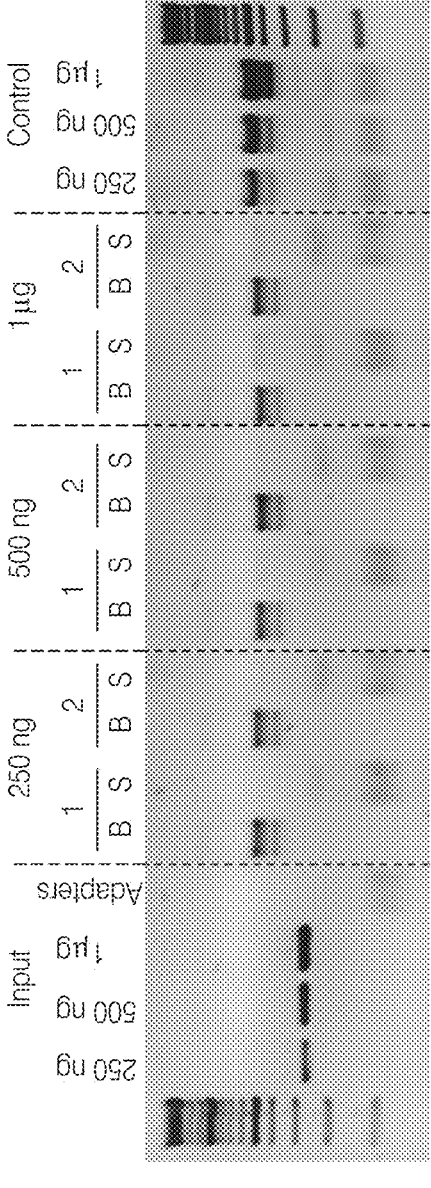
FIG. 5 shows results of an enzymatic reaction experiment. Adapter-ligated 260 base pair (bp) double-stranded DNA fragment was obtained via enzymatic manipulations performed on ComEA2 (SEQ ID No: 2) coated magnetic beads. "S" lanes indicate unbound DNA left in the end conversion reaction mixture. "B" lanes indicate bound DNA. "Control" lanes indicate products of identical enzymatic reactions executed in the absence of magnetic beads. The DNA size marker was GeneRuler DNA Ladder Mix (Thermo Fisher Scientific, MA, USA).

Supernatant and eluate were analyzed on 2% agarose gel (FIG. 5). Bound DNA ("B" lanes) indicate that DNA eluted from the beads after adapter ligation step for all bead concentrations. This shows that DNA bound to streptavidin-coated magnetic beads with immobilized ComEA2 nucleic acid binding domain was accessible for ligation with adapters. Further, comparison of the bound DNA and the "Control" lanes indicate products of same size were generated with the identical enzymatic reactions executed in the absence of magnetic beads. Thus, DNA bound to streptavidin-coated magnetic beads with immobilized nucleic acid binding domain can undergo enzymatic modification, avoiding a need to elute the DNA before downstream reactions.

Example 6: Conversion of DNA Fragments into Next Generation Sequencing-Ready Library

*Escherichia coli* genomic DNA was physically sheared in 130 μL volume using Covaris® instrument (Covaris, MA, USA) with the following settings: peak incident power—175 W, duty factor—10%, 200 cycles per burst, treatment time—180 s. Then ~300 ng of sheared DNA was captured by the ComEA2 (FIG. 1, SEQ ID No: 2) nucleic acid binding domain by incubation with ComEA2-coated magnetic beads in TE buffer (10 mM Tris-HCl, pH 8.0, 1 mM EDTA) at room temperature (25° C.) for 5 min. Magnetic beads were collected on the side of the tube using rack magnet, and supernatant was discarded. Beads were resuspended in 50 μL of 1× End Conversion Master Mix (ClaSeek™ NGS Library Preparation Kit, IT, Thermo Scientific, MA, USA) and incubated at 20° C. for 5 min. Beads were collected on side of the tube, supernatant was discarded. 100 μL of 1× Ligation Mix (ClaSeek™ NGS Library Preparation Kit, IT, Thermo Scientific, MA, USA) containing Ion Xpress™ adapters (Thermo Scientific, MA, USA) was immediately added to the beads. The ligation reaction was performed at 20° C. for 5 min. Beads were collected on side of the tube, and supernatant was discarded.

50 μL of TE buffer (10 mM Tris-HCl, pH 8.0, 1 mM EDTA) supplemented with 2 mg/mL of proteinase K (Thermo Scientific, MA, USA) was then added to the beads and incubated at room temperature (25° C.) for 10 min. Proteinase K was used in order to release DNA from ComEA2 domain. Beads were collected on side of the tube. Supernatant was then transferred to the clean tube and beads were discarded. DNA in the resulting supernatant was purified using Agencourt® AMPure® XP beads (Beckman Coulter, CA, USA) following manufacturer's instructions. DNA size selection targeting ~330 bp fragments was performed using E-Gel® SizeSelect™ 2% agarose gel (Thermo Scientific, MA, USA). The presence of sequencing-ready molecules in the resulting sample was confirmed by qPCR according to the standard Ion Library TaqMan™ Quantitation Kit (Thermo Scientific, MA, USA) protocol. The resulting library was sequenced on the Ion Torrent™ Personal Genome Machine® (PGM) system using Ion 316™ Chip v2 BC.

Figure 6:
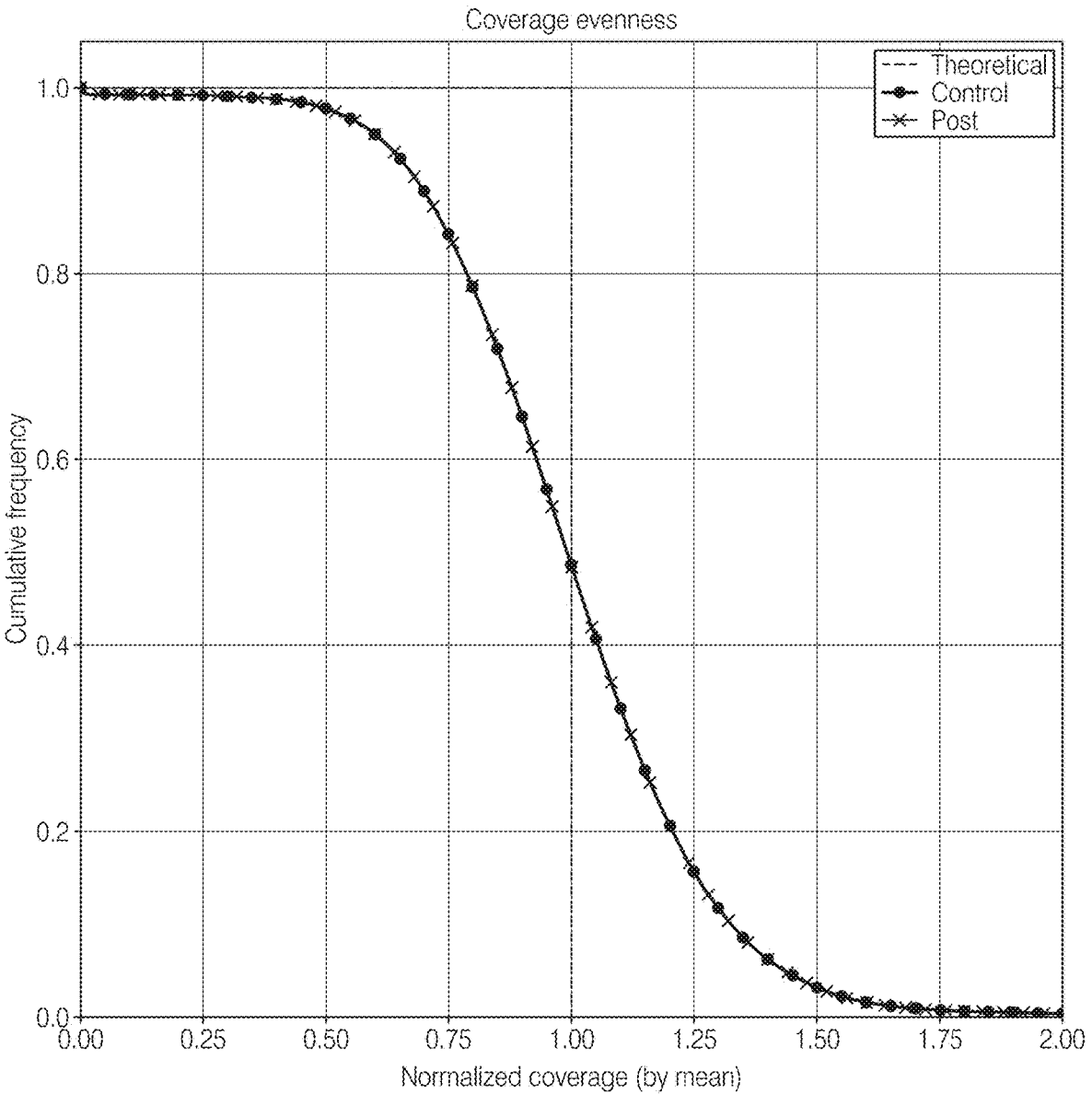
FIG. 6 shows *Escherichia coli* genome sequence coverage evenness obtained by sequencing libraries prepared in the presence ("Post" or absence ("Control") of ComEA2 nucleic acid binding domain. Coverage evenness was calculated as described in Oexle K et al., *J Hum Genet.* 61(7): 627-32 (2016). Note that at most points, the Control and Post curves appear to be a single curve, as these curves overlapped, and both of these curves generally overlapped with the theoretical predicted curve.

Sequencing data analysis revealed that ComEA2 interactions with DNA are sequence non-specific. *Escherichia coli* genome coverages obtained by sequencing PCR-free libraries constructed in the presence ("Post") or absence ("Control") of ComEA2 nucleic acid binding domain were highly similar (FIG. 6).

Example 7: Identification and Testing of Nucleic Acid Binding Domains

Homologous domain search was performed using PSI-BLAST iterative search tool (Altschul et al., 1997) with ComEA2 domain sequence used as input. Search was performed against the domain database of bacteria with maximum target sequences set to 1000. Eleven most promising candidates among the identified domains (domain sequence similarity 31-67%) were selected depending on the living conditions of the host organism.

Domains for testing had an N-terminal 6-His tag (SEQ ID NO: 131) and a site for in vivo biotinylation.

A nucleic acid binding domain was assessed for the ability to capture DNA in enzymatic reaction mixture. Further, it was assessed whether the ends of captured nucleic acid fragments were then accessible for DNA-modifying enzymes and be eluted in mild heat.

500 ng of 260 base pair (bp) double-stranded DNA fragment in Dilution Buffer (10 mM Tris-HCl, pH 8.0, 300 mM NaCl) was used as an input and in vivo biotinylated ComEA15 (SEQ ID No: 15) nucleic acid binding domain immobilized on streptavidin-coated magnetic beads was used as the interaction partner, binding was performed at room temperature (25° C.) for 10 minutes. Then the DNA fragment was blunted and dA-tailed following standard DNA end conversion protocol in 50 μL of 1× End Conversion Master Mix (ClaSeek™ NGS Library Preparation Kit, Thermo Scientific, MA, USA). 100 μg of streptavidin-coated magnetic beads with immobilized ComEA15 nucleic acid binding domain and bound DNA were added to the end conversion reaction mixture and incubated at 25° C. for 20 min. Beads were collected on side of the tube using rack magnet, and the supernatant was discarded. Beads were resuspended in 50 μL of 1× Rapid Ligation buffer (Thermo Scientific, MA, USA) containing 35 U of T4 DNA ligase (Thermo Scientific, MA, USA) and 70 pmol of double-stranded synthetic adapters. The ligation reaction was performed for 30 min at room temperature (25° C.). Beads were collected on side of the tube, and supernatant was collected to a separate tube. To elute DNA, beads were resuspended in 25 μL of Dilution Buffer and heated at 80° C. for 20 min. The supernatant was collected to a separate tube. To elute the residual DNA, beads were resuspended in 25 μL of 0.1% SDS and heated at 98° C. for 10 min. The supernatant was collected to a separate tube.

Figure 7:
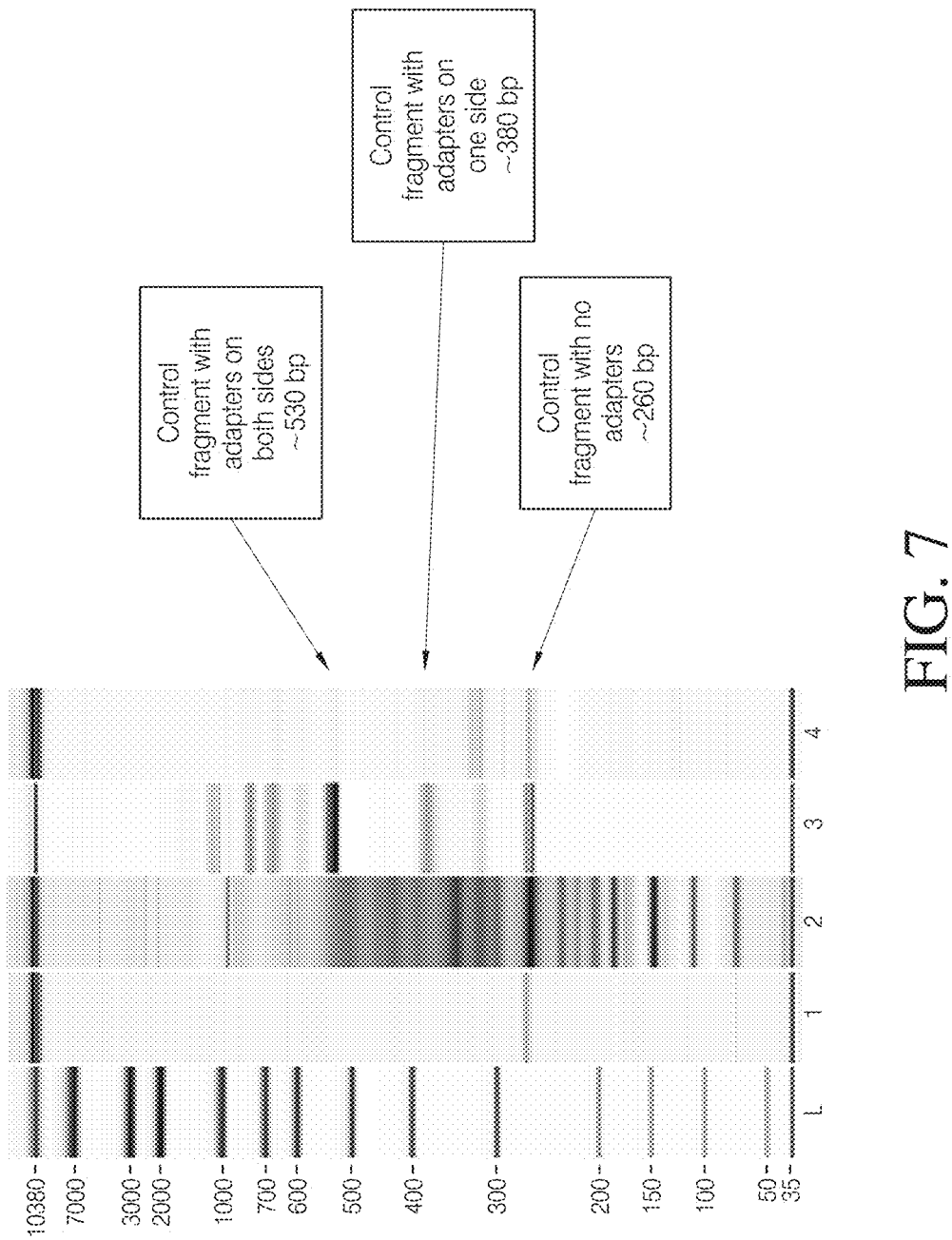
FIG. 7 shows results of binding, enzymatic reaction and elution of 260 bp double-stranded DNA fragment on ComEA15 coated magnetic beads. The DNA size marker was GeneRuler DNA Ladder Mix (Thermo Fisher Scientific, MA, USA). Lane 1 shows unbound DNA fragment. Lane 2 shows purified 1× Rapid Ligation buffer with T4 DNA ligase and double-stranded synthetic adapters after enzymatic reaction. Lane 3 shows sample after elution at 80° C. for 20 minutes. Lane 4 shows additional sample eluted by 0.1% SDS heated at 98° C. for 10 minutes.

All samples were purified using Agencourt AMPure XP (Beckman Coulter, CA, USA) magnetic beads and eluted in 25 μL TE buffer (10 mM Tris-HCl, pH 8.0, 1 mM EDTA) and analyzed using Agilent 2100 Bioanalyzer System and Agilent High Sensitivity DNA Kit (Agilent Technologies, CA, USA). The results are presented in FIG. 7.

Lane "1" is unbound DNA fragment and indicates, that almost all DNA was bound in Dilution Buffer and transferred into down-stream enzymatic reactions. Lane "2" is purified 1× Rapid Ligation buffer with T4 DNA ligase and double-stranded synthetic adapters after enzymatic reaction. It indicates, that a part of the DNA fragment was unbound from the magnetic beads in the reaction mix, but no additional DNA fragments (adapters or adapter dimers) were bound by the beads. Further, lane "3" is elution at 80° C. for 20 min, which shows that not only most of the bound DNA was eluted in these conditions, but most of the eluted DNA was fully converted to a fragment with adapter dimers ligated to both ends. As lane "4", elution in 0.1% SDS and heated at 98° C. for 10 min, shows, almost all DNA was eluted beforehand at 80° C. for 20 min. Thus, DNA bound to streptavidin-coated magnetic beads with immobilized nucleic acid binding domain can undergo enzymatic modification and be eluted in mild heat.

Example 8: Isolation of Nucleic Acid from Electrophoretic Gel

Isolation of nucleic acid from an electrophoretic gel was also assessed.

Figure 8A:
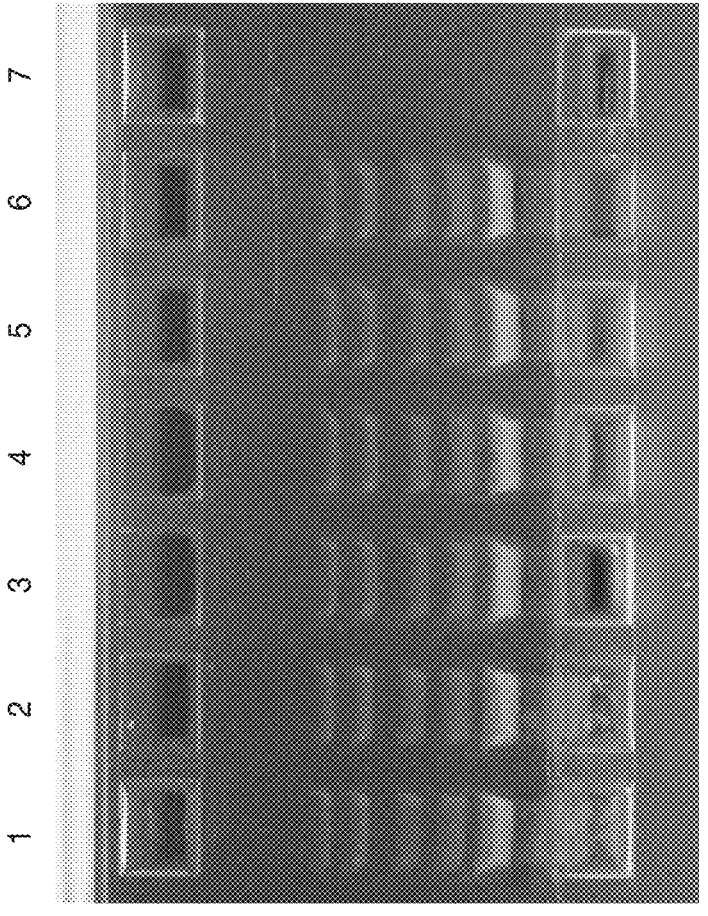

22.5 μL (2.25 μg) of ZipRuler Express DNA Ladder 2 (Thermo Scientific, MA, USA) was used as an input DNA and in vivo biotinylated ComEA15 (SEQ ID No: 15) nucleic acid binding domain immobilized on streptavidin-coated magnetic beads was used as the interaction partner. 22.5 μL of DNA mixed with 2.5 μL of 10× Loading Buffer (Thermo Scientific, MA, USA) was loaded to E-Gel™ CloneWell™ II Agarose Gel (Thermo Scientific, MA, USA) and recovery wells were filled with water according to the manufacturer's protocol and the gel was run until target DNA fragments reached the recovery wells (FIG. 8A). The run was paused and water from recovery wells was collected to a separate tube (run then in lanes 2, 6, 10, 14, and 18 of FIG. 8B).

100 μg of streptavidin-coated magnetic beads with immobilized nucleic acid binding domain was diluted in 1×PBS (137 mM NaCl, 2.7 mM KCl, 10 mM Na$_2$HPO$_4$, 1.8 mM KH$_2$PO$_4$, pH 7.4) up to 40 μL and loaded into recovery well. The E-gel was then run until all target DNA fragment entered the recovery well. After electrophoresis, magnetic beads were resuspended in the recovery well and collected to a separate tube. The tube with magnetic beads was transferred to a magnetic stand. After the beads settled, the supernatant was collected into a separate tube (lanes 3, 7, 11, 15, and 19 of FIG. 8B).

To elute the DNA, the beads were resuspended in 10 μL of 1×PBS and heated at 80° C. for 20 min. The tube with magnetic beads was transferred to a magnetic stand. After the beads settled, the supernatant was collected into a separate tube (lanes 4, 8, 12, 16, and 20 of FIG. 8B). To elute any residual DNA beads still bound after incubation at 80° C., magnetic beads were resuspended in 10 μL of 0.1% SDS and heated at 98° C. for 10 min. The tube with magnetic beads was transferred to a magnetic stand. After the beads settled the supernatant was collected to a separate tube (lanes 5, 9, 13, 17, and 21 of FIG. 8B). All collected samples were analysed on agarose gel.

Figure 8B:
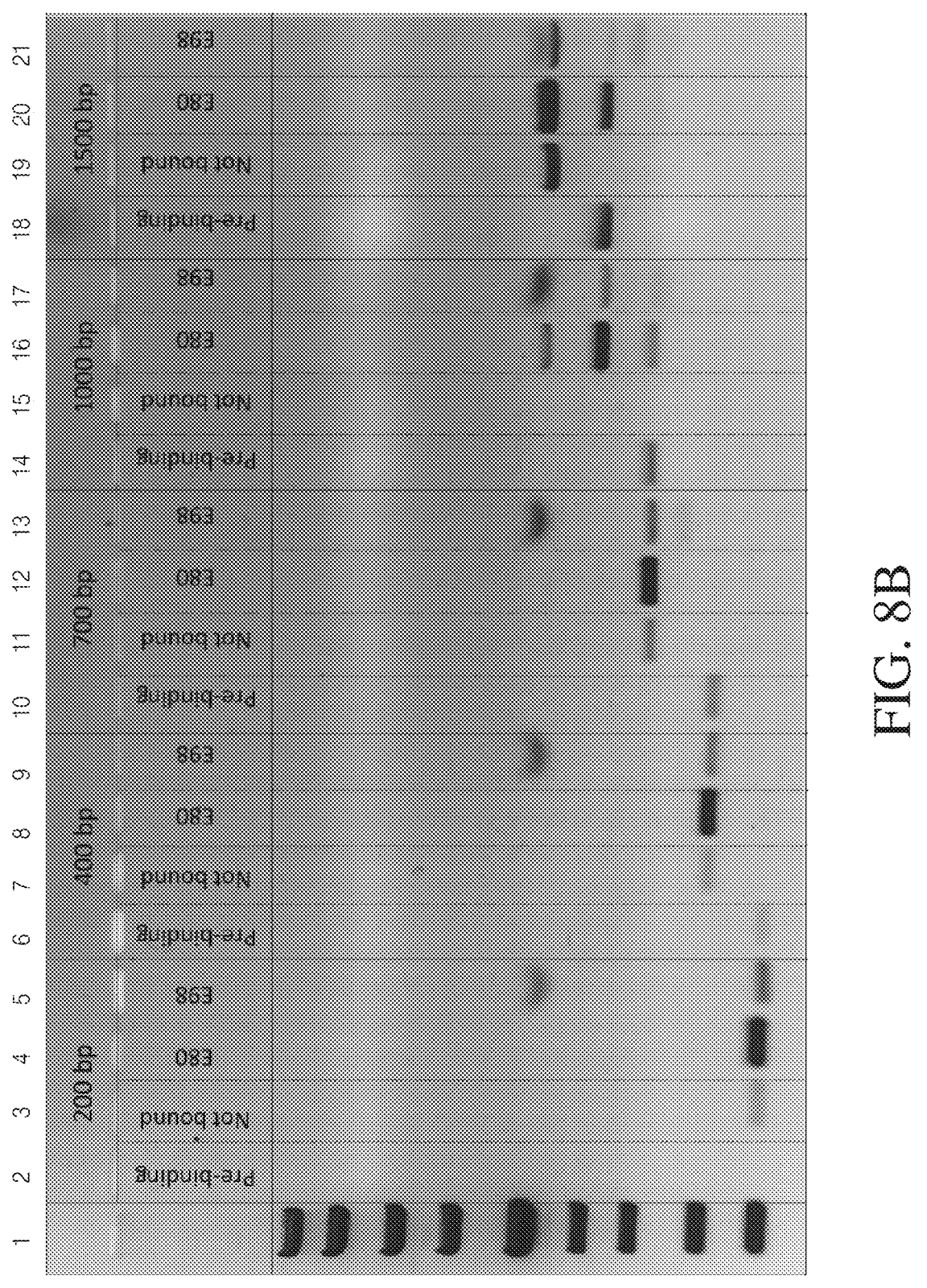

As can be seen from FIG. 8B, use of ComEA15 nucleic acid binding domain immobilized on magnetic beads allowed isolation of nucleic acid from electrophoretic gel. Analogous results were achieved when DDE_Tnp1_assoc8 nucleic acid binding domain was used. Thus, ComEA or DDE_Tnp1_assoc nucleic acid binding domains bound to solid matrix (e.g. particles or magnetic beads) may be used for isolation of nucleic acids where the sample comprising nucleic acids has been run through an electrophoretic gel. Depending on chosen time of running the electrophoresis, once the nucleic acid binding domains bound to solid matrix have been loaded, the nucleic acid binding domains may bind nucleic acid of selected specific length (e.g. when electrophoresis is run for a period of time during which the nucleic acid of selected specific length enters recovery well from the gel) or they may bind to a range of nucleic acids of different sizes (e.g. when electrophoresis is run for a period of time during which a range of nucleic acids of different sizes enter the recovery well from the gel).

As can be seen from Examples 7 and 8, DNA is eluted in a solution with the same or similar salt concentration as was used for DNA binding, by incubating DNA bound to nucleic acid binding domain at elevated temperature for a time period.

Example 9: Binding Properties of Mutant ComEA15 Nucleic Acid Binding Domains

Using the analysis and selection method as described in Porebski B T, Buckle A M. *Protein Eng Des Sel.* 2016; 29(7):245-51, the closest 500 homologous proteins were aligned and candidate positions for mutations as well as candidate substitutions at those positions were selected, that could have destabilizing effect to the nucleic acid binding domain.

A ComEA15 K55R nucleic acid binding domain (having a K55R amino acid substitution in SEQ ID NO: 15) was assessed for the ability to release DNA at lower temperature compared to the non-mutated ComEA15 domain. This ComEA15 K55R comprises a motif of SEQ ID NO: 124.

1500 ng of GeneRuler DNA Ladder Mix (Thermo Scientific, MA, USA) in 1×PBS (137 mM NaCl, 2.7 mM KCl, 10 mM $Na_2HPO_4$, 1.8 mM $KH_2PO_4$, pH 7.4) to 30 μl was used as input DNA (Lane 1, FIG. 9) and in vivo biotinylated ComEA15 K55R nucleic acid binding domain immobilized on streptavidin-coated magnetic beads was used as the interaction partner. 300 μg of streptavidin-coated magnetic beads with immobilized ComEA15 K55R nucleic acid binding domain were added to DNA diluted in 1×PBS and incubated at room temperature (25° C.) for 30 minutes. Beads were collected on the side of the tube using a rack magnet, and the supernatant (lane 2, FIG. 9) was collected into a separate tube.

Beads were then resuspended in 30 μL of 1×PBS. Beads were collected on side of the tube, and supernatant (lane 3, FIG. 9) was collected to a separate tube. To elute DNA, beads were resuspended in 30 μL 1×PBS and separate aliquots were heated at 65° C., 75° C. or 80° C. for 10 min. The supernatant was collected to separate tubes (lanes 4, 6, and 8, FIG. 9, respectively). To elute the residual DNA, beads were resuspended in 10 μL of 0.1% SDS and heated at 98° C. for 10 min. The supernatant (lanes 5, 7, and 9, FIG. 9) was collected to a separate tube.

2 μl of MassRuler DNA Loading Dye (Thermo Scientific, MA, USA) was added to each sample and 10 μL of all samples were analysed in 1% TAE+ethidium bromide (EtBr) agarose gel.

Figure 9:
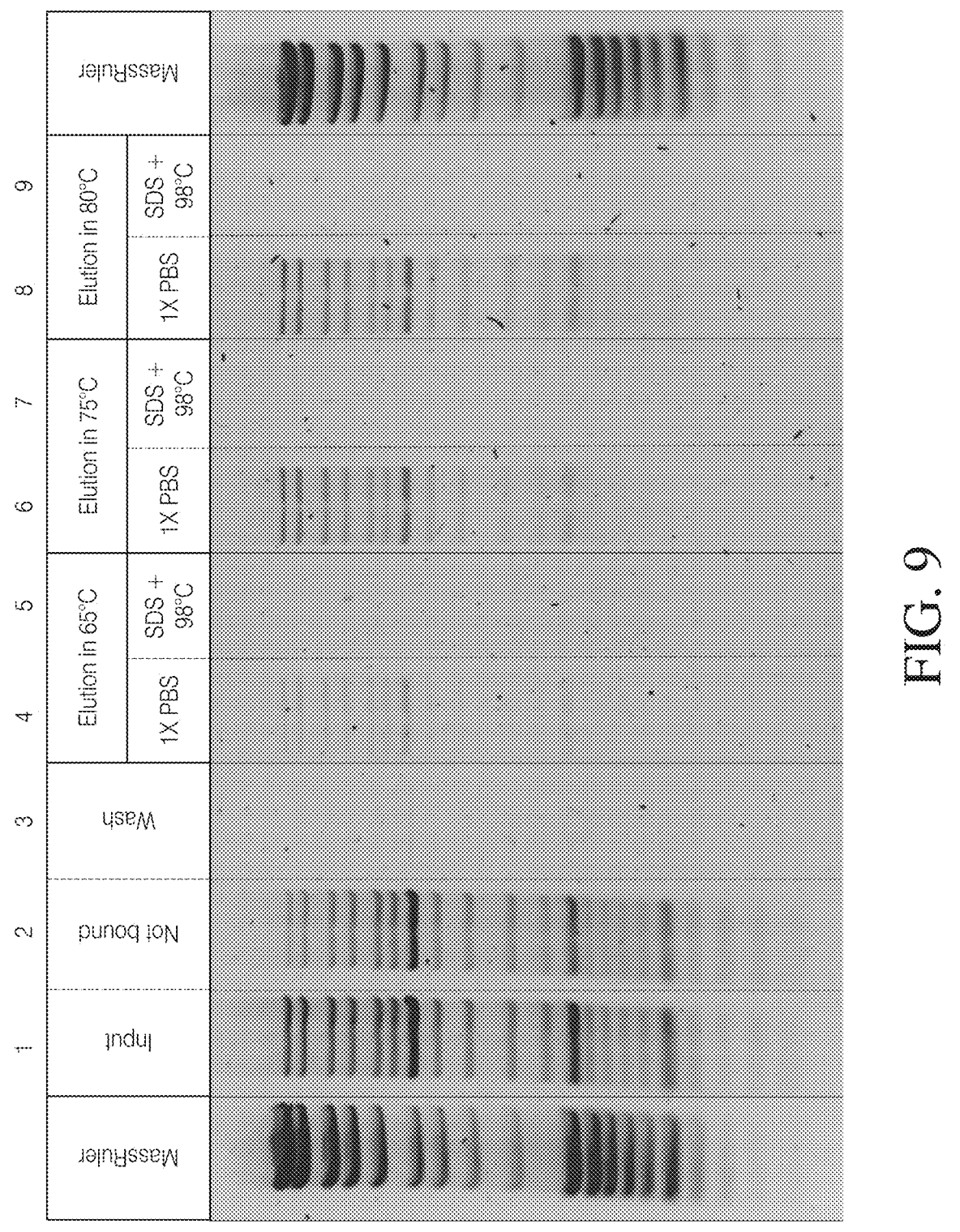

As can be seen from FIG. 9, DNA bound by ComEA15 K55R can be eluted already at 65° C., thus ComEA15 K55R mutant releases DNA at lower temperature than the non-mutated ComEA15 nucleic acid binding domain, when a solution with the same or similar salt concentration is used for DNA binding and elution.

Similar results of improved thermolability compared to non-mutated domain were observed with ComEA15 I52F mutant (comprising SEQ ID NO: 125) and ComEA9 A31N mutant (comprising SEQ ID NO: 126) (data not shown).

Example 10: Elution Properties of Mutant ComEA15 Nucleic Acid Binding Domains A ComEA15 K55R nucleic acid binding domain (having a K55R amino acid substitution in SEQ ID NO: 15) was assessed for the ability to release DNA at lower salt concentration compared to the non-mutated ComEA15 domain.

1500 ng of GeneRuler Low Range DNA Ladder (Thermo Scientific, MA, USA) in binding buffer (50 mM NaCl, 10 mM Tris-HCl, pH 7.6, 0.01% Tween-20) to 60 μl was used as input DNA (Lane 1, FIG. 10) and in vivo biotinylated ComEA15 K55R nucleic acid binding domain immobilized on streptavidin-coated magnetic beads was used as the interaction partner. 1200 μg of streptavidin-coated magnetic beads with immobilized ComEA15 K55R nucleic acid binding domain were added to DNA diluted in binding buffer and incubated at room temperature (25° C.) for 10 min and divided into 3 separate 1.5 ml tubes. Beads were collected on side of the tube using rack magnet, and the supernatant (lanes 2, 5 and 8, FIG. 10, respectively) was collected to a separate tube. Beads were resuspended in 20 μL of either Water, nuclease-free (Thermo Scientific, MA, USA), Elution Buffer (10 mM Tris-HCl, pH 8.5), or binding buffer and incubated at room temperature (25° C.) for 2 min. Beads were collected on side of the tube, and supernatant (lanes 3, 6 and 9 FIG. 10, respectively) was collected to a separate tube. To elute DNA, beads were resuspended in 20 μL either Water, nuclease-free (Thermo Scientific, MA, USA), Elution Buffer (10 mM Tris-HCl, pH 8.5), or binding buffer accordingly and heated at 60° C. for 10 min. The supernatant was collected to separate tubes (lanes 4, 7, 10, FIG. 10, respectively).

4 μl of MassRuler DNA Loading Dye (Thermo Scientific, MA, USA) was added to each sample and 12 μL of all samples were analysed in 3% TAE+EtBr agarose gel.

Figure 10:
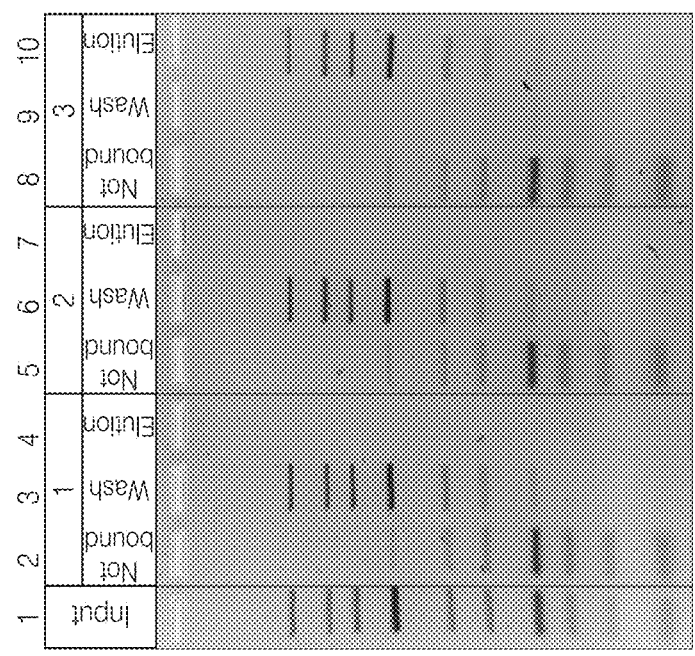
FIG. 10 shows results of binding and elution of GeneRuler Low Range DNA Ladder on ComEA15 K55R coated magnetic beads. Section 1 is sample where both Wash and Elution steps were performed with Water, nuclease-free; Section 2 is sample where both Wash and Elution steps were performed with Elution Buffer; Section 3 is sample where both Wash and Elution steps were performed with binding buffer.

As can be seen from FIG. 10, DNA bound by ComEA15 K55R can be eluted already at room temperature (25° C.) with Water, nuclease-free (Thermo Scientific, MA, USA), or Elution Buffer (10 mM Tris-HCl, pH 8.5). ComEA15 K55R mutant is able to release DNA when smaller amounts of salt or no salts are present in the elution solution (as compared with the binding solution), while incubation temperature is the same as compared with temperature during binding.

Corresponding results (i.e. DNA release in elution solution having lower salt or no salt, as compared with the binding solution, while incubation temperature is the same as compared with temperature during DNA binding) were observed with other mutant nucleic acid binding domains: ComeA15 T10K, ComeA15 L16F, ComeA15 S20K, ComeA15 A27T, ComeA15 S41N, ComeA15 D44G, ComeA15 E54Q, ComeA15 D44Y, ComeA15 I52F, ComeA15 D45Q, ComeA15 S41R, ComeA15 E54A, ComeA15 T56I, ComEA2 R29H (data not shown).

Example 11: Binding Properties of DDE_Tnp1_Assoc8 Nucleic Acid Binding Domains A DDE_Tnp1_assoc8 nucleic acid binding domain was assessed for the ability to bind and release DNA at different NaCl concentrations and pH.

500 ng of GeneRuler 100 bp Plus DNA Ladder (Thermo Scientific, MA, USA) in 10 μl of buffer (10 mM Tris-HCl, pH 8.0) was used as input DNA (Lane 1, FIG. 11A) and in vivo biotinylated nucleic acid binding domain immobilized on streptavidin-coated magnetic beads was used as the interaction partner. 100 μg of streptavidin-coated magnetic beads with immobilized DDE_Tnp1_assoc8 nucleic acid binding domain were added to DNA solution, and the mixture was incubated at room temperature (25° C.) for 30 min. Beads were collected on side of the tube using rack magnet, and the supernatant (lane 2, FIG. 11A) was collected to a separate tube. Beads were resuspended in 10 μL of the buffer of the same composition. Beads were collected on side of the tube, and supernatant (lane 3, FIGS. 11A and 11B) was collected to a separate tube. To elute DNA, beads were resuspended in 10 μL of the buffer of the same composition and heated at 80° C. for 20 min. The supernatant was collected to a separate tube (lane 4, FIGS. 11A and 11B). To elute the residual DNA, beads were resuspended in 10 μL of 0.1% SDS and heated at 98° C. for 10 min. The supernatant (lane 5, FIGS. 11A and 11B) was collected to a separate tube. Analogous experiments were performed using different buffers (pH 8.0 and pH 7.6 and 0, 50, 100, 200, 300, and 500 mM NaCl, respectively).

2 μl of 6×DNA Loading Dye (Thermo Scientific, MA, USA) was added to each sample and 10 μL of all samples were analysed in 1% TAE+EtBr agarose gel.

Figure 11A:
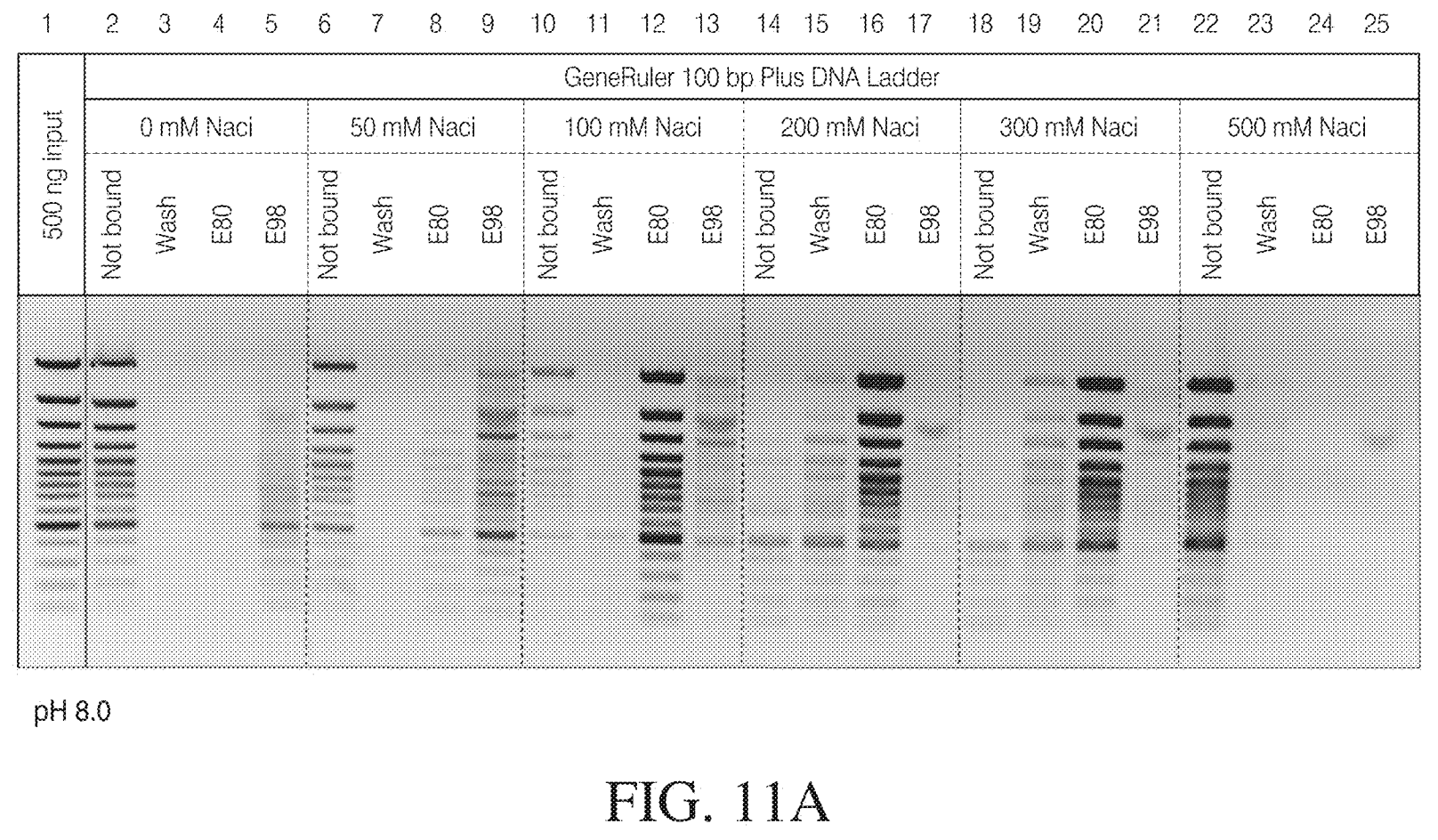
Figure 11B:
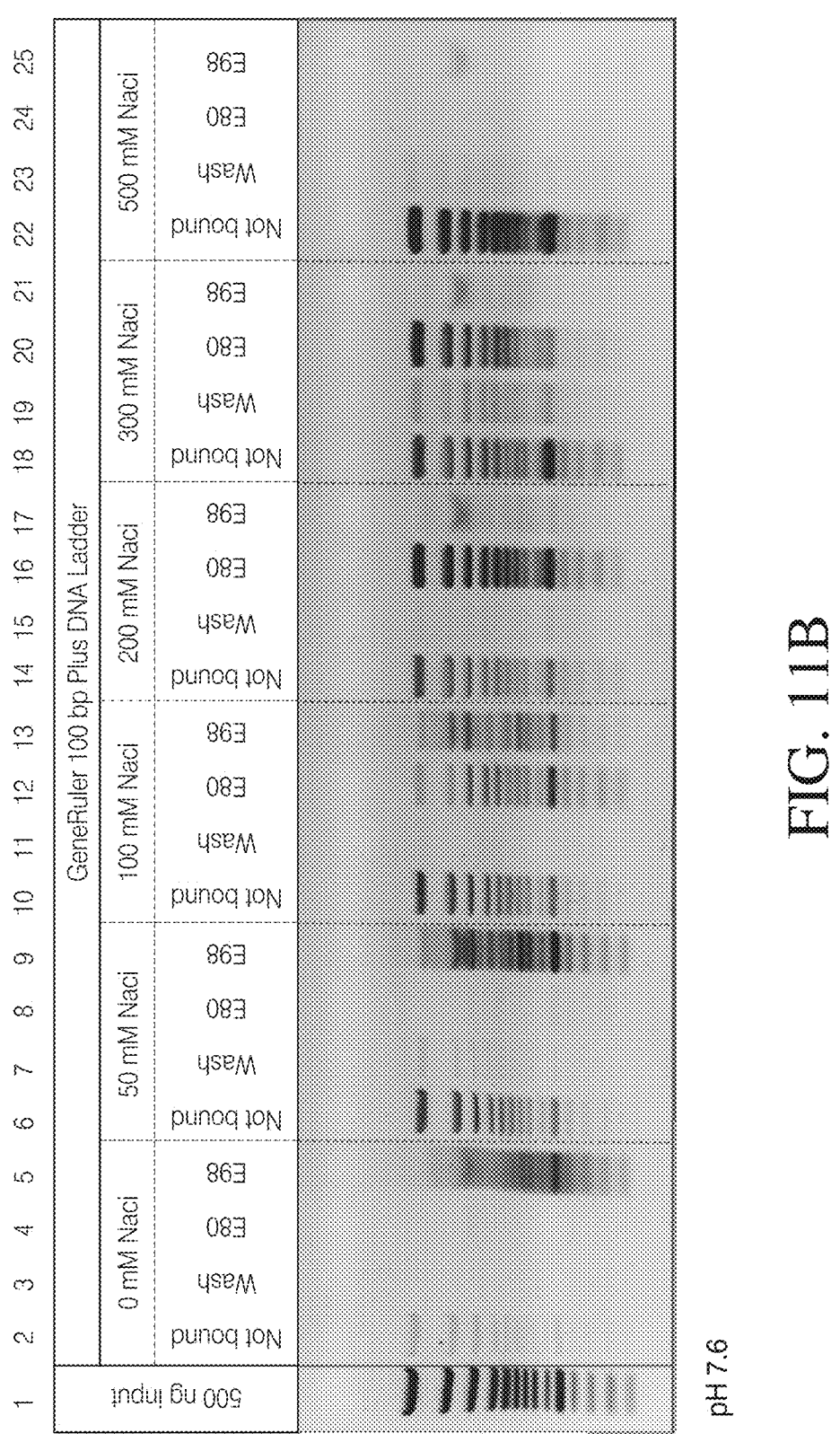

DNA is bound by DDE_Tnp1_assoc8 over a range of salt concentration and at both, pH 7.6 (FIG. 11B) and pH 8.0 (FIG. 11A). It can be observed that DNA is bound at 25° C. and released at 80° C. when using a solution with NaCl from 100 mM to 300 mM. Experiments in different pH show, that several pH values can be used, without changing the results. Only a portion of DNA is bound in solution with 50 mM NaCl, and even smaller portion of DNA is bound in solution with 0 mM NaCl, while in these cases, in order to elute the DNA, a higher temperature of 98° C. as well as SDS as destabilizer of proteins.

ComEA domains from ComEA5 to ComEA15, also were able to bind DNA in the presence of 50 mM NaCl up to 700 mM NaCl (data not shown).

Example 12: dsRNA Binding Properties of DDE_Tnp1_Assoc Protein

A DDE_Tnp1_assoc8 nucleic acid binding domain (SEQ ID NO: 23) was assessed for the ability to bind dsRNA.

500 ng of phi6 dsRNA (Thermo Scientific, MA, USA) in 1×PBS (137 mM NaCl, 2.7 mM KCL, 10 mM Na2HPO4, 1.8 mM KH2PO4, pH 7.4) or TE buffer (10 mM Tris-HCl, pH 8.0, 1 mM EDTA) to 20 µl was used as input dsRNA and in vivo biotinylated DDE_Tnp1_assoc8 nucleic acid binding domain immobilized on streptavidin-coated magnetic beads was used as the interaction partner. 100 µg of streptavidin-coated magnetic beads with immobilized DDE_Tnp1_assoc8 nucleic acid binding domain were added to dsRNA diluted in 1×PBS or TE buffer and incubated at room temperature (25°) for 30 min. Beads were collected on side of the tube using rack magnet, and the supernatant was collected to a separate tube. Beads were resuspended in 20 µL of 1×PBS. Beads were collected on side of the tube, and supernatant was collected to a separate tube. To elute dsRNA, beads were resuspended in 20 µL of 0.1% SDS and heated at 98° C. for 10 min. The supernatant was collected to a separate tube.

4 µl of 6×DNA Loading Dye (Thermo Scientific, MA, USA) was added to each sample and 12 µL of all samples were analysed in 1% TAE+EtBr agarose gel.

Figure 14:
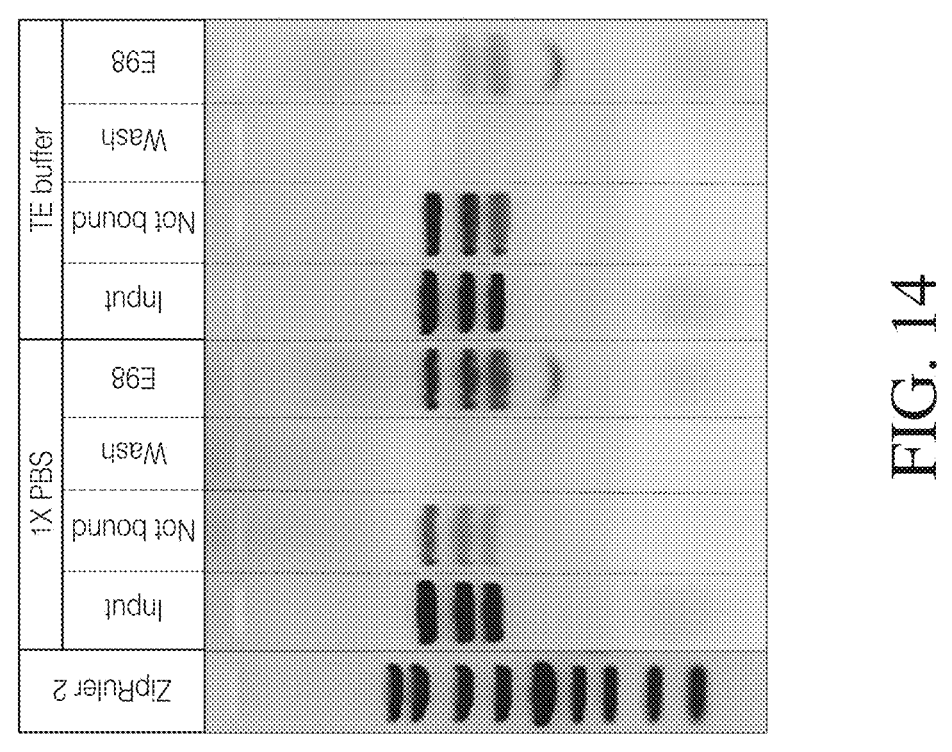

As can be seen from FIG. 14, DDE_Tnp1_assoc8 binds dsRNA in both 1×PBS and TE buffer and dsRNA fragments of all lengths are bound equally.

Example 13: DNase I Immobilization on Solid Surface

Fresh beads coated with DNase I were prepared as follows. 80 µL of 10 µg/µL (800 µg) magnetic Dynabeads Streptavidin C1 beads (Invitrogen, Cat. No. 65002) were washed 3 times in 1×, LISCA buffer (Low Ionic Strength with Calcium: 50 mM Tris-HCl, pH 7.6, 10 mM CaCl2)). After last wash, supernatant was removed and 10 µL of various dilutions of DNase I with an N-terminal tag (SEQ ID NO: 130) (0.1 ng/µL, 1 ng/µL, 10 ng/µL and 100 ng/µL; respectively, 1 ng, 10 ng, 100 ng and 1000 ng of DNase I) were added in the presence of 70 µL 1×LISCA buffer. After 30 min of incubation at room temperature supernatant was removed and subsequently washed in 1×LISCA+0.1% BSA+0.01% Tween 20 three times, and then beads were washed 3 times using 1×LISCA+0.01% Tween 20. After last wash supernatant was removed. A DNase I-free bead control was prepared by following all the washing procedures, except DNase I binding step was skipped.

Figure 15:
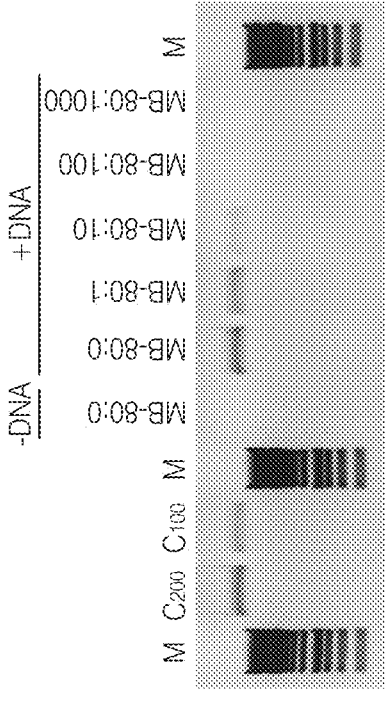
FIG. 15 shows results of DNA degradation by bead-bound DNase I. Increased amounts of DNase I degrade 200 ng of DNA into traces that are undetectable on agarose gel. M—GeneRuler 1 kb DNA Ladder (Thermo Scientific, Cat. No. SM0311). C200 and C100—controls for undigested Lambda genomic DNA, respectively, 200 and 100 ng. –DNA and +DNA blocks show whether DNA was present in the sample. MB:80:0—beads containing no immobilized DNAse I. MB:80:1—beads containing 1 ng of DNase I per 800 μg of beads. MB:80:10—beads containing 10 ng of DNase I per 800 μg of beads. MB:80:100—beads containing 100 ng of DNase I per 800 μg of beads. MB:80:1000—beads containing 1000 ng of DNase I per 800 μg of beads.

The ability of immobilized DNase I to digest nucleic acid was tested by fragmenting genomic Lambda DNA. 10 ng/µL Lambda DNA in 1×DNase I buffer with $Mn^{2+}$ ions was prepared (10 mM Tris-HCl, pH 7.5, 10 mM $MnCl_2$, 0.1 mM $CaCl_2$)). 20 µL of this DNA solution (200 ng) was added directly on 10 µL dry (storage buffer removed) DNase I-coated beads, resuspended and incubated at 37° C. for 10 minutes. Genomic DNA-free control and bead control without DNase I were included, too. After incubation, 10 µL of supernatant from each reaction was taken and combined with 5 µL of 0.5 M EDTA and 3 µL of 6× Loading Dye (Thermo Scientific, Cat. No. R0611) and analyzed on 1% TAE agarose gel with 0.5 µg/mL ethidium bromide, along with 200 ng and 100 ng Lambda DNA. As can be seen from FIG. 15, DNase I after immobilization on solid surface remains active. 200 ng of DNA is completely degraded after 10 minutes by MB-80:100 beads (100 ng DNase I per 80 µL (800 µg) of beads).

Example 14: ComEA2 and DNase I Co-Immobilization on Solid Surface

To choose a suitable DNase I density on bead we prepared beads starting with 80 µL of 10 µg/µL (800 µg) magnetic Streptavidin C1 beads, triple-washed in 1×LISCA (50 mM Tris-HCl, pH 7.6, 10 mM $CaCl_2$)+0.01% Tween 20. Supernatant was removed. Different DNase I densities (500 ng, 1000 ng and 2000 ng) were obtained by adding 5 µL, 10 µL and 20 µL of 100 ng/µL DNase I dilution to the beads. 1×LISCA buffer was added to the total volume of 80 µL. After 30 min of incubation at room temperature supernatant was removed and subsequently washed in 1×LISCA+0.1% BSA+0.01% Tween 20 three times, after which, triple-washed using 1×LISCA+0.01% Tween 20. Supernatant was removed. 80 µL of DNA binding domain ComEA2 (SEQ ID NO: 2; 0.28 mg/mL, 22.4 µg total) was added to beads and resuspended (for DNase I-only control set of beads, this step was not performed and proceeded directly to bead washing). After 30 min of incubation at room temperature supernatant was removed and beads were subsequently washed in 1×LISCA+0.1% BSA+0.01% Tween 20 three times, after which, triple-washed using 1×LISCA+0.01% Tween 20. Afterwards, beads were resuspended by adding 75 µL of 1×LISCA+0.01% Tween 20, which resulted in ~80 µL final volume of each beads.

Figure 16:
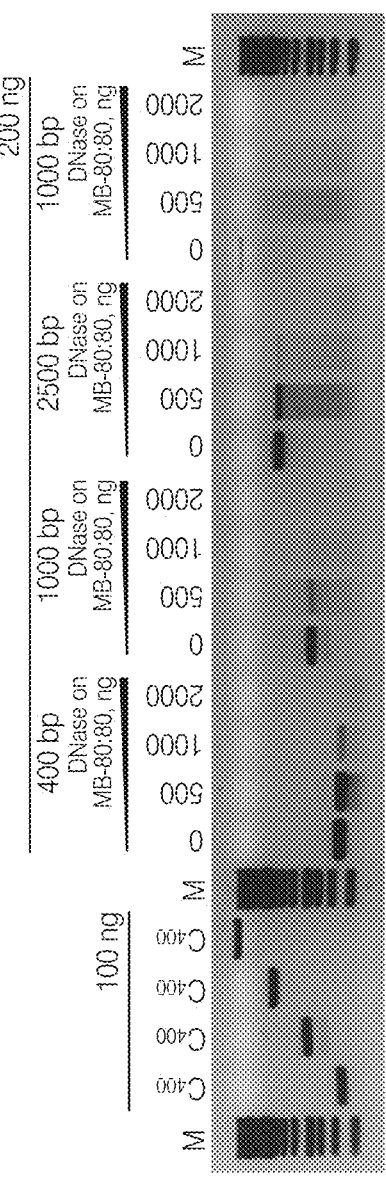
FIG. 16 shows binding and on-bead digestion of DNA fragments of various length on DNase I and ComEA2 co-immobilized beads. Initial DNA fragment size does not have an effect to a final sheared DNA profile and final fragmented DNA profile can be adjusted by increasing or decreasing DNase I density. M—GeneRuler 1 kb DNA Ladder (Thermo Scientific, Cat. No. SM0311). C400, C1000, C2500 and C10000—controls for undigested NoLimits DNA fragments, respectively, 400, 1000, 2500 and 10000 bp in size. 400 bp, 1000 bp, 2500 bp and 10000 bp blocks show which DNA fragment was used in the reaction. MB:80:80—beads containing 80 μL (22.4 μg) of ComEA2 protein per 80 μL (800 μg) of beads. 0, 500, 1000 and 2000—DNase I amount in nanograms on MB-80:80 beads.

To test whether the system can yield constant fragmented DNA size, regardless the input DNA size, four NoLimits DNA fragments (Thermo Scientific, Cat No. SM1631, SM1671, SM1571 and SM1751, respectively) were used for binding and fragmentation on beads. 20 ng/µL No Limits DNA fragments (400 bp, 100 bp, 2500 bp, 10000 bp, respectively) were prepared in 1×DNase I buffer+$Mn^{2+}$ (10 mM Tris-HCl, pH 7.5, 10 mM $MnCl_2$, 0.1 mM $CaCl_2$)). 20 µl of these DNA solutions was added directly on 20 µL dry (storage buffer removed) beads (DNA binding performed in saturated conditions, where 400 ng of DNA was loaded, and capacity of the beads was ~200 ng), resuspended and incubated at 37° C. for 10 minutes. After incubation, 5 µL of 0.5 M EDTA was added to stop the reaction, mixed thoroughly. 25 µL of reaction supernatant was discarded. Beads were washed with 25 µL of 1×DNase I reaction buffer with 50 mM EDTA and supernatant discarded. Finally, 25 µL of Elution buffer 1(EB1) composed of 1.2 mM Tris-HCl, pH 8.5; 14.8% DMSO; 1.3% SDS; 1023 mM Urea; 0.6 mg/mL Proteinase K; 1.6 mM $CaCl_2$ was used to elute DNA from beads at 72° C. for 15 minutes. Eluate was cleaned up using GeneJET Gel Extraction and DNA Cleanup Micro Kit (Thermo Scientific, Cat. No. K0832), protocol A, eluted in 25 µL of elution buffer from the kit and samples, in parallel with corresponding standards (10 µL sample+2 µL 6× dye, 10 µL on the gel) were analyzed on 1% TAE agarose. As can be seen from FIG. 16, at each DNase I density DNA is degraded to the same shear profile and by adding less or more DNase I it is possible to control the sheared DNA profile. This method is also beneficial in view of the possibility to use a buffer with manganese (II) ions—the DNase I generates blunt ends on fragmented DNA molecules under these conditions. However, $Mn^{2+}$ ions may affect the performance of other enzymes such as polymerases in downstream applications, thus the possibility to remove the DNase I reaction buffer comprising $Mn^{2+}$, is very useful, as a very different buffer can then be provided for a downstream enzymatic reaction.

Figure 17:
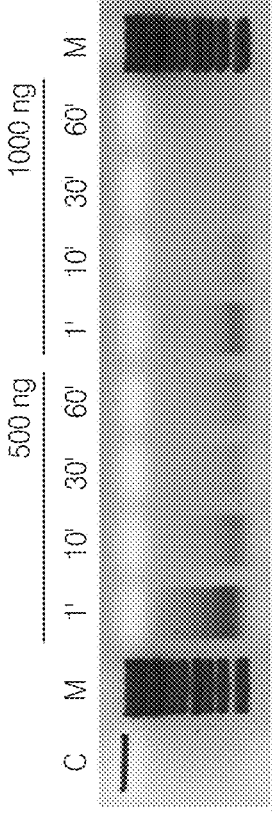
FIG. 17 shows binding and on-bead digestion of DNA fragment for various times. A 10000 bp NoLimits DNA fragment was digested by the same beads with the same ComEA2 and DNase I density for various duration. M—GeneRuler 1 kb DNA Ladder (Thermo Scientific, Cat. No. SM0311). C—control for undigested 10000 bp NoLimits DNA fragment. 500 ng shows that 500 ng of DNase I was used per MB:80:80 beads (containing 80 μL (22.4 μg) of ComEA2 protein per 80 μL (800 μg) of beads).

Example 15: ComEA2 and DNase I System Reaches Equilibrium and Normalizes Fragment Size 10 mg/mL beads with 500 ng of DNase I per 800 µg of beads and then saturated with 22.4 µg of ComEA2 were used to test whether prolonged incubation times affect fragment length. 20 µL of beads were used to fragment 200 ng of 10000 bp NoLimits DNA fragment (Thermo Scientific, Cat No. SM1751) and reaction was carried out in 1×DNase I buffer+$Mn^{2+}$ (10 mM Tris-HCl, pH 7.5, 10 mM $MnCl_2$, 0.1 mM $CaCl_2$)). Reactions were carried out for 1, 10, 30 and 60 minutes at 37° C. temperature. After incubation, 5 µL of 0.5 M EDTA was added and mixed thoroughly to stop the reaction. Supernatant was discarded and beads were washed with 25 µL of 1×DNase I reaction buffer with 50 mM EDTA and eluted using 25 µL of EB1 buffer at 72° C. for 15 minutes. Eluate was cleaned up using GeneJET Gel Extraction and DNA Cleanup Micro Kit, protocol A, eluted in 25 µL of elution buffer from the kit and along with an undigested 10000 bp NoLimits DNA fragment control were analyzed on 1% TAE agarose gel (10 µL sample+2 µL 6× Loading Dye, 10 µL on the gel). As can be seen from FIG. 17, the reaction reaches plateau in about 30 minutes, after which the fragmentation stops and insert size does not get shorter than 250 bp, the lowest marker (M) band. We observed that DNA fragment size stops getting shorter after about 30 minutes, which suggests, that immobilized DNase I and DNA which is bound to the beads have limited movement, therefore reaction comes to a halt, where fragment size does not change anymore.

Figure 18A:
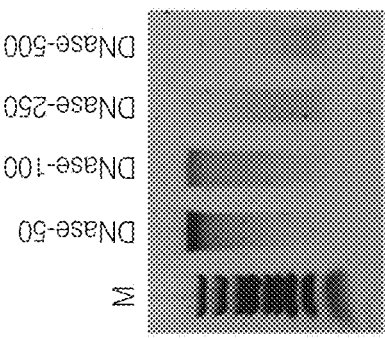
FIGS. 18A-B show fragmented DNA shear profile depends on DNase I density on beads. A) represents electrophoresis results M—GeneRuler Express DNA Ladder (Thermo Scientific, Cat. No. SM1553). DNase-50, -100, -250 and -500—denote an amount of DNase I used per MB:80:80 beads (containing 80 μL (22.4 μg) of ComEA2 protein per 80 μL (800 μg) of beads). B) shows sheared DNA profile as visualized using TotalLAB software. DNase-50, -100, -250 and -500—denote an amount of DNase I used per MB:80:80 beads (containing 80 μL (22.4 μg) of ComEA2 protein per 80 μL (800 μg) of beads). Y axis in the graph represent intensity, while X axis denote a DNA fragment length, calculated from GeneRuler Express DNA Ladder.
Figure 18B:
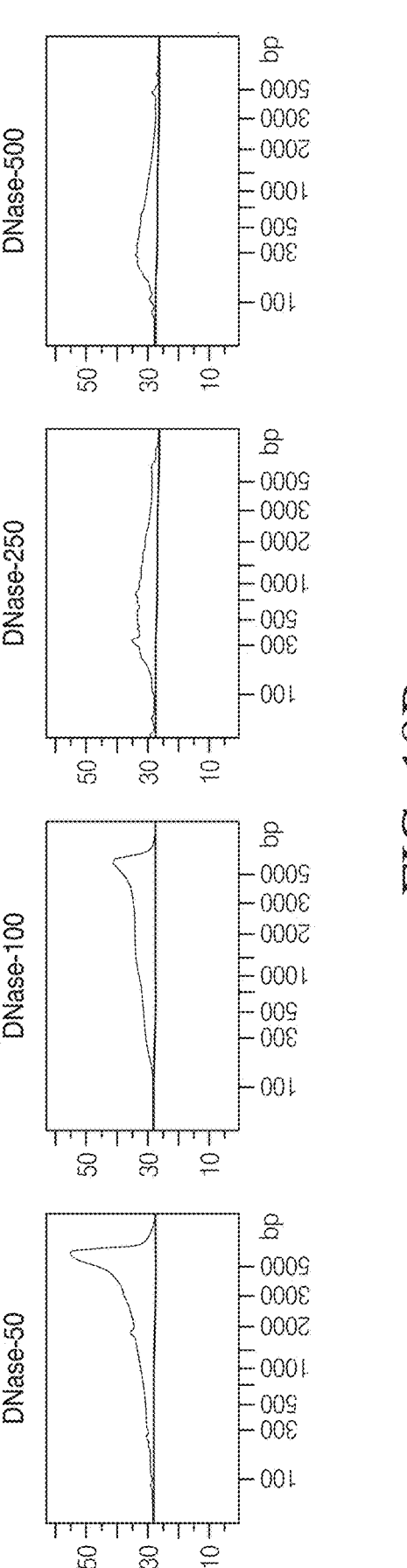

Example 16: DNase I Density on the Bead Surface Determines the Final Length of DNA Fragments 10 mg/mL beads with various DNase I densities (50, 100, 250 and 500 ng per 800 µg of beads) and ComEA2 were prepared as described before. Fragmentation of a 10000 bp NoLimits DNA fragment was performed for 30 minutes to test whether fragment length depends on DNAse I density on the bead. 20 µL of 20 ng/µL (400 ng) 10000 bp NoLimits in 1×DNase I buffer+$Mn^{2+}$ was added directly on 20 µL dry (storage buffer removed) beads (DNA binding performed in saturated conditions, where 400 ng of DNA was loaded, and capacity of the beads is ~200 ng), resuspended and incubated at 37° C. for 30 minutes. After incubation, 5 µL of 0.5 M EDTA was added. Supernatant was removed, beads were washed with 25 µL of 1×DNase I reaction buffer with 50 mM EDTA and then eluted in 25 µL of EB1 elution buffer. Elution performed at 72° C. for 15 minutes. Eluates were cleaned up with magnetic bead-based protocol. 50 µL of 96% of ethanol and 50 µL of SeraMag 2 mg/mL beads (Invitrogen) were added to 25 µL of eluate supernatant, kept at room temperature for 15 minutes, then supernatant removed. Beads were washed twice using 85% ethanol, dried and eluted in elution buffer. Samples were then analyzed on 1% TAE agarose gel (10 µL sample+2 µL 6× dye, 10 µL on the gel). As seen from FIG. 18a, there is clear correlation between DNase I density and fragmentation profile—higher DNase I density on beads produces DNA shear of smaller average fragment size, whereas lower DNase I density produces longer DNA fragments. Profiles for fragmented DNA were also visualized using TotalLAB software (FIG. 18b). For an application of next generation sequencing (NGS), an optimal fragment shear profile, with fragments falling in range between 300-1500 bp, is generated when 250 ng of DNAse I is used per 800 µg of beads.

Example 17: ComEA2 and DNase I System Allows for DNA Amount and Fragment Size Normalization A system that is composed of two proteins bound on surface—ComEA2 and DNase I contributes in dual normalization effect—DNA amount normalization (determined the DNA binding domain (i.e. ComEA2) density, which is responsible for the binding capacity of the beads) and the DNA fragment size normalization (determined by DNase I density on the bead surface; less DNase I means they are immobilized more distantly, therefore a fragment bound in between is not digested to any shorter length). To see how this works, multiple libraries were prepared during various sets of experiments and days.

Figure 19:
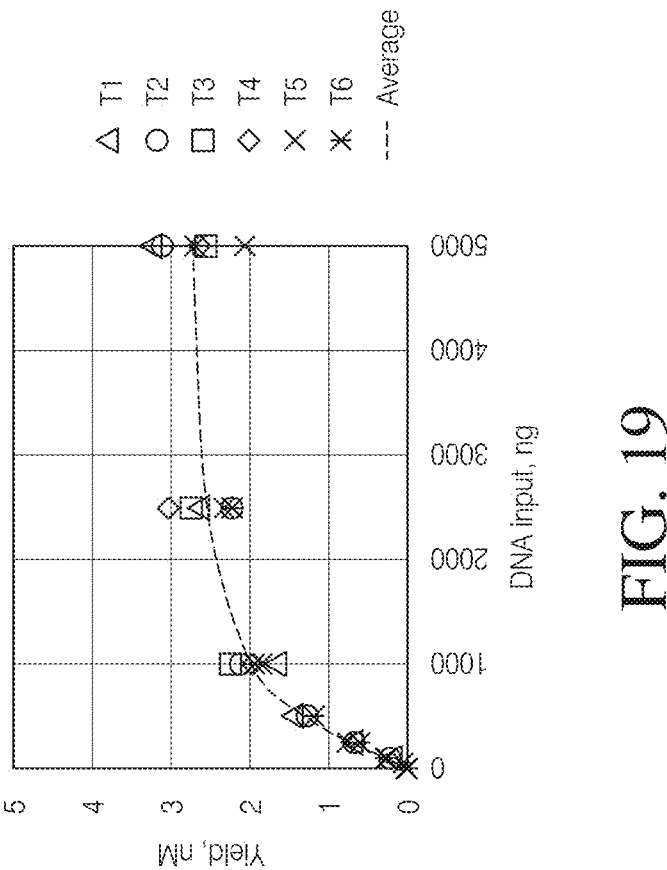
FIG. 19 shows DNA amount normalization for NGS library preparation by using ComEA2 and DNase I co-immobilized on beads system. T1-6 denote experiments done in 1-6 different times. Y axis represents DNA library yield in nanomolar concentration, while X axis denotes a DNA input in nanograms.

10 mg/mL beads with 500 ng DNase I per 800 µg of beads density and 7 µg of ComEA2 were used. For starting material, we used various amounts of 10000 bp NoLimits DNA fragment—10, 50, 100, 250, 500, 1000, 2500, 5000 ng. Multiple (N=6) replicates were prepared per each DNA input. 20 µL of each diluted 10000 bp NoLimits DNA in 1×DNase I buffer+$Mn^{2+}$ was added directly on 20 µL dry (storage buffer removed) beads, resuspended and incubated at 37° C. for 30 minutes. After incubation, 5 µL of 0.5 M EDTA was added. Supernatant was removed, beads were washed with 25 µL of 1×DNase I reaction buffer with 50 mM EDTA and then DNA was eluted from beads in 25 µL of EB1 elution buffer. Elution was performed at 62° C. for 15 minutes (elution of the beads temperature was lowered, after determining it slightly increases yields, data not shown). Eluates were cleaned up with magnetic bead protocol as described before and all DNA was used for a DNA-seq library preparation using Collibri PCR-free PS DNA Library Prep Kit (Invitrogen, Cat. No. A38608024). Size Selection procedure was performed according to a protocol to extract ~350 bp insert-sized DNA libraries. Sequencing libraries were then quantified using qPCR-based Collibri Library Quantification Kit (Invitrogen, Cat. No. A38524100) and concentration values were plotted against a DNA input amount (FIG. 19). Saturation point at about 2000 ng of input DNA and little to none variation between the samples of the same input was observed; that is, DNA library yield normalization occurs at ~2 µg of starting material. Sequencing of such libraries revealed that parameters such as alignment or insert size, all are constant across the wide input range. Thus, the method is robust for DNA amount and fragment size normalization and is suitable as a primary DNA normalization step for NGS applications.

Example 18: Isolation of Cell-Free DNA

40 µL of streptavidin-coated magnetic beads with 400 ng immobilized ComEA10 (SEQ ID NO: 10) nucleic acid binding domain or with ComEA15 K55R mutant nucleic acid binding domain (SEQ ID NO: 15 with a K55R mutation) were added to 1 ml of plasma and incubated at room temperature (25° C.) for 10 minutes. Beads were collected on the side of the tube using a rack magnet, and the supernatant was discarded. Beads were then resuspended in 1 ml of Wash solution (10 mM Tris-HCl, pH 7.6; 200 mM NaCl; 0.01% Tween-20). Beads were collected on side of the tube, and supernatant was discarded. Beads were resuspended in 50 μL of reaction mix (25 μL Elution buffer and 25 μL 2×End Conversion Master Mix) from Collibri™ PS DNA Library Prep Kit for Illumina (Invitrogen) and further procedures were performed according to the protocol up to the ligation of adapters. After adapter ligation, beads were washed 3 times with Wash solution (10 mM Tris-HCl, pH 7.6; 200 mM NaCl; 0.01% Tween-20). Beads were collected on side of the tube, and supernatant was discarded. To elute DNA, beads were resuspended in 23 μL of Elution buffer (10 mM Tris-HCl, pH 8.5) and incubated at room temperature (25° C.) for 2 minutes. 20 μL of eluted DNA was amplified according to Collibri™ PS DNA Library Prep Kit for Illumina protocol; nine amplification cycles were performed. Amplified library was cleaned up according to Cleanup of small fragment DNA Library using Invitrogen™ Collibri™ PS DNA Library Prep Kit for Illumina™ (Post-amplification cleanup) protocol. Agilent capillary electrophoresis showed characteristic cfDNA library profile of 3 peaks. Thus, the ComEA10 nucleic acid binding domain can also be used in similar binding and elution conditions as the above described CoEA15 and ComEA2 mutants, that is ComEA10 can elute DNA at lower salt or no salt solution, as compared to binding solution, while incubation temperature during elution is the same as compared with temperature during binding.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

---

What is claimed is:

1. A method of isolating a nucleic acid from a sample, comprising:

contacting one or more isolated nucleic acid binding domains with a sample comprising a nucleic acid under conditions suitable for binding, wherein the one or more isolated nucleic acid binding domains comprise SEQ ID NO: 10, SEQ ID NO: 15 with a mutation T10K, L16F, S20K, A27T, S41N, D44G, K55R, E54Q, D44Y, I52F, D45Q, S41R, E54A or T56I, or SEQ ID NO: 2 with a mutation R29D, and the one or more isolated nucleic acid binding domains are bound to a solid matrix either before or after contacting it with the sample; and separating the sample from the solid matrix with the bound one or more isolated nucleic acid binding domains bound to the nucleic acid.

2. The method of claim 1, wherein the one or more isolated nucleic acid binding domains is bound to the solid matrix before contacting it with the sample.

3. The method of claim 1, wherein the sample comprises blood, plasma, serum, urine, saliva, cell lysate, enzymatic reaction mixture, or a buffer.

4. The method of claim 1, wherein the nucleic acid is eluted from the one or more isolated nucleic acid binding domains before further steps.

5. The method of claim 1, wherein the one or more isolated nucleic acid binding domains consist of SEQ ID NO: 2 with a mutation R29D.

6. The method of claim 1, comprising a step wherein the nucleic acid is enzymatically or chemically modified without disrupting the binding of the nucleic acid to the one or more isolated nucleic acid binding domains.

7. The method of claim 1, wherein the method comprises depleting the nucleic acid from the sample.

8. The method of claim 7, wherein the one or more isolated nucleic acid binding domains binds RNA for depleting RNA from the sample.

9. The method of claim 1, wherein the one or more isolated nucleic acid binding domains consist of SEQ ID NO: 10.

10. The method of claim 1, wherein the one or more isolated nucleic acid binding domains consist of SEQ ID NO: 15 with a T10K, L16F, S20K, A27T, S41N, D44G, K55R, E54Q, D44Y, I52F, D45Q, S41R, E54A, or T56I mutation.

11. The method of claim 1, wherein the solid matrix is magnetic beads.

12. The method of claim 1, wherein the sample comprising the nucleic acid comprises genomic DNA or cell-free DNA.

13. The method of claim 1, wherein the sample comprising the nucleic acid is a sample that has been run through an electrophoretic gel.

14. The method of claim 4, wherein the elution is performed by heating to 65° C. or higher.

15. The method of claim 4, wherein the elution is performed by incubation in a solution with salt concentration 0 to 50 mM NaCl, by incubation in a buffered solution, or by incubation in water.

16. The method of claim 6, wherein the enzymatic modification is ligation, phosphorylation, dephosphorylation, end blunting, tailing of ends, or enzymatic fragmentation of the nucleic acid.

17. The method of claim 7, wherein the method removes DNA contamination in the sample.

18. The method of claim 7, wherein the one or more isolated nucleic acid binding domains bind single-stranded DNA and deplete single-stranded DNA from the sample.

* * * * *

SEQUENCE LISTING

<160> NUMBER OF SEQ ID NOS: 131

<210> SEQ ID NO 1
<211> LENGTH: 69
<212> TYPE: PRT
<213> ORGANISM: Thermobifida fusca

<400> SEQUENCE: 1

Gly Asp Gly Arg Ile Asp Leu Asn Thr Ala Thr Ala Asp Gln Leu Gln
1               5                   10                  15

Thr Leu Pro Gly Ile Gly Pro Val Leu Ala Gln Arg Ile Ile Asp His
            20                  25                  30

Arg Ala Ser Ile Gly Gly Phe Thr Ser Val Glu Gln Leu His Asp Val
        35                  40                  45

Thr Gly Ile Gly Asp Arg Arg Phe Ala Glu Leu Arg Asp Leu Val Tyr
    50                  55                  60

Val Gly Gly Ala Pro
65

<210> SEQ ID NO 2
<211> LENGTH: 68
<212> TYPE: PRT
<213> ORGANISM: Thermotoga naphthophila

<400> SEQUENCE: 2

Val Val Ala Phe Pro Val Glu Leu Asn Thr Ala Ser Leu Glu Asp Leu
1               5                   10                  15

Met Ser Ile Pro Gly Ile Gly Pro Val Lys Ala Gln Arg Ile Ile Asp
            20                  25                  30

Tyr Arg Glu Ser His Gly Gly Phe Ser Ser Val Glu Glu Leu Lys Asn
        35                  40                  45

-continued

```
Val Ser Gly Ile Gly Glu Lys Thr Leu Glu Lys Ile Ser Arg Tyr Val
50                  55                  60

Thr Val Glu Gly
65

<210> SEQ ID NO 3
<211> LENGTH: 60
<212> TYPE: PRT
<213> ORGANISM: Thermus sp.

<400> SEQUENCE: 3

Pro Glu Pro Ile Ser Leu Asn Arg Ala Ser Leu Glu Glu Leu Glu Ala
1               5                   10                  15

Leu Pro Gly Ile Gly Pro Thr Leu Ala Arg Arg Ile Val Glu Gly Arg
                20                  25                  30

Pro Tyr Gly Lys Val Glu Asp Leu Leu Arg Val Lys Gly Ile Gly Pro
        35                  40                  45

Ala Thr Leu Glu Arg Leu Arg Pro Tyr Val Arg Pro
    50                  55                  60

<210> SEQ ID NO 4
<211> LENGTH: 67
<212> TYPE: PRT
<213> ORGANISM: Ammonifex degensii

<400> SEQUENCE: 4

Ser Ser Gly Gly Lys Ile Asn Leu Asn Thr Ala Asp Glu Ala Ala Leu
1               5                   10                  15

Gln Thr Leu Pro Gly Ile Gly Pro Thr Leu Ala Arg Arg Ile Val Glu
                20                  25                  30

Tyr Arg Ala Lys Asn Gly Pro Phe Thr Ser Val Glu Asp Leu Ala Lys
        35                  40                  45

Val Pro Gly Ile Gly Pro Arg Arg Leu Glu Gln Leu Arg Glu Tyr Val
    50                  55                  60

Cys Ala Pro
65

<210> SEQ ID NO 5
<211> LENGTH: 67
<212> TYPE: PRT
<213> ORGANISM: Arcticibacter eurypsychrophilus

<400> SEQUENCE: 5

Glu Leu Arg Val Ile Glu Leu Asn Ala Ala Asp Ser Ala Gln Leu Val
1               5                   10                  15

Asp Ile Ile Gly Ile Gly Pro Val Leu Ala Leu Arg Ile Ala Lys Tyr
                20                  25                  30

Arg Asn Arg Leu Gly Gly Phe His Ser Lys Glu Gln Leu Arg Glu Ile
        35                  40                  45

Phe Gly Ile Asp Ser Leu Lys Tyr Ala Glu Ile Lys Asn Gln Val Arg
    50                  55                  60

Val Asp Gln
65

<210> SEQ ID NO 6
<211> LENGTH: 67
<212> TYPE: PRT
<213> ORGANISM: Arcticibacter svalbardensis

<400> SEQUENCE: 6
```

```
Glu Leu Arg Val Val Glu Leu Asn Ala Ala Asp Ser Ala Gln Leu Val
1               5                   10                  15

Asp Ile Ile Gly Ile Gly Pro Val Leu Ala Val Arg Ile Ala Lys Tyr
            20                  25                  30

Arg Asp Arg Leu Gly Gly Phe His Thr Lys Glu Gln Leu Gln Glu Val
        35                  40                  45

Phe Gly Ile Asp Ser Leu Lys Tyr Ala Glu Ile Lys Asn Gln Val Arg
    50                  55                  60

Val Glu Gln
65
```

```
<210> SEQ ID NO 7
<211> LENGTH: 67
<212> TYPE: PRT
<213> ORGANISM: Belliella baltica

<400> SEQUENCE: 7

Gln Leu Asn Lys Ile Ser Phe Asp Glu Ala Asp Ser Ile Val Leu Gln
1               5                   10                  15

Ile Val Pro Gly Val Gly Pro Ala Thr Ala Gly Arg Ile Ile Lys Phe
            20                  25                  30

Arg Asp Ala Ile Gly Gly Met His Thr Ser Glu Gln Leu Leu Asp Val
        35                  40                  45

Tyr Gly Met Ser Pro Glu Val Met Glu Arg Val Phe Glu Tyr Phe Glu
    50                  55                  60

Phe Thr Pro
65
```

```
<210> SEQ ID NO 8
<211> LENGTH: 67
<212> TYPE: PRT
<213> ORGANISM: Cyclobacterium amurskyense

<400> SEQUENCE: 8

Ser Phe Asn Lys Ile Thr Phe Ser Glu Ala Thr Ala Ile Glu Leu Gln
1               5                   10                  15

Met Val Gln Gly Val Gly Pro Phe Leu Ser Ala Arg Ile Asp Asp Tyr
            20                  25                  30

Arg Glu Ser Leu Gly Gly Phe His Ser Pro Glu Gln Ile Leu Glu Val
        35                  40                  45

Tyr Gly Val Asp Ala Glu Leu Ala Glu Lys Ile Tyr Ser Val Phe Ala
    50                  55                  60

Phe Glu Ser
65
```

```
<210> SEQ ID NO 9
<211> LENGTH: 69
<212> TYPE: PRT
<213> ORGANISM: Hymenobacter sp.

<400> SEQUENCE: 9

His Leu Ala Ile Phe Asp Leu Asn Thr Ala Asp Thr Thr Gln Leu Met
1               5                   10                  15

Gln Ile Arg Gly Ile Gly Arg Gly Ile Ser Ala Arg Ile Val Ala Tyr
            20                  25                  30

Arg Ala Arg Leu Gly Gly Phe Val Arg Ala Glu Gln Met Ala Glu Ile
        35                  40                  45
```

-continued

```
Tyr Ser Leu Arg Asp Ala Pro Asp Leu Ile Asp Ser Leu Arg Lys Tyr
    50              55                  60

Thr Phe Val Lys Ala
65

<210> SEQ ID NO 10
<211> LENGTH: 66
<212> TYPE: PRT
<213> ORGANISM: Clostridium ultunense

<400> SEQUENCE: 10

Ser Pro Lys His Leu Val Asp Leu Asn Arg Ala Thr Ile Gly Asp Leu
1               5                   10                  15

Glu Gln Leu Pro Gly Ile Gly Pro Gln Thr Ala Glu Arg Val Val Arg
            20                  25                  30

Phe Arg Glu His Asn Gly Pro Tyr Arg Ser Ile Asp Asp Leu Lys Lys
        35                  40                  45

Val Gly Gly Ile Gly Glu Arg Thr Leu Glu Lys Ile Ser Pro Trp Val
    50                  55                  60

Thr Val
65

<210> SEQ ID NO 11
<211> LENGTH: 67
<212> TYPE: PRT
<213> ORGANISM: Fictibacillus arsenicus

<400> SEQUENCE: 11

Glu Lys Asp Asp Leu Leu Asn Ile Asn Ser Ala Asp Leu Ser Glu Leu
1               5                   10                  15

Gln Thr Leu Ser Gly Val Gly Pro Ser Lys Ala Gln Ser Ile Ile Ser
            20                  25                  30

Tyr Arg Glu Glu Phe Gly Pro Phe Lys Ser Ile Asp Gln Leu Leu Glu
        35                  40                  45

Val Arg Gly Ile Gly Glu Lys Thr Ile Glu Glu Trp Lys Asp Lys Ile
    50                  55                  60

Lys Phe Gln
65

<210> SEQ ID NO 12
<211> LENGTH: 67
<212> TYPE: PRT
<213> ORGANISM: Cellulophaga geojensis

<400> SEQUENCE: 12

Ile Asn Tyr Thr Val Lys Asp Ile Asn Asn Ala Thr Ala Ile Asp Leu
1               5                   10                  15

Gln Val Val Ser Gly Ile Gly Glu Lys Ile Ser Ser Arg Ile Val Lys
            20                  25                  30

Phe Arg Asp Arg Leu Gly Gly Phe Val Val Asn Glu Gln Leu Gln Asp
        35                  40                  45

Val Tyr Gly Leu Asp Lys Glu Val Leu Asn Arg Leu Leu Lys Gln Phe
    50                  55                  60

Lys Val Ile
65

<210> SEQ ID NO 13
<211> LENGTH: 67
<212> TYPE: PRT
```

-continued

<210> ORGANISM: Ekhidna lutea

<400> SEQUENCE: 13

```
Lys Ser Ile Asp Ile Tyr Asp Leu Asn Thr Ala Thr Glu Glu Asp Leu
1               5                   10                  15

Gln Lys Ile Lys Gly Ile Gly Pro Ala Tyr Ser Glu Arg Ile Val Lys
            20                  25                  30

Tyr Arg Asn Leu Leu Gly Gly Phe Ser Asp Thr Thr Gln Leu His Glu
        35                  40                  45

Val Tyr Gly Leu Lys Pro Glu Thr Ile Ser Arg Leu Leu Glu Gln Phe
    50                  55                  60

Arg Ile Leu
65
```

<210> SEQ ID NO 14
<211> LENGTH: 67
<212> TYPE: PRT
<213> ORGANISM: Sporolactobacillus nakayamae

<400> SEQUENCE: 14

```
Gly Ser Thr Glu Met Val Asn Val Asn Thr Ala Asp Glu Gln Ala Met
1               5                   10                  15

Gln Asn Leu Pro Gly Ile Gly Pro Ala Lys Ala Lys Ala Ile Ile Gln
            20                  25                  30

Tyr Arg Asp Glu His Gly Pro Phe Asn Ser Leu Asp Glu Leu Thr Asp
        35                  40                  45

Val Ser Gly Ile Gly Glu Lys Ser Leu Glu Lys Met Lys Pro Asn Met
    50                  55                  60

Ser Leu Gln
65
```

<210> SEQ ID NO 15
<211> LENGTH: 67
<212> TYPE: PRT
<213> ORGANISM: Streptococcus equinus

<400> SEQUENCE: 15

```
Ala Asp Ser Ala Gln Ile Asn Leu Asn Thr Ala Ser Leu Glu Glu Leu
1               5                   10                  15

Gln Thr Ile Ser Gly Ile Gly Ala Lys Arg Ala Gln Asp Ile Ile Asp
            20                  25                  30

Tyr Arg Asp Asn Asn Gly Gly Phe Ser Ser Val Asp Asp Leu Lys Asn
        35                  40                  45

Val Ser Gly Ile Gly Glu Lys Thr Leu Glu Lys Leu Lys Ala Glu Val
    50                  55                  60

Thr Val Asp
65
```

<210> SEQ ID NO 16
<211> LENGTH: 69
<212> TYPE: PRT
<213> ORGANISM: Octadecabacter arcticus

<400> SEQUENCE: 16

```
Leu Val Ile Ala Phe Val Ser Val Leu Cys Gly Ser Thr Ser Cys Ala
1               5                   10                  15

Glu Met Ala Ala Phe Gly Arg Ala Lys Glu Ser Leu Phe Arg Asn Phe
            20                  25                  30
```

```
Leu Lys Leu Lys His Ala Ile Pro Ser His Asp Thr Phe Ser Glu Val
        35                  40                  45

Phe Arg Ile Ile Asp Pro Lys Ala Leu Asp Ala Ala Phe Ser Lys Val
    50                  55                  60

Leu Ala Asp Val Thr
65
```

```
<210> SEQ ID NO 17
<211> LENGTH: 68
<212> TYPE: PRT
<213> ORGANISM: Psychromonas ingrahamii

<400> SEQUENCE: 17

Leu Phe Leu Ala Ile Thr Ala Val Ile Ser Gly Cys Glu Gly Trp Glu
1                   5                   10                  15

Glu Ile Gln Asp Phe Gly Asn Asp Lys Leu Asp Trp Leu Arg Lys Tyr
                20                  25                  30

Leu Pro Phe Ser Gly Gly Ile Pro Thr Asp Asp Thr Ile Ser Arg Ile
        35                  40                  45

Phe Gln Leu Ile Asp Pro Lys Glu Phe Gln Lys Cys Phe Ala Thr Trp
    50                  55                  60

Met Lys Ser Cys
65
```

```
<210> SEQ ID NO 18
<211> LENGTH: 68
<212> TYPE: PRT
<213> ORGANISM: Shewanella psychrophila

<400> SEQUENCE: 18

Leu Phe Leu Thr Met Val Ala Val Ile Gly Gly Cys Glu Gly Trp Glu
1                   5                   10                  15

Asp Ile Glu Asp Phe Gly His Cys His Leu Glu Leu Leu Lys Lys Tyr
                20                  25                  30

Gly Asp Phe Ser Ala Gly Ile Pro Val His Asp Thr Ile Ala Arg Ile
        35                  40                  45

Ile Cys Lys Val Asp Pro Glu Ala Leu Gln Gln Ala Phe Ile Ser Trp
    50                  55                  60

Met Gln Ala Thr
65
```

```
<210> SEQ ID NO 19
<211> LENGTH: 65
<212> TYPE: PRT
<213> ORGANISM: Thermus sp.

<400> SEQUENCE: 19

Met Ala Phe Leu Ala Arg Val Asp Ser Leu Arg Gly Val Glu Arg Phe
1                   5                   10                  15

Ala Arg Ala Asn Pro His Leu Leu Pro His Leu Gly Leu Arg Asn Pro
                20                  25                  30

Pro Gly His Thr Ile Leu Thr Leu Leu Leu His Arg Leu Asp Pro Lys
        35                  40                  45

Lys Leu Gln Glu Ala Leu Leu Gln Val Phe Pro Glu Val Asp Leu Gly
    50                  55                  60

Gly
65
```

<210> SEQ ID NO 20
<211> LENGTH: 70
<212> TYPE: PRT
<213> ORGANISM: Meiothermus taiwanensis

<400> SEQUENCE: 20

Val Ala Leu Val Leu Val Ala Phe Val Cys Arg Val Asp Ser Leu Arg
1               5                   10                  15

Gly Val Ala Arg Phe Ala Gln Ala Asn Pro Phe Leu Cys Lys Pro Leu
            20                  25                  30

Gly Leu Arg Lys Ala Pro Gly Arg Ser Ser Ile Ala Gln Leu Ile Arg
        35                  40                  45

Arg Leu Asp Pro Gln Ala Leu Gly Ser Ala Leu Gln Gln Val Phe Pro
    50                  55                  60

Glu Leu Pro Leu Pro Ala
65                  70

<210> SEQ ID NO 21
<211> LENGTH: 70
<212> TYPE: PRT
<213> ORGANISM: Thermus filiformis

<400> SEQUENCE: 21

Leu Gly Leu Ile Leu Val Ala Phe Leu Cys Arg Val Asp Ser Leu Arg
1               5                   10                  15

Gly Val Ala Arg Phe Ala Arg Glu Asn Pro Glu Leu Leu Pro Leu Leu
            20                  25                  30

Gly Leu Arg Lys Pro Pro Gly His Tyr Thr Val Thr Thr Ile Leu His
        35                  40                  45

Arg Leu Asp Pro Gln Asp Leu Gln Glu Ala Leu Arg Ser Val Phe Pro
    50                  55                  60

Glu Ala Asp Leu Ala Ala
65                  70

<210> SEQ ID NO 22
<211> LENGTH: 67
<212> TYPE: PRT
<213> ORGANISM: Litorilinea aerophila

<400> SEQUENCE: 22

Met Ile Leu Ala Val Met Gln Gly Glu Asn Ser Leu Arg Gly Ile Ala
1               5                   10                  15

Gln Trp Met Arg Leu His Trp Glu Glu Ile Ala Glu Pro Leu Asn Leu
            20                  25                  30

Trp Ala Thr Lys Gly Ala Pro Ser Tyr Gly Thr Leu Trp Asn Leu Leu
        35                  40                  45

Ala Ser Leu Asp Pro Lys Glu Leu Asn Gln Val Leu Gln Gly Ala Glu
    50                  55                  60

Glu Gly Gly
65

<210> SEQ ID NO 23
<211> LENGTH: 67
<212> TYPE: PRT
<213> ORGANISM: Methylobacterium aquaticum

<400> SEQUENCE: 23

Leu Thr Leu Ser Leu Ala Ala Met Leu Ser Gly Ala Asn Asp Leu Arg
1               5                   10                  15

-continued

```
Ala Val Phe Arg Trp Gly Arg Arg Leu Pro Pro Glu Ala Leu Phe Leu
            20              25              30

Leu Gly Leu Glu Arg Ala Pro Cys His Ala Thr Tyr His Tyr Phe Phe
        35              40              45

Lys Ala Leu Asp Val Ala Ala Thr Glu Ala Val Leu Gly Ala Trp Val
    50              55              60

Arg Gly Ala
65

<210> SEQ ID NO 24
<211> LENGTH: 72
<212> TYPE: PRT
<213> ORGANISM: Rhodopseudomonas palustris

<400> SEQUENCE: 24

Leu Phe Ile Ala Leu Leu Ala Thr Leu Cys Gly Ala Thr Ala Cys Thr
1               5               10              15

Asp Met Ala Leu Phe Ala Arg Leu Lys Ala Tyr Leu Trp Gln Asp Val
            20              25              30

Leu Val Leu Glu Asn Gly Leu Pro Ser His Asp Thr Phe Ser Arg Val
        35              40              45

Phe Arg Met Leu Asp Pro Ala Ala Phe Glu Lys Ala Phe Gln Arg Phe
    50              55              60

Met Lys Ala Phe Ala Gln Gly Ala
65                  70

<210> SEQ ID NO 25
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(5)
<223> OTHER INFORMATION: Any amino acid
<220> FEATURE:
<221> NAME/KEY: VARIANT
<222> LOCATION: (6)..(6)
<223> OTHER INFORMATION: /replace="Met"
<220> FEATURE:
<221> NAME/KEY: MOD_RES
<222> LOCATION: (7)..(10)
<223> OTHER INFORMATION: Any amino acid
<220> FEATURE:
<221> NAME/KEY: VARIANT
<222> LOCATION: (12)..(12)
<223> OTHER INFORMATION: /replace="Val"
<220> FEATURE:
<221> NAME/KEY: MOD_RES
<222> LOCATION: (14)..(19)
<223> OTHER INFORMATION: Any amino acid
<220> FEATURE:
<221> NAME/KEY: VARIANT
<222> LOCATION: (20)..(20)
<223> OTHER INFORMATION: /replace="Val"
<220> FEATURE:
<221> NAME/KEY: MOD_RES
<222> LOCATION: (21)..(23)
<223> OTHER INFORMATION: Any amino acid
<220> FEATURE:
<221> NAME/KEY: SITE
<222> LOCATION: (1)..(24)
<223> OTHER INFORMATION: /note="Variant residues given in the sequence
      have no preference with respect to those in the annotations
      for variant positions"
```

-continued

```
<400> SEQUENCE: 25

Ala Xaa Xaa Xaa Xaa Leu Xaa Xaa Xaa Xaa Gly Ile Gly Xaa Xaa Xaa
1               5                   10                  15

Xaa Xaa Xaa Ile Xaa Xaa Xaa Arg
            20

<210> SEQ ID NO 26
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(7)
<223> OTHER INFORMATION: Any amino acid
<220> FEATURE:
<221> NAME/KEY: VARIANT
<222> LOCATION: (8)..(8)
<223> OTHER INFORMATION: /replace="Met"
<220> FEATURE:
<221> NAME/KEY: MOD_RES
<222> LOCATION: (9)..(12)
<223> OTHER INFORMATION: Any amino acid
<220> FEATURE:
<221> NAME/KEY: VARIANT
<222> LOCATION: (14)..(14)
<223> OTHER INFORMATION: /replace="Val"
<220> FEATURE:
<221> NAME/KEY: MOD_RES
<222> LOCATION: (16)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid
<220> FEATURE:
<221> NAME/KEY: VARIANT
<222> LOCATION: (22)..(22)
<223> OTHER INFORMATION: /replace="Val"
<220> FEATURE:
<221> NAME/KEY: MOD_RES
<222> LOCATION: (23)..(25)
<223> OTHER INFORMATION: Any amino acid
<220> FEATURE:
<221> NAME/KEY: MOD_RES
<222> LOCATION: (27)..(37)
<223> OTHER INFORMATION: Any amino acid
<220> FEATURE:
<221> NAME/KEY: SITE
<222> LOCATION: (27)..(37)
<223> OTHER INFORMATION: /note="This region may encompass 7-11 residues"
<220> FEATURE:
<221> NAME/KEY: MOD_RES
<222> LOCATION: (39)..(40)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: SITE
<222> LOCATION: (1)..(45)
<223> OTHER INFORMATION: /note="Variant residues given in the sequence
      have no preference with respect to those in the annotations
      for variant positions"

<400> SEQUENCE: 26

Asn Xaa Ala Xaa Xaa Xaa Xaa Leu Xaa Xaa Xaa Xaa Gly Ile Gly Xaa
```

-continued

```
 1               5              10              15
Xaa Xaa Ala Xaa Xaa Ile Xaa Xaa Xaa Arg Xaa Xaa Xaa Xaa Xaa Xaa
             20              25              30

Xaa Xaa Xaa Xaa Xaa Leu Xaa Xaa Val Xaa Gly Ile Gly
         35              40              45

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Leu Asn Asp Ile Phe Glu Ala Gln Lys Ile Glu Trp His Glu
1               5              10              15

<210> SEQ ID NO 28
<211> LENGTH: 1068
<212> TYPE: DNA
<213> ORGANISM: Thermobifida fusca

<400> SEQUENCE: 28
atggcacgac acactgctcc tgagcccgct gccccggcag cgcagcagcc gtctcccctg       60
ccgtcgtctg aggccgcctt gcctgccgag tggcgggcag cggacgacgg ggacccgacc      120
ccactggact tcactgttcc tcccccgccc tatgccgtag ccgacacggt ccgctccccg      180
gtgcccgtgc ttcccgcgcc acggcgtccc ccggctcccg aggtggggag ggacgaggat      240
gcggcagagc gccctgcccg ggcgggccgc ggtgcccgtc cggccccgcc cgccgcacct      300
cagccggacc gcggcacggg tcggaacgac ggttcggctc ccgctccccc gcccgggtat      360
gtgcgcatcc cgccgctccc cgacccggcg gagcggcggc tgcctgcccc gctggcggcc      420
cttgtggacc gctggagggg tgtctcagtg gagctgcggc cccgcgtgac cctgtccggg      480
gtggcggcgc tcgccctcgt gtgcctgctg gccgcggggg tcaccggctg gttcatgctc      540
aacgcccgtc ccgcgtccgc gcccgcgcg ccgcaggagg ccgtcccgtc cggtcctcat      600
ccgtccccgg cggcggaagc gagtcctgcc ggcacggtcg tggtccacgt gggcggtgac      660
gtggtctccc cggggatcgt gaccctgccc gccgggtccc gggtggccga tgctctcgac      720
gcggcgggcg gcccgcgccc ggatgcggat ctagggttcc tcaacctggc ccgtcccctc      780
gtcgacggca gcagatcct cgttggggtc acccccgtcgc ccatggccgg ggaaggcgag      840
ggtccgggcc tgcccgccgg ggacgggcgg atcgacctca acaccgctac cgccgaccag      900
ttgcagaccc tgccgggaat cggccgtg ctggcccagc gcatcatcga ccaccgcgcg      960
tccatcggcg gtttcaccct ggtggagcag ctccacgacg tcaccggtat cgggggaccgc     1020 cggttcgcgg agctgcgcga cctggtctac gtcggcggtg ccccgtga               1068

<210> SEQ ID NO 29
<211> LENGTH: 507
<212> TYPE: DNA
<213> ORGANISM: Thermotoga naphthophila

<400> SEQUENCE: 29
gtggcacttg ttttcttcat attgcttgga attgttatgg aacgagaaac gaaaacagaa       60
gaggacacaa catcctctca gaaggttgtc gcctttcctg tggagctgaa caccgcttct      120
```

-continued

```
ctggaagact tgatgtcgat tccagggatc gggcctgtga aagcccagag gatcatcgat      180
tacagagagt cacatggtgg attttcgagc gtggaagaat tgaagaacgt ctctggaatc      240
ggagaaaaaa ccctggagaa gatttccaga tatgtgaccg tcgaaggagt tgaacaacat      300
atcaaaagag aagtcacaaa actgaacgtg aacacagctt cggttgaaga actcgaaacc      360
cttccctaca taggtgaggt aaaggcaaaa gccattgtcg agtaccgaga gaaaaacggt      420
ccctttcgtt ctcccgaaga tcttctggac gtgcctggaa taggtgaaaa gacgctggag      480
aaaataagag gaaaaatcac attttga      507

<210> SEQ ID NO 30
<211> LENGTH: 309
<212> TYPE: DNA
<213> ORGANISM: Thermus sp.

<400> SEQUENCE: 30
gtggtccttg gctacctcct ggcggtagcc ctcctgggcc tcctggccct gtggcccaag       60
gtggccccgg acccggcccc cgtggcagtg gaggtctggg cagagccccg cttcacccct      120
ccaccccggg agcccatcag cctgaaccgg gccagcctgg aggagctgga ggccctgccc      180
ggtatcggcc ccaccctggc gcggaggatc gtggagggcc ggccttacgg gaaggtggag      240
gacctcctgc gggtgaaggg gatcgggccg gccaccctgg agcggctccg accctacgtg      300
cgcccctga      309

<210> SEQ ID NO 31
<211> LENGTH: 585
<212> TYPE: DNA
<213> ORGANISM: Ammonifex degensii

<400> SEQUENCE: 31
ttgaccttcg ggaagcgaga atatttcgtg gccctggcgc tggggatagc tttgctgtta       60
ggcttagggg tcaggcacct cttttcccgc ccggttgagg taacgcctgc tcctccggca      120
gtggagcggg aggaaaagat aagaggtacg gtgtgggtgc acgtggcagg ggaagttagt      180
catcccggag tttacgaact ccctgccggc agccgggtaa aggatgccct ggaaaaggct      240
ggccttcttc caacggccga cccccacgcc ctgaacttgg cgcaggtctt ggtggacggg      300
cagaagatcg tagtccctcc caagcttgca gaggggaaag aaggcgaggt aaataaccccc      360 tttgctactc gggtttctgc ttcctccggg gggaagatca acctcaatac cgccgatgag      420
gccgcgcttc agaccctgcc tgggataggc cctacgctgg cgcgccgcat tgtgtgagtac      480 cgggccaaga acggtccgtt tacctcggtg gaggacctgg ctaaggtgcc aggcatcggt      540
cccaggcgcc tggagcagtt gcgcgagtac gtgtgcgccc cttga      585

<210> SEQ ID NO 32
<211> LENGTH: 1008
<212> TYPE: DNA
<213> ORGANISM: Arcticibacter eurypsychrophilus

<400> SEQUENCE: 32
ttgaaaaagt ggttaaatgc attttttggt ttcacaaaga aggagcaaaa cggattattg       60
gttctatgta ttcttatttg tttagttgct ttattcccct gggtgtatgc tgcagtccag      120
tcgcctgttg tttatcattt ttcggactat tccaaatttg ctgaaacagt cagtgagtct      180
tccacaggca atccaaattc atcgtatcca aattcgccag ggtataatca ttcttcctat      240
agtaattctc actcttatac ccattctggg gttacaggcc cctccggatc gcgtataaaa      300
```

-continued

```
gcacagtatt ttcttttttaa ccccaatcag ctagccacag cagactggaa gaaactgggg      360
ctgtccgaaa aacaggtcca ggtcattcat cattatgaag ataagggtgg aagctttcgg      420
aagaaggaag atctgaagaa gatctactcc ctttcagctt atgaatatga tcatctcgag      480
ccgtatatac ggattcccga aacctcattt ccgaacgcct cttttaaaaa gaatgattat      540
acaggatcaa aaactaatcc tgattaccat ttcgtcaaga aaagttatcc ccagtatgta      600
aaacgtgaac tgagggttat tgaattaaat gctgcagact ctgctcagtt agttgatata      660 ataggatcg gaccagtgct ggctcttcgc attgctaaat atagaaacag gttaggtgga      720
ttccattcca aggagcagct gcgggagatt ttcggtattg actccctgaa gtatgctgaa      780
ataaagaacc aggtacgcgt ggaccaagta tccctgcatc agatcaatat caatacggct      840
acatttgagg acttaaaaaa gattccctat ttcagttaca aacaaatcaa tgccttaatt      900
cagtataaga agcagcatgg agaatatcat tcaatagacg atttgaggca gataagcatt      960
cttaactctg aaattttgct taaaattgca ccttatttaa ttttccaa               1008
```

<210> SEQ ID NO 33
<211> LENGTH: 651
<212> TYPE: DNA
<213> ORGANISM: Arcticibacter svalbardensis

<400> SEQUENCE: 33

```
ttgtccgaaa agcagatcca ggtcattcat cactatgagg acaagggtgg aagctttcgc       60
aagaaggaag atctgcaaaa aatctattcc atttctactt ttgaatatgc tcatctcgaa      120
ccctatatcc ggattcccga aacttcttat aataatacct cttttaaaag gaatgattat      180
gccggatcaa aagctaatcc tgattaccat tatgtcaaga aaaattatcc tccgaatgca      240
aaacgagaac tgagggttgt tgaattaaat gctgcagact ctgctcaatt agttgatata      300
ataggcatcg gaccagtgct ggccgttcga atagccaaat accgagaccg tctaggtgga      360
tttcatacca aagagcaact tcaggaagta tttgggatcg actccctgaa gtatgcagaa      420
ataaagaacc aggtacgcgt ggaacaggga tccctgcatc agctcaatat caatacggct      480
acatttgagg acttaaaaaa gtttccctat tttagttata agcaaataaa tgccttaatt      540
caatataaga agcagcatgg agaatatcat tcaatagatg atttgaggca gattagcatt      600
cttaactctg aaattttgct taaaattgca ccttatttaa ttttccaatg a            651
```

<210> SEQ ID NO 34
<211> LENGTH: 660
<212> TYPE: DNA
<213> ORGANISM: Belliella baltica

<400> SEQUENCE: 34

```
atgattcgaa aaatgaagtt ttttctcaaa aattaccttg ggtttagcaa tagagaatct       60
agaggtttta tcttgttagt tcctgcctta ttacttttgt atgcagtacc tgtgatttac      120
aataacattt tggcgaaaag gaatcaaata gattatgaaa tctatttgga gaagatggat      180
agtttagaaa gcgctggttg gcataaggtc gaaactcaat atttcatgag tcaggatact      240
tcaaaaagaa gacaacctca gcttaacaaa atatcttttg acgaagcaga ttcgattgtt      300
ttacaaatag ttcccggtgt tggtccggct acagcaggta ggattatcaa attccgtgat      360
gcaattggag gaatgcatac ttctgagcaa cttcttgatg tttatggaat gagtcctgaa      420
gtcatggaaa gagtgtttga gtattttgaa ttcactccgg gaataaaaac taaaatcaat      480
```

-continued

```
atcaatacag cagatgtccc aactttggcg gcacatcctt atattaatta tggtagtgcc        540
aaagtgattg tagcttatag agatcagcat ggagcttaca ctaccgctga tgatttatta        600
aaagttagaa tcttcagcca agagtggatt gatagaatca gaccctattt aacttattaa        660

<210> SEQ ID NO 35
<211> LENGTH: 675
<212> TYPE: DNA
<213> ORGANISM: Cyclobacterium amurskyense

<400> SEQUENCE: 35
ttgggtttta cccgtaggga aatgcgtggt ttcgtttttg taatccctat actttgcctg         60
ctatacgctg ggccattttt tatagaacgc tatcaccact cttctgatca agctacttat        120
ttggcttaca ttgctgaaaa caatgaattg ctaagccaaa aggttccttc tcggatagat        180
tctagtcaga aaaccaaaa gccaagccag gaaacaaaga gggaagaaaa gaaaagcagc        240
tcttcatcat cactaaagaa acctagcaag ccaagtttca ataaaataac tttttctgaa        300
gctactgcca ttgaattgca aatggtacaa ggtgtaggac ctttctcttc tgcgcgaatt        360
gatgattaca gagaaagttt aggcggtttt cacagtccgg agcaaattct ggaagtttat        420
ggggtagatg ctgaactcgc cgagaaaatt tactctgtat ttgcttttga atcccatata        480
agccgtcaat taaatatcaa ttcagcagat tttaaacaat tgataaagca cccttatata        540
gactatgggg ccactaaggt gattttggct tataggaaac aacatgggcc atacaaatca        600
gcagaagagt tgttgaatat taaaattttc aatgaagact gggtaaatag agtttccct         660 tacctgactt tttga                                                        675

<210> SEQ ID NO 36
<211> LENGTH: 1032
<212> TYPE: DNA
<213> ORGANISM: Hymenobacter sp.

<400> SEQUENCE: 36
atgaaagtca aacaagctag gccttctacg ccgccagctt ctttttttag gaagagccag         60
acagcgctcc ggcgctactt cggcttttcg cgtcgcgaga cgtccggttt tgtggtgctg        120
gtggctttgc tactgttgtg gttgtttctg ccggccctgt tgcgtcccgc cttgccccag        180
tacgacccag ccgccgatca gcgccagtta gagcaggtag caacggagct agcggtccag        240
cgccagcctc gggccttcgc cgaccggcgc tacccgcgcc gcggctatgc ccgcgcgta         300 cccgtgccac aggtcccct tgctcctttc gacccaaata gtctcacgcc gcttgagtgg        360
gaagcccgcg gcttgccgca cttcgtggcc gaacgcattg tgcacttccg cgacgtagta        420
ggcgggttca aagccaaaga gcagatccga cgcacctatg ggcttccaga ttcggtgtac        480
gcgcggctag ctccgtacat gctgctgccc gatcagcttc cgccgcgcac ggctcgctcc        540
tatcctagct ccgagcgctt cgctggtaag tttacggaac gtcctagctt tcccaccagc        600
aagtttgccc gcaagcccgc gcacttggct attttcgact tgaacaccgc cgatacaaca        660
cagctcatgc agatccgggg catcgggcgc ggcatttcgg cgcgtattgt agcctaccgg        720
gcgcgactcg gtggtttcgt acgagccgag cagatggccg aaatctatag cttgcgcgac        780
gcacccgatc tcatagacag cctgcgcaaa tacaccttcg tgaaagctag ctttgcccca        840
gcctcactcg acgtgaatac ggctagcttc gacgagctac aaagtcatcc gtacatgggc        900
aagcgattgg cacgcgtagt ggtggctttc cgccagcagc acggcccctt caagcaaccc        960
gacgacctgc gccagatccg tattctggac gaggccacgt tcgaaaagct taagccatat       1020
```

-continued

```
ttacgctttt ga                                                    1032

<210> SEQ ID NO 37
<211> LENGTH: 669
<212> TYPE: DNA
<213> ORGANISM: Clostridium ultunense

<400> SEQUENCE: 37
atggaacggt tgatccggtt tgtaactgag cggcgaaaac ttttcatcgt catcgtactt      60
gcggccgtgg gctttatta tttgctgatc gccaaaacaa aggacgagga gaaatttctc     120
cttcctccct atgaccagga gagtgggggg accgtgacgg agaccggtac gggaagtcca     180
gatttcccta aggaaaaagg cggggaggga cttcctgcgg ttcaatggat tgaagtagat     240
gtgaaaggag cggtgagaaa tccgggagtg tataaaatcg aggagaatgc tcgggtccat     300
gatctcctgg agaaggcagg ggggacggta gaagaggcgg atctttctca ggtcaatttg     360
gccgcttttt taaaagacgg acaagtggta tatatccctc ggatagggga caaggtgtg     420 ggatggaatc ccccaatggc ctcaacttcg tcaaagggag gagatgccgg aaaaactcta     480
atcaatctta attccgctac gctggaagag ctggatcagc tcccaggcat ggcccctcg     540 aaggcggagt cgatccttcg ctatcgagag gaacacgggc cgtttaagga tgtgaatgag     600
ctaaccaacg tttccggaat cggtgagaag acactggaga aacttcttcc ctatatcact     660
gtccggtag                                                            669

<210> SEQ ID NO 38
<211> LENGTH: 627
<212> TYPE: DNA
<213> ORGANISM: Fictibacillus arsenicus

<400> SEQUENCE: 38
atgattcagc tgaaaaagca tataaacttg gtgctcggag ccactttatt acttttaatt      60
ttgattggag tgttcattta caaaaatata aacagtcagc ctgatttggt gatttcaccc     120
gaacaaatgc ctatgataaa agatgaaact gaaacgattg actctgaaac tgaaaaaaat     180
gaggaggaat ctattgtatc aggtccaatt atggtcgatg ttcagggaag tgttaatcga     240
cctggtgtgt atgaaatgaa taatggtgat cgtgtgattg acgtgattaa aaaagcgggt     300
ggttttttag aagaagcaga agctcgatca gtaaatcagg ctgagaaaat tattgatgaa     360
atgattatat atgttgcagc taaaggggaa gaggttcatc ctttatcttc taataaggga     420
aatgaaaaag atgatttgtt aaatattaat tctgctgatc tatctgaact tcagaccctt     480
agcggtgtcg gcccctctaa agctcaaagt attatttcct accgtgagga atttggaccg     540
ttcaaatcaa ttgatcagct tttagaagtt cgtggaattg gtgagaaaac gattgaagaa     600
tggaaagata aaattaaatt ccaataa                                         627

<210> SEQ ID NO 39
<211> LENGTH: 876
<212> TYPE: DNA
<213> ORGANISM: Cellulophaga geojensis

<400> SEQUENCE: 39
atgaagaatt ttaaatccca ctttcagttt gataaagaac agaaaagtgg gatttctttt      60
ttgttattat taattgtaat ttttcaggct atatattatt tggtttcaaa tggtgtattt     120
acttctaaaa ataatagttt actacataat aaagagcttc aggttgcaat agattcacta     180
```

```
aaaaatcaat ctgtaaaaaa gaatacatat aaaatgtacc cttttaatcc taattatata    240
acagattata aaggttataa attggggatg tctattaaag aaatagatag gttgcatttg    300
tatagggaaa cgggtaaata tgttaactct atagaggagt ttaagaaagt aacaaatgtc    360
tcagattcat tattaaaagc aatatctcca tattttaaat ttccagattg gaaagcttca    420
aaatttgaca aaaaaataac tgttgcaaat aagtcttcta aaaacatcaa ttatacagtt    480
aaggatatta ataatgccac tgcaatagac ttgcaggtgg taagtggaat tggagaaaaa    540
atatcttcca gaatagttaa atttagagat aggctaggtg gttttgtggt taatgagcag    600
ttgcaagatg tttatggttt agataaagaa gttttaaatc ggttgttaaa gcaatttaag    660
gtaattggta agcctgttat aagtaaaatt aatataaacg aggctagtgc ttatgaaatt    720
tctaagttgg tatatataaa atatgatgtt gctaaggcta ttgtggctta cagagaagaa    780
aatggaagat ttacatcttt taacgatttg gtaaatattg agggttttac tgtgaataag    840
attgatagaa ttaagttata tttgagcatt gattaa                             876

<210> SEQ ID NO 40
<211> LENGTH: 711
<212> TYPE: DNA
<213> ORGANISM: Ekhidna lutea

<400> SEQUENCE: 40
atgttgaaat ttttaatcaa cgccatttct cgtgcaatcg gcttcagcag aactgaagca     60
caaggatcat taatccttat tctattgatc tcaatcacta ttttctttta caacacaagg    120
gttgccagca tcaagcatca agtcgaaatc agatcagata gttccgcgat agaatggatt    180
aagtctgtcc atgcttctta ccagataaaa gaaacaaac ccaagtttga aaaaagcata     240
ttcctaccga agaaaactac ttatgaaaat agaaagacag aaaaatcaag tagtgtcaac    300
ccaaacaaga acaaatcaat tgacatctat gatctcaata ctgcaactga agaagattta    360
cagaaaatta aaggcattgg accagcctac tcagaacgca tagtcaaata cagaaactta    420
ctaggaggct tttcagacac tacgcagcta catgaagtat acggattgaa gcccgaaacc    480
atttcaagat tattagagca gttcaggatt ttaagcccag tgaaccagtt caatattaat    540
tccgattcaa taaagcattt agcaaagcat ccttatgttt catatgacct ggcttgggta    600
attatcaatt acagaagaga gcatggtgac attatgagtc cccaagagtt aaaaaaaata    660
aaagcactgg acgacagtac tttcataaga ttaaagccat atttggaata g            711

<210> SEQ ID NO 41
<211> LENGTH: 645
<212> TYPE: DNA
<213> ORGANISM: Sporolactobacillus nakayamae

<400> SEQUENCE: 41
ttgagagagc gcttgaataa atttagagta tgggtgatta tcggcgtagt cgcgggccctt    60 ctcatctttt ggctgcttta tcagcatcaa aacaatctca agcgatcagc ggaagtgcgg    120
aaaaccgatc agctcttttc gaagcaacag aaaagtaacg gtatatccga aagcccaatc    180
agcaagcaaa atagtttacc ttcagaactt gttatcgatg taaaagggc cgtacgaaat    240 ccgggcattt atcatgcgca agcatctgac cgtgtcattg atggtattaa gcaggctggc    300
ggtttcagca aaaagcgga tcgcgacaaa atcaatctgg cccagaaatt ggccgatgag    360
atggtaattt atgtgccgga gaaaggtgaa gagatgcagg tgtctgccgg cggggcaccg    420
ggagcggtgt ctgggcagca ggggagcaca gagatggtga atgtaaatac ggcggatgaa    480
```

-continued

```
caagcgatgc agaatctgcc cggaatcggt cctgcaaaag cgaaggcgat tattcagtat    540
cgagatgagc atggaccttt caatagcctg gatgagttga cagatgtttc aggaattggt    600
gagaagtctt tggagaagat gaaaccaaat atgtcactcc agtaa    645

<210> SEQ ID NO 42
<211> LENGTH: 681
<212> TYPE: DNA
<213> ORGANISM: Streptococcus equinus

<400> SEQUENCE: 42
atgattgaag agatgaaaga aaaaatttta gagcataaaa ctgtggcatc agttttgggg     60
acagtactta ttatgctagt gatgtttttt gcttggtcta gtatggaaag ccacaaagct    120
gaagtgcaaa atgatttacc agcattgagc actagctttt caacaagcag tgtgaaaata    180
tctcagccaa aaacagcgaa gtctgcttca aaatctgaat cagataagat tttcgttgat    240
ataaaaggtg ccgtcagaaa agaaggcgtt tatgaattga tatcaggtag tcgtgtgaca    300
gatgtggtca aattagctgg cggttttaca gatgatgcgg ataagaaatc tgttaattta    360
gctgaaaaag tagcggacga atcagtgatt tacgtggcaa gagttggtga agaggtcaca    420
ccagaaagta ccacgtctca aatcaaaaat acagcagcta gtggagcact gcaggatgca    480
gactcagcac aaatcaatct taatactgcg tctttagaag aacttcagac gatttctggc    540
atcggcgcca aacgggctca agacatcatc gattatcgtg ataacaacgg tggattttcg    600
tcagttgatg atttgaaaaa tgtgtcaggt attggtgaga agaccttaga aaaactaaaa    660
gctgaggtga cagttgatta a    681

<210> SEQ ID NO 43
<211> LENGTH: 1131
<212> TYPE: DNA
<213> ORGANISM: Octadecabacter arcticus

<400> SEQUENCE: 43
atgggtggtt gttctcatcg ggtgctcatc gccatgcata tttttctatc cgccttcgac     60
gaagttcctg atccgcgcgc cagtaacgtg cgccacgacc ttggtgaact gctcgttatc    120
gccttcgtgt cggtcttatg tggatcgacc tcctgcgccg agatggccgc atttggccgt    180
gcaaaagaga gccttttcag gaacttcctg aaactcaagc atgccattcc atcgcatgat    240
accttctcgg aggtcttccg gatcatcgac ccgaaggcac tcgatgcggc cttcagtaag    300
gtacttgccg atgtgaccaa gctcctcaaa gacggtgata tcatcgcgat tgacggcaaa    360
gcgttacggg gtgcgcgcga cccgggcgaa agcgcacgga cccgcatgat ggtctcagcc    420
tatgcctcgc ggctgcgcct gacgttggcg acagtacctg ccgaccgagg cacagaactc    480
agcgcggcca tagaggcgct tgagttgatc gatctgcggg gcaaggtggt caccggtgat    540
gcattacatt gcaaccgccg cacggttgcc gcaatcaacg caggcggcgg tgattggtgc    600
ctcgccctca agggtaacca ggaatccctg ttgtctgacg cccgtggatg tttcagcaag    660
gggcacaaaa gcgatccaac agccgttacg gaaaataccg gccatggaag aaaagaaacc    720
cgtaaggcgg tcgtggtatc ggctaaggca ttggcagaat accacgaatt ccctggcctc    780
aaggggttcg gtcgcatcga ggcgaccaga gagatgggcg gaaaggtgac ctcagagacc    840
cgctacttcg cgctgtcttg ggttcccaca cctgaggtgc tgttggccgc tgtccgcgac    900
cattgggcca tcgaaaatgc ccttcattgg cagttggatg tgtctttccg cgaggacgcc    960
```

-continued

```
gcacgcaatc ggaaagacaa cggtcccggc aacatcgccg ttctacgtcg ccgcgcactc    1020
gacgtcctcc ggcgtgacac atccaagggc tctctctcca taaaaatcaa acgtgcaggc    1080
tgggacacca ccttcttacg cagcattctc agtgacttgg caacaacatg a             1131

<210> SEQ ID NO 44
<211> LENGTH: 693
<212> TYPE: DNA
<213> ORGANISM: Psychromonas ingrahamii

<400> SEQUENCE: 44
atgtcccaaa taaccttgat aaaccagctc tcaatcatcc gtgatacccg acaaccgagg      60
aaagtgcatc acaatttagt tgatgtttta tttttggcaa ttacagccgt catatcgggc     120
tgtgagggtt gggaagaaat acaagatttc ggcaacgata agttagattg gctgagaaag     180
tatttaccat tttcaggcgg aatacctacg gacgacacaa tttctcgtat ttttcagttg     240
attgacccaa aagaatttca aaagtgcttt gctacttgga tgaaaagttg ctgtgaaatg     300
agtcatggag atgtcattgt tattgatgga aaaacattaa gaggttcatt taataagaaa     360
gataaatcag atactattca tatggttagt gcttttgcag ccgctaattc ggttgtgtta     420
gggcaagtta agacaaatgc taagtctaat gaaattacag cgattcctaa gttattagat     480
ttattggatg tacgtggatg cctcgtaact attgatgcaa tgggatgcca aactaaaata     540
gctaaaaaaa tcgtagataa aggtggtgat tatctttttc ctgttaaagg taaccaagaa     600
cgattacaaa cagcattaga cggtatattt tcaattggcc gattagagtt accagaaaca     660
gaagtctata cgactaaaaa aaaggcaggg taa                                  693

<210> SEQ ID NO 45
<211> LENGTH: 804
<212> TYPE: DNA
<213> ORGANISM: Shewanella psychrophila

<400> SEQUENCE: 45
atgagccttc ttactcttac taagtacttt gaaattattg aagatcatcg tcaagccact      60
aaagttactt atcccttgtt cgatgtattg tttttaacca tggtagcggt tattgggggc     120
tgcgagggtt gggaagatat tgaagatttt ggccattgtc acttagagtt actcaaaaag     180
tacggggatt ttagcgcagg gatcccagtc catgacacca ttgctagaat tatttgcaaa     240
gtcgacccag aagccctgca acaagcgttt atctcatgga tgcaggcaac cgagcaactg     300
tctcaaggtc aagttattgc cattgatggc aagactttgc gtggctctta taatagagat     360
gatcgtcaat ccgccattca tatggtgaat gctttctctg tcgccaatgg tgtcgtgatg     420
ggacaactta aaacagattc gaagtccaat gagatcactg ctattcctga attattagcc     480
ctattagata ttcaaggagc attggtaacc atcgatgcta tggggactca agccaatatt     540
gcacatacca tcatagacaa gggagcagac ttcctgttag cagtcaaagg caatcaaaat     600
tctttacatc agctagtaaa agaaaccttc gcagatcagc ttgattatgc tgaaaatatc     660
actcaaattg aggcgcagca tggcaggaaa gaatttaggg aataccaaac tattgaggca     720
cctaaggagc tgattgacgc caaatggcca acaatacaaa cctttggaaa agtaattacc     780
tatcgaatag gccttgtttc ctaa                                           804

<210> SEQ ID NO 46
<211> LENGTH: 555
<212> TYPE: DNA
<213> ORGANISM: Thermus sp.
```

```
<400> SEQUENCE: 46
atgaccctac gcgaggcctt gtcccaagtc cccgacccca gggcccgcaa ccggcggtat      60
cccttgtggg gcttgttggc cctcatcttg gtggcctttc tcgcccgcgt ggactccctg     120
cgcggcgtgg aacgtttcgc ccgggccaac cctcacctct tgccccacct gggcctgcgc     180 aacccccccgg gccacaccat cctcaccctc ctccttcacc gtctggaccc aaagaagctc    240
caggaggccc tcctccaggt cttccccgag gtggacctgg gaggggtcct ggtggtggac     300
gggaagcacc tccggggaag cggcaagggg aagagccccc aggtcaggct cgtggaggtc     360
ctggccctgc acctcaagac caccctggcc caggcccggg tggaggggag ggaggaccaa     420
gcgcttctgg agctcctgga ccgcctgggg gcggagggac tcaaagggaa ggtagtggtg     480
ggggacgcgg ggtacctgta cccggaggtg gcggggaagg tggtggaaaa aggggggcat     540
acctcttcgt cctga                                                      555

<210> SEQ ID NO 47
<211> LENGTH: 579
<212> TYPE: DNA
<213> ORGANISM: Meiothermus taiwanensis

<400> SEQUENCE: 47
atgaacttac gcgaagcctt agcctcattg gacgatccac gctaccagaa ccggcgctat      60
ccgctgtggg gggtggtggc attggtgctg gtggcctttg tgtgccgggt ggactccctg     120
cggggtgtgg cccgctttgc ccaagccaat cccttcctgt gtaagcccct gggcttgcgc     180
aaggccccag gacgcagctc aatcgcccag ctcatccgcc gcttggaccc gcaagcgctg     240
ggttcagccc tgcaacaggt ctttcccgaa ctccccttc ccgcctcttt ccctacctct      300
accgctacta cctctgccct ggtcgcggat ggcaaggtct tgcgggggag tgctaaaggc     360
gagagcccgg tggtgcgggt ggtggagctg tggtgtgagc aagcccgcca cagcctggcc     420
caggcccaag tcggtgggcg ggaggatgag gccttgctgg gtctgctgga gcgcatgggg     480
ctggagggtt tagccggtcg ggtggtggtg gccgacgcgg gcttcctcta ccccccgggtg    540 gccgaagcca tccgggctaa gggggggatt acctgctga                            579

<210> SEQ ID NO 48
<211> LENGTH: 555
<212> TYPE: DNA
<213> ORGANISM: Thermus filiformis

<400> SEQUENCE: 48
atgaagctca agagggcctt gaccaagatc cccgacccc gcgcccaaaa ccggcagtac       60
cccctctggg gactcctggg cctcatcctg gtggccttcc tttgccgcgt agactccctt     120
cgcggtgtcg cccgcttcgc ccgcgaaaac cctgagcttc tccccctcct gggcctgcgt     180
aagcccccag gccactacac cgtgaccacc atcctgcacc gcctggaccc tcaggacctt     240
caggaggctt tgcgctccgt cttcccggaa gccgatctcg cagcggtcct cgtcgccgac     300
gggaaggtcc tgaggaacag ccgcaagggg aacgctcccc aggtcaagct ggtggaggtg     360
ctcgcccttc acctgcacac caccctggcc caggcccggg cagaggggag ggagagcgag     420
gcccttctgg agctcctcgg cgcgccttggg gccgagggggc ttgcgggaag gctggtggtg    480
ggggacgcgg gctacctgta cccgaaggtc gcccggaagg tggtggaaaa aggggggact     540
acctcttcgt cctga                                                      555
```

<210> SEQ ID NO 49
<211> LENGTH: 498
<212> TYPE: DNA
<213> ORGANISM: Litorilinea aerophila

<400> SEQUENCE: 49
atgattttag cggtcatgca gggggagaat agtctacggg gcattgcgca atggatgcgg        60
ctacactggg aggaaattgc ggaacccttg aatctctggg cgaccaaagg agcgccctcc       120
tacggcacct tatggaatct gctggccagc ctgaccccca aggagctcaa ccaggttctg       180 caggggggcag aggaaggggg aggttatacg ctggatggca aacatttgcg tgggagcaaa       240
cgccagagcc aagcagccct gcaggtggta accctagcgg gtgccaggta cggccagatc       300
ctggcccaac aggaagtgga ggcgggcaat gagctggcgg cagccttgcg gttgttacag       360
gaggtgcctg tggcgggcaa gctggtgagc atggatgcgg gccttttgca gcgggagacg       420
gtggcaaccg tggcccaaaa aggggggcct acatggggtt cgtcaagggc aaccatgggg       480
ctctctatgc gcttatag                                                     498

<210> SEQ ID NO 50
<211> LENGTH: 741
<212> TYPE: DNA
<213> ORGANISM: Methylobacterium aquaticum

<400> SEQUENCE: 50
gtgatgatcc tggaggtcgg cgtgtccgaa gcactggagg tcggtcctgc cagcctgtgg        60
gaacacctgg ctgccatccc ggatcggcgc ggccgcaaag gcggcagta cggcctgccc       120 gccatcctga ccctgtctct cgccgccatg ctgtcggggg ccaacgatct gcgcgccgtg       180
ttccggtggg gccgacggct gccgcccgag gcgctattcc tgctcggcct ggagcgggcg       240
ccctgccacg ccacgtacca ttacttcttc aaggccctcg acgtggcggc gaccgaggcg       300
gtgctggggg cctgggtgcg cggtgcggcc gaaccggatc agggcctggg tcacgtggcg       360
ctcgatggca aacggctgcg cggctcggct ggcgcggacc acgacggcag cggcggcgcg       420
catctggtgg cggccttcgc catcagattg ggcggggtga tcggccagtt gcaggtggca       480
cccgacgcca acgagatcac ggcggccctg acactgctca aagggctgcc gctgcacggc       540
gccctcgtca ccggcgacgc gatgttctgc cagcgggcga tctgccaggg cctgcgcgac       600
cagcacgggg actatctgtt tgccgtcaaa gccaaccagc ccgagttgat ggctgatctg       660
gctctcgcct tcggcgacgc ctttccccccc ggcgctgctc aaggcgctca agacgagcgg       720
cggcgtccgc ccatccgctg a                                                 741

<210> SEQ ID NO 51
<211> LENGTH: 1110
<212> TYPE: DNA
<213> ORGANISM: Rhodopseudomonas palustris

<400> SEQUENCE: 51
atggagcagc cgatggatcg atttgcggag tgcttcgaag acctgcccga cccgcgggcg        60
ggcaatgcgt tgcacgatct gaccgagatc ttgttcattg ccctgatggc gacgctgtgc       120
ggggcgacca gttgcaccga catggcgctg tttgcgcgga tgaaggccta tctttggcgg       180
gatgtgctgg tcctgaagaa cggccttccg agccacgaca cgttcagtcg ggtgttccgc       240
atgctggacc cggaggcgtt cgagaaggcg ttccaacgct tcatgaaagc ctttgccaaa       300
ggcgccaaga tcaagccgcc gaaaggggtg atcgccctcg acggcaaggc gctgcggcgc       360

-continued

```
ggctacgaaa gcggcagaag ccacatgccg cccgtgatgg tgacggcctg ggcggcgcag      420
acccgcatgg cgctggccaa tgtgcaggcc ccgaacaaca acgaagccgc cggtgccttg      480
caactgatcg aacttctgca gctcaaaggc tgcgtcgtga cggccgatgc gctgcattgc      540
catcgtggca tggccgaagc gatcaaggcc cggggcggcg attatgtgct ggccgtgaag      600
gacaaccagc cagcgctgat gcgggatgcg aaggcggcaa tccgcgccgc cacgcgccag      660
ggcaagccat cgacgatcac cgtcgatgcc ggtcatggac gcaaggaaaa gcgccgtgct      720
gtcgtcgccg ctgtcccgca gatggcgcaa gaccacgact ttgccgggct caaagcggtg      780
gccaggatca ccagcaagcg cggcaccgac aagaccgtcg agcgttactt tctgatgagc      840
caggcctatc cccccaaaga cgtcctgcgc atcgtccgga cccactggac catcgaaaac      900
agcctgcatt ggccgctcga cgtcgtgctc gacgaggact tggcgcgcaa tcgcaaggac      960
aacgcccccg ccaacctcgc cgtgctcaga cgcctggccc tcaacgtcgc aagggcacat     1020
ccagacaaca cccatcgct gcgtggaaag ctgaaacgtg caggatggaa cgatacgttc     1080
ctcttcgaac tcatccaaca catgcgatag                                    1110
```

```
<210> SEQ ID NO 52
<211> LENGTH: 60
<212> TYPE: PRT
<213> ORGANISM: Thermovibrio ammonificans

<400> SEQUENCE: 52

Ser Gly Lys Val Asn Val Asn Ser Ala Gly Lys Lys Leu Leu Met Ala
1               5                   10                  15

Leu Ser Asp Arg Ile Thr Pro Thr Leu Ala Asp Ser Ile Ile Glu Ala
            20                  25                  30

Arg Pro Ile Arg Lys Leu Gln Asp Leu Leu Asp Ile Pro Gly Phe Thr
        35                  40                  45

Arg Glu Leu Tyr Phe Glu Ile Arg Pro Ile Ile Thr
    50                  55                  60
```

```
<210> SEQ ID NO 53
<211> LENGTH: 62
<212> TYPE: PRT
<213> ORGANISM: Aquifex aeolicus

<400> SEQUENCE: 53

Ser Lys Gly Lys Val Asn Ile Asn Thr Ala Pro Leu Leu Val Leu Tyr
1               5                   10                  15

Ser Leu Asp Arg Asp Ile Asp Met Glu Leu Ala Lys Arg Ile Ala Asp
            20                  25                  30

Tyr Arg Lys Glu Lys Pro Phe Lys Gln Leu Lys Asp Leu Leu Met Val
        35                  40                  45

Glu Gly Met Thr Leu Asp Ile Leu Tyr Arg Ile Gln Asn Phe
    50                  55                  60
```

```
<210> SEQ ID NO 54
<211> LENGTH: 63
<212> TYPE: PRT
<213> ORGANISM: Hydrogenobacter thermophilus

<400> SEQUENCE: 54

Ser Ser Gly Lys Ile Asn Ile Asn Thr Ala Asn Ser Tyr Ile Leu Met
1               5                   10                  15

Ala Leu Asp Pro Arg Ile Asp Gln Ala Leu Ala Ser Lys Ile Ile Glu
```

-continued

```
                20              25              30

Arg Arg Asn Arg Glu Pro Phe Lys Lys Val Glu Asp Leu Leu Leu Val
        35              40              45

Asp Gly Phe Thr Phe Asp Ile Leu Tyr Ala Ile Lys Asn Leu Val
    50              55              60

<210> SEQ ID NO 55
<211> LENGTH: 63
<212> TYPE: PRT
<213> ORGANISM: Thermocrinis albus

<400> SEQUENCE: 55

Ser Ser Gly Lys Ile Asn Val Asn Thr Ala Pro Leu Tyr Val Leu Met
1               5               10              15

Ala Leu Asp Asp Arg Ile Asp Glu Asp Leu Ala Arg Arg Ile Ile Glu
            20              25              30

Arg Arg Asp Lys Glu Pro Phe Arg Arg Val Glu Asp Leu Leu Leu Val
        35              40              45

Glu Gly Phe Thr Leu Asp Ile Leu Tyr Ser Val Arg Asp Leu Val
    50              55              60

<210> SEQ ID NO 56
<211> LENGTH: 54
<212> TYPE: PRT
<213> ORGANISM: Ferroglobus placidus

<400> SEQUENCE: 56

Leu Asp Val Asn Lys Ala Lys Leu Tyr Gln Leu Glu Ser Ile Pro Gly
1               5               10              15

Ile Gly Lys Thr Thr Ala Ala Lys Ile Ile Ser Ala Lys Pro Phe Arg
            20              25              30

Ser Leu Lys Glu Leu Lys Asp Leu Ile Gly Glu Glu Lys Phe Lys Ile
        35              40              45

Leu Leu Pro Tyr Ile Ser
    50

<210> SEQ ID NO 57
<211> LENGTH: 53
<212> TYPE: PRT
<213> ORGANISM: Aciduliprofundum boonei

<400> SEQUENCE: 57

Ile Asn Val Cys Pro Leu Glu Glu Leu Leu Ser Thr Ser Leu Ile Gly
1               5               10              15

Lys Lys Leu Ala Ile Arg Ile Met Glu Asn Arg Pro Tyr Glu Ser Met
            20              25              30

Glu Glu Leu Arg Lys Val Arg Gly Ile Gly Glu Lys Arg Leu Ser Arg
        35              40              45

Leu Gln Ala Arg Phe
    50

<210> SEQ ID NO 58
<211> LENGTH: 53
<212> TYPE: PRT
<213> ORGANISM: Archaeoglobus veneficus

<400> SEQUENCE: 58

Glu Ile Leu Asp Val Asn Arg Ala Ser Leu Gln Gln Leu Glu Ala Ile
1               5               10              15
```

```
Pro Gly Ile Gly Lys Ala Thr Ala Ala Lys Ile Val Ala Asn Arg Pro
        20                  25                  30

Phe Arg Asn Val Glu Glu Ile Ala Ser Leu Val Glu Asn Phe Asp Glu
        35                  40                  45

Ile Lys Asp Phe Phe
    50

<210> SEQ ID NO 59
<211> LENGTH: 52
<212> TYPE: PRT
<213> ORGANISM: Archaeoglobus profundus

<400> SEQUENCE: 59

Leu Asn Pro Asn Thr Ala Lys Leu Tyr Gln Leu Glu Ala Val Pro Gly
1               5                  10                  15

Ile Gly Lys Ala Leu Ala Gly Lys Ile Ile Ala Asn Arg Pro Tyr Ser
        20                  25                  30

Ser Leu Asp Glu Leu Arg Asp Val Leu Gly Asp Val Phe Asp Arg Val
        35                  40                  45

Lys His Phe Phe
    50

<210> SEQ ID NO 60
<211> LENGTH: 38
<212> TYPE: PRT
<213> ORGANISM: Thermotoga maritima

<400> SEQUENCE: 60

Ile Asn Ser Met Ser Leu Glu Glu Leu Thr Ala Ile Pro Gly Ile Gly
1               5                  10                  15

Ser Ala Leu Ala Arg Lys Ile Ile Leu Asn Arg Pro Phe Arg Ser Trp
        20                  25                  30

Glu Asp Leu Lys Lys Val
        35

<210> SEQ ID NO 61
<211> LENGTH: 38
<212> TYPE: PRT
<213> ORGANISM: Thermotoga maritima

<400> SEQUENCE: 61

Ile Asn Ser Met Ser Leu Glu Glu Leu Thr Ala Ile Pro Gly Ile Gly
1               5                  10                  15

Ser Ala Leu Ala Arg Lys Ile Ile Leu Asn Arg Pro Phe Arg Ser Trp
        20                  25                  30

Glu Asp Leu Lys Lys Val
        35

<210> SEQ ID NO 62
<211> LENGTH: 49
<212> TYPE: PRT
<213> ORGANISM: Thermotoga naphthophila

<400> SEQUENCE: 62

Ile Asn Ser Met Ser Leu Glu Glu Leu Thr Ala Ile Pro Gly Ile Gly
1               5                  10                  15

Asn Ala Leu Ala Lys Lys Ile Ile Leu Asn Arg Pro Phe Arg Ser Trp
        20                  25                  30

Glu Asp Leu Lys Lys Val Val Pro Ala Glu Thr Val Asn Phe Leu Arg
        35                  40                  45
```

-continued

Lys

<210> SEQ ID NO 63
<211> LENGTH: 38
<212> TYPE: PRT
<213> ORGANISM: Thermotoga sp.

<400> SEQUENCE: 63

Ile Asn Ser Met Ser Leu Glu Glu Leu Thr Ala Ile Pro Gly Ile Gly
1               5                   10                  15

Asn Ala Leu Ala Arg Lys Ile Ile Leu Asn Arg Pro Phe Arg Ser Trp
            20                  25                  30

Glu Asp Leu Lys Lys Val
        35

<210> SEQ ID NO 64
<211> LENGTH: 41
<212> TYPE: PRT
<213> ORGANISM: Aciduliprofundum boonei

<400> SEQUENCE: 64

Pro Leu Asn Val Asn Ser Ala Ser Phe Ser Thr Leu Lys Ser Ile Pro
1               5                   10                  15

Gly Met Gly Glu Lys Lys Ala Ala Glu Ile Ile Arg Lys Arg Pro Phe
            20                  25                  30

Lys Asn Met Lys Ser Leu Gln Glu Ile
        35                  40

<210> SEQ ID NO 65
<211> LENGTH: 40
<212> TYPE: PRT
<213> ORGANISM: Thermovibrio ammonificans

<400> SEQUENCE: 65

Pro Leu Asn Val Asn Glu Ala Ser Val Lys Leu Leu Ser Phe Ile Pro
1               5                   10                  15

Gly Ile Ser Arg Lys Thr Ala Ser Asp Ile Val Leu Arg Arg Pro Phe
            20                  25                  30

Lys Ser Lys Glu Glu Leu Leu Lys
        35                  40

<210> SEQ ID NO 66
<211> LENGTH: 55
<212> TYPE: PRT
<213> ORGANISM: Thermococcus gammatolerans

<400> SEQUENCE: 66

Val Pro Ile Asn Val Asn Arg Glu Ser Pro Lys Val Leu Gln Leu Ile
1               5                   10                  15

Pro Gly Ile Gly Lys Lys Thr Ala Thr Arg Ile Leu Ala Lys Arg Pro
            20                  25                  30

Phe Arg Ser Arg Glu Glu Phe Phe Glu Val Val Asp Pro Gly Val Arg
        35                  40                  45

Glu Val Leu Lys Asp Leu Val
    50                  55

<210> SEQ ID NO 67
<211> LENGTH: 56
<212> TYPE: PRT
<213> ORGANISM: Thermococcus cleftensis -continued

<400> SEQUENCE: 67

Ile Pro Val Asp Ile Asn Arg Glu Ser Pro Lys Leu Leu Gln Tyr Leu
1               5                   10                  15

Pro Gly Ile Gly Lys Lys Thr Ala Val Lys Ile Leu Ser Lys Arg Pro
            20                  25                  30

Phe Lys Asn Lys Asp Glu Phe Phe Ser Val Val Gly Glu Asp Lys Arg
        35                  40                  45

Glu Met Leu Gly Gly Ile Ile Arg
    50                  55

<210> SEQ ID NO 68
<211> LENGTH: 70
<212> TYPE: PRT
<213> ORGANISM: Moorella thermoacetica

<400> SEQUENCE: 68

Glu Arg Ile Asp Leu Gln Lys Ala Asp Ala Ser Arg Phe Leu Val Glu
1               5                   10                  15

Pro Gly Lys Leu Leu Pro Pro Leu Ala Ala Leu Pro Gly Val Gly Arg
            20                  25                  30

Ala Ala Ala Glu Ala Ile Val Arg Ala Arg Gln Glu Arg Pro Phe Thr
        35                  40                  45

Ser Val Glu Asp Leu Gln Tyr Arg Ser Arg Val Ser Lys Thr Val Ile
    50                  55                  60

Glu Ala Leu Glu Lys His
65                  70

<210> SEQ ID NO 69
<211> LENGTH: 44
<212> TYPE: PRT
<213> ORGANISM: Symbiobacterium thermophilum

<400> SEQUENCE: 69

Leu Pro Gly Leu Gly Asp Ser Ala Ala Gln Ala Ile Val Glu Ala Arg
1               5                   10                  15

Ala Gln Gly Pro Phe His Ser Lys Glu Asp Leu Lys Asn Arg Ala Arg
            20                  25                  30

Leu Asn Lys Ala Val Met Glu Leu Leu Glu Gly His
        35                  40

<210> SEQ ID NO 70
<211> LENGTH: 59
<212> TYPE: PRT
<213> ORGANISM: Sulfurihydrogenibium sp.

<400> SEQUENCE: 70

Asn Asp Leu Lys Ile Asp Ile Asn Thr Ala Asp Ile Ile Thr Leu Gln
1               5                   10                  15

Arg Ile Pro Tyr Ile Gly Glu Lys Thr Ala Glu Leu Ile Ile Lys Asp
            20                  25                  30

Arg Lys Ile Arg Gly Gly Tyr Thr Asp Ile Asn Gln Leu Lys Trp Val
        35                  40                  45

Lys Asn Phe Asp Lys Ile Lys Pro Tyr Ile Lys
    50                  55

<210> SEQ ID NO 71
<211> LENGTH: 59
<212> TYPE: PRT

<213> ORGANISM: Dictyoglomus thermophilum

<400> SEQUENCE: 71

Pro Gln Phe Phe Pro Ile Glu Ile Asn Lys Ala Thr Tyr Glu Gln Leu
1               5                   10                  15

Leu Arg Ile Pro Gly Ile Gly Pro Ile Ser Ala Lys Lys Ile Ile Lys
            20                  25                  30

Ala Arg Lys Glu Gln Lys Ile Arg Asp Ile Lys Asp Leu Lys Lys Leu
        35                  40                  45

Gly Ile Gln Val Glu Arg Cys Lys Asn Tyr Ile
    50                  55

<210> SEQ ID NO 72
<211> LENGTH: 37
<212> TYPE: PRT
<213> ORGANISM: Thermodesulfatator indicus

<400> SEQUENCE: 72

Pro Gln Phe Phe Pro Val Asp Val Asn Arg Ala Ser Tyr Arg Glu Leu
1               5                   10                  15

Leu Arg Val Pro Gly Ile Gly Pro Thr Ile Ala Arg Arg Ile Leu Glu
            20                  25                  30

Ala Arg Lys Glu Gly
        35

<210> SEQ ID NO 73
<211> LENGTH: 65
<212> TYPE: PRT
<213> ORGANISM: Kosmotoga sp.

<400> SEQUENCE: 73

Val Asn Tyr Val Gly Val Asn Leu Asn Thr Ala Ser Glu His Leu Leu
1               5                   10                  15

Lys Tyr Ile Ser Gly Leu Asn Ala Arg Met Ala Arg Asn Ile Val Glu
            20                  25                  30

Tyr Arg Lys Gln Val Gly Leu Phe Lys Lys Arg Glu Asp Leu Leu Lys
        35                  40                  45

Val Lys Gly Ile Gly Asn Lys Ala Phe Glu Gln Ala Ala Gly Phe Cys
    50                  55                  60

Arg
65

<210> SEQ ID NO 74
<211> LENGTH: 65
<212> TYPE: PRT
<213> ORGANISM: Marinitoga sp.

<400> SEQUENCE: 74

Val Asn Leu Val Gly Val Asn Leu Asn Thr Ala Ser Ala Ala Leu Leu
1               5                   10                  15

Gln Tyr Ile Ser Gly Ile Thr Pro Lys Leu Ala Glu Asn Ile Val Lys
            20                  25                  30

Tyr Arg Glu Glu Asn Gly Phe Phe Lys Glu Arg Lys Glu Leu Leu Lys
        35                  40                  45

Val Lys Gly Phe Gly Pro Lys Ala Phe Glu Gln Ala Ala Gly Phe Leu
    50                  55                  60

Arg
65

-continued

<210> SEQ ID NO 75
<211> LENGTH: 65
<212> TYPE: PRT
<213> ORGANISM: Thermosipho africanus

<400> SEQUENCE: 75

Val Asn Met Val Gly Val Asn Leu Asn Thr Ala Ser Ala Lys Leu Leu
1               5                   10                  15

Glu Tyr Val Ser Gly Ile Thr Pro Ser Leu Ala Lys Lys Ile Val Lys
            20                  25                  30

Tyr Arg Glu Lys His Gly Lys Phe Ile Glu Arg Asn Gln Leu Leu Asn
        35                  40                  45

Ile Glu Gly Leu Gly Glu Lys Thr Phe Glu Gln Cys Ala Gly Phe Leu
    50                  55                  60

Arg
65

<210> SEQ ID NO 76
<211> LENGTH: 65
<212> TYPE: PRT
<213> ORGANISM: Thermosipho melanesiensis

<400> SEQUENCE: 76

Val Asn Gln Leu Gly Ile Asp Leu Asn Ser Ala Ser Ser Lys Leu Leu
1               5                   10                  15

Glu His Val Ala Gly Ile Thr Pro Ser Leu Ala Lys Lys Ile Val Asn
            20                  25                  30

Phe Arg Lys Lys Ile Gly Lys Phe Thr Glu Arg Lys Gln Leu Leu Glu
        35                  40                  45

Ile Glu Gly Leu Gly Gln Lys Thr Tyr Thr Gln Cys Ala Gly Phe Leu
    50                  55                  60

Arg
65

<210> SEQ ID NO 77
<211> LENGTH: 65
<212> TYPE: PRT
<213> ORGANISM: Thermobifida fusca

<400> SEQUENCE: 77

Val Asn Ala Val Gly Val Asp Val Asn Thr Ala Ser Val Pro Leu Leu
1               5                   10                  15

Ser Arg Val Ser Gly Ile Thr Ala Ser Leu Ala Gln Asn Ile Val Ala
            20                  25                  30

Tyr Arg Asp Ala Asn Gly Pro Phe Arg Thr Arg Ala Gln Leu Arg Glu
        35                  40                  45

Val Pro Arg Leu Gly Pro Lys Ala Phe Glu Gln Cys Ala Gly Phe Leu
    50                  55                  60

Arg
65

<210> SEQ ID NO 78
<211> LENGTH: 65
<212> TYPE: PRT
<213> ORGANISM: Symbiobacterium thermophilum

<400> SEQUENCE: 78

Val Asn Ala Val Gly Val Asp Leu Asn Thr Ala Ser Pro Ser Leu Leu
1               5                   10                  15

-continued

```
Gln Tyr Val Ala Gly Ile Lys Ala Ser Val Ala Arg Ala Ile Val Glu
            20                  25                  30

Tyr Arg Glu Lys His Gly Lys Phe Arg Ser Arg Arg Glu Leu Leu Lys
        35                  40                  45

Val Ser Gly Leu Gly Pro Lys Ala Phe Glu Gln Cys Ala Gly Phe Leu
    50                  55                  60

Arg
65

<210> SEQ ID NO 79
<211> LENGTH: 65
<212> TYPE: PRT
<213> ORGANISM: Hungateiclostridium thermocellum

<400> SEQUENCE: 79

Val Asn Ser Val Gly Val Asp Leu Asn Thr Ala Ser Pro Ser Leu Leu
1               5                   10                  15

Ser Tyr Ile Ser Gly Ile Asn Ser Val Ile Ala Lys Asn Ile Val Glu
            20                  25                  30

Tyr Arg Glu Thr Asn Gly Lys Phe Lys Arg Arg Glu Glu Leu Lys Lys
        35                  40                  45

Val Lys Lys Leu Gly Asp Lys Thr Phe Glu Gln Cys Ala Gly Phe Leu
    50                  55                  60

Arg
65

<210> SEQ ID NO 80
<211> LENGTH: 65
<212> TYPE: PRT
<213> ORGANISM: Thermoanaerobacterium xylanolyticum

<400> SEQUENCE: 80

Val Asn Ser Val Gly Val Asp Leu Asn Thr Ala Ser Val Ser Leu Leu
1               5                   10                  15

Lys Tyr Val Ala Gly Ile Asn Gly Thr Ile Ala Lys Asn Ile Val Glu
            20                  25                  30

Tyr Arg Asn Thr Val Gly Lys Phe Arg Asn Arg Asn Glu Leu Lys Lys
        35                  40                  45

Val Lys Arg Leu Gly Glu Gly Thr Phe Thr Gln Cys Ala Gly Phe Leu
    50                  55                  60

Arg
65

<210> SEQ ID NO 81
<211> LENGTH: 65
<212> TYPE: PRT
<213> ORGANISM: Thermoanaerobacterium thermosaccharolyticum

<400> SEQUENCE: 81

Val Asn Ser Val Gly Val Asp Leu Asn Thr Ala Ser Val Ser Leu Leu
1               5                   10                  15

Lys Tyr Val Ser Gly Ile Asn Ala Ser Ile Ala Lys Asn Ile Val Glu
            20                  25                  30

Tyr Arg Asn Glu Val Gly Gln Phe Arg Asn Arg Asn Glu Leu Lys Asn
        35                  40                  45

Val Lys Arg Leu Gly Asp Ala Thr Phe Thr Gln Cys Ala Gly Phe Leu
    50                  55                  60
```

```
Arg
65

<210> SEQ ID NO 82
<211> LENGTH: 65
<212> TYPE: PRT
<213> ORGANISM: Thermoanaerobacter sp.

<400> SEQUENCE: 82

Val Asn Ser Val Gly Val Asp Leu Asn Thr Ala Ser Val Ser Leu Leu
1               5                   10                  15

Lys Tyr Val Ser Gly Ile Asn Ala Ala Ile Ala Lys Asn Ile Val Glu
            20                  25                  30

Tyr Arg Asn Gln Ile Gly Lys Phe Thr Asn Arg Glu Gln Leu Lys Asn
        35                  40                  45

Val Lys Arg Leu Gly Asp Thr Thr Phe Thr Gln Cys Ala Gly Phe Leu
    50                  55                  60

Arg
65

<210> SEQ ID NO 83
<211> LENGTH: 65
<212> TYPE: PRT
<213> ORGANISM: Thermoanaerobacter mathranii

<400> SEQUENCE: 83

Val Asn Ser Val Gly Val Asp Leu Asn Thr Ala Ser Val Ser Leu Leu
1               5                   10                  15

Lys Tyr Val Ser Gly Ile Asn Thr Ala Ile Ala Lys Asn Ile Val Glu
            20                  25                  30

Tyr Arg Asn Gln Ile Gly Lys Phe Thr Ser Arg Glu Gln Leu Lys Asn
        35                  40                  45

Val Lys Arg Leu Gly Glu Ala Thr Phe Thr Gln Cys Ala Gly Phe Leu
    50                  55                  60

Arg
65

<210> SEQ ID NO 84
<211> LENGTH: 65
<212> TYPE: PRT
<213> ORGANISM: Thermoanaerobacter italicus

<400> SEQUENCE: 84

Val Asn Ser Val Gly Val Asp Leu Asn Thr Ala Ser Val Ser Leu Leu
1               5                   10                  15

Lys Tyr Val Ser Gly Ile Asn Thr Val Ile Ala Lys Asn Ile Val Glu
            20                  25                  30

Tyr Arg Asn Gln Ile Gly Lys Phe Thr Ser Arg Glu Gln Leu Lys Asn
        35                  40                  45

Val Lys Arg Leu Gly Glu Ala Thr Phe Thr Gln Cys Ala Gly Phe Leu
    50                  55                  60

Arg
65

<210> SEQ ID NO 85
<211> LENGTH: 60
<212> TYPE: PRT
<213> ORGANISM: Meiothermus ruber

<400> SEQUENCE: 85
```

-continued

```
Lys Ile Ala Pro Val His Ile Asn Thr Ala Thr Leu Ala Gln Leu Glu
1               5                   10                  15

Thr Leu Pro Gly Ile Gly Pro Lys Leu Ala Gln Glu Ile Ile Lys His
            20                  25                  30

Arg Pro Tyr Lys Asn Ala His Asp Leu Gln Ser Lys Val Lys Gly Ile
        35                  40                  45

Ser Pro Ser Leu Trp Lys Lys Ile Ala Pro His Val
    50                  55                  60

<210> SEQ ID NO 86
<211> LENGTH: 65
<212> TYPE: PRT
<213> ORGANISM: Ammonifex degensii

<400> SEQUENCE: 86

Ser Ser Gly Gly Lys Ile Asn Leu Asn Thr Ala Asp Glu Ala Ala Leu
1               5                   10                  15

Gln Thr Leu Pro Gly Ile Gly Pro Thr Leu Ala Arg Arg Ile Val Glu
            20                  25                  30

Tyr Arg Ala Lys Asn Gly Pro Phe Thr Ser Val Glu Asp Leu Ala Lys
        35                  40                  45

Val Pro Gly Ile Gly Pro Arg Arg Leu Glu Gln Leu Arg Glu Tyr Val
    50                  55                  60

Cys
65

<210> SEQ ID NO 87
<211> LENGTH: 61
<212> TYPE: PRT
<213> ORGANISM: Thermobifida fusca

<400> SEQUENCE: 87

Arg Ile Asp Leu Asn Thr Ala Thr Ala Asp Gln Leu Gln Thr Leu Pro
1               5                   10                  15

Gly Ile Gly Pro Val Leu Ala Gln Arg Ile Ile Asp His Arg Ala Ser
            20                  25                  30

Ile Gly Gly Phe Thr Ser Val Glu Gln Leu His Asp Val Thr Gly Ile
        35                  40                  45

Gly Asp Arg Arg Phe Ala Glu Leu Arg Asp Leu Val Tyr
    50                  55                  60

<210> SEQ ID NO 88
<211> LENGTH: 60
<212> TYPE: PRT
<213> ORGANISM: Thermosynechococcus sp.

<400> SEQUENCE: 88

Arg Val Asn Leu Asn Thr Ala Thr Ala Ala Glu Leu Glu Thr Leu Pro
1               5                   10                  15

Gly Val Gly Pro Lys Leu Ala Ala Glu Ile Ile Arg Ala Arg Glu Gln
            20                  25                  30

Lys Pro Phe Asn Ser Leu Ala Asp Leu Asp Ala Val Pro Gly Val Gly
        35                  40                  45

Pro Lys Leu Leu Glu Arg Leu Arg Asp Arg Val Thr
    50                  55                  60

<210> SEQ ID NO 89
<211> LENGTH: 60
```

-continued

```
<212> TYPE: PRT
<213> ORGANISM: Thermosynechococcus elongatus

<400> SEQUENCE: 89

Arg Val Asn Leu Asn Thr Ala Thr Ala Ala Glu Leu Glu Thr Leu Pro
1               5                   10                  15

Gly Val Gly Ser Lys Leu Ala Ala Glu Ile Ile Arg Ala Arg Glu His
            20                  25                  30

Lys Pro Phe Gln Ser Leu Ala Asp Leu Asp Ala Val Pro Gly Val Gly
        35                  40                  45

Pro Lys Leu Leu Glu Arg Leu Arg Asp Arg Val Thr
    50                  55                  60

<210> SEQ ID NO 90
<211> LENGTH: 58
<212> TYPE: PRT
<213> ORGANISM: Meiothermus ruber

<400> SEQUENCE: 90

Gln Lys Val Asn Leu Asn Thr Ala Ser Gln Ala Glu Ile Glu Ser Leu
1               5                   10                  15

Pro Gly Ile Gly Pro Ala Leu Ala Gln Arg Ile Ile Glu Gly Arg Pro
            20                  25                  30

Tyr Arg Thr Leu Glu Asp Leu Glu Arg Val Lys Gly Ile Gly Pro Lys
        35                  40                  45

Leu Leu Glu Arg Leu Arg Pro Leu Val Thr
    50                  55

<210> SEQ ID NO 91
<211> LENGTH: 60
<212> TYPE: PRT
<213> ORGANISM: Marinithermus hydrothermalis

<400> SEQUENCE: 91

Pro Ser Arg Val Lys Val Ser Leu Asn Arg Ala Thr Leu Glu Glu Leu
1               5                   10                  15

Glu Ala Leu Pro Gly Ile Gly Pro Thr Lys Ala Arg Arg Ile Met Glu
            20                  25                  30

Tyr Arg Pro Tyr Leu Arg Val Glu Asp Leu Leu Arg Val Pro Gly Ile
        35                  40                  45

Gly Glu Lys Thr Leu Glu Arg Leu Arg Pro Tyr Val
    50                  55                  60

<210> SEQ ID NO 92
<211> LENGTH: 56
<212> TYPE: PRT
<213> ORGANISM: Thermus sp.

<400> SEQUENCE: 92

Ile Ser Leu Asn Arg Ala Ser Leu Glu Glu Leu Glu Ala Leu Pro Gly
1               5                   10                  15

Ile Gly Pro Thr Leu Ala Arg Arg Ile Val Glu Gly Arg Pro Tyr Gly
            20                  25                  30

Lys Val Glu Asp Leu Leu Arg Val Lys Gly Ile Gly Pro Ala Thr Leu
        35                  40                  45

Glu Arg Leu Arg Pro Tyr Val Arg
    50                  55

<210> SEQ ID NO 93
```

<211> LENGTH: 213
<212> TYPE: PRT
<213> ORGANISM: Kosmotoga sp.

<400> SEQUENCE: 93

```
Pro Ile Asp Leu Asn Thr Ala Thr Val Glu Ile Leu Gln Leu Leu Pro
1               5                   10                  15

Gly Ile Gly Glu Thr Arg Ala Lys Ala Ile Val Thr Phe Arg Glu Ser
            20                  25                  30

Asn Gly Gly Phe Ser Ser Thr Glu Glu Leu Leu Gln Val Lys Gly Ile
            35                  40                  45

Gly Asn Ser Thr Tyr Glu Lys Leu Lys Asp Leu Val Thr Ile Thr Asn
    50                  55                  60

Ala Ala Lys Ser Lys Ala Glu Asn Thr Arg Asp Thr Arg Leu Asp Leu
65                  70                  75                  80

Asn Thr Ala Ser Lys Val Asp Leu Thr Ser Leu Pro Gly Ile Gly Glu
                85                  90                  95

Val Lys Ala Ala Glu Ile Val Lys Tyr Arg Glu Glu His Gly Gly Phe
            100                 105                 110

Lys Ala Ile Asp Glu Leu Ile Asn Val Lys Gly Ile Gly Arg Ala Thr
            115                 120                 125

Leu Asp Lys Ile Arg Asn Leu Val Arg Val Gly Ser Val Ser Thr Asn
    130                 135                 140

Val Pro Asp Lys Ser Glu Asn Ser Gly Lys Ile Asn Val Asn Thr Ala
145                 150                 155                 160

Thr Leu Gln Glu Leu Val Ala Leu Pro Gly Ile Gly Pro Val Leu Ala
                165                 170                 175

Glu Arg Ile Ile Asp Tyr Arg Glu His Asn Gly Lys Phe His Lys Pro
            180                 185                 190

Glu Asp Leu Leu Lys Val Ser Gly Ile Gly Ile Lys Thr Leu Ser Lys
            195                 200                 205

Phe Arg Glu Met Ile
    210
```

<210> SEQ ID NO 94
<211> LENGTH: 61
<212> TYPE: PRT
<213> ORGANISM: Thermaerobacter marianensis

<400> SEQUENCE: 94

```
Arg Ile Asp Ile Asn Arg Ala Ser Ala Ala Glu Leu Glu Ala Leu Pro
1               5                   10                  15

Gly Ile Gly Pro Ala Leu Ala Gln Arg Ile Val Ala Asp Arg Glu Val
            20                  25                  30

Asn Gly Pro Phe Arg Arg Pro Gln Asp Leu Ser Arg Val Thr Gly Ile
            35                  40                  45

Gly Glu Lys Thr Leu Ala Arg Leu Leu Pro Tyr Ile Thr
    50                  55                  60
```

<210> SEQ ID NO 95
<211> LENGTH: 61
<212> TYPE: PRT
<213> ORGANISM: Thermosediminibacter oceani

<400> SEQUENCE: 95

```
Arg Ile Asn Ile Asn Thr Ala Gly Leu Glu Glu Leu Asp Lys Leu Pro
1               5                   10                  15
```

```
Gly Ile Gly Pro Ala Leu Ala Gln Arg Ile Ile Asp Tyr Arg Asn Gln
            20                  25                  30

His Gly Pro Phe Lys Ser Val Glu Glu Leu Lys Asn Val Ser Gly Ile
        35                  40                  45

Gly Glu Lys Lys Phe Glu Glu Leu Lys Asp Leu Val Lys
    50                  55                  60
```

<210> SEQ ID NO 96
<211> LENGTH: 63
<212> TYPE: PRT
<213> ORGANISM: Moorella thermoacetica

<400> SEQUENCE: 96

```
Gly Gly Lys Val Asn Ile Asn Thr Ala Gly Leu Ala Glu Leu Asp Ser
1               5                   10                  15

Leu Pro Gly Ile Gly Pro Thr Leu Ala Gln Arg Ile Leu Asp Tyr Arg
            20                  25                  30

Thr Gln Lys Gly Pro Phe Arg Thr Ile Glu Asp Leu Gln Asn Val Ser
        35                  40                  45

Gly Ile Gly Ala Lys Lys Phe Ala Asp Leu Lys Asp Leu Ile Thr
    50                  55                  60
```

<210> SEQ ID NO 97
<211> LENGTH: 61
<212> TYPE: PRT
<213> ORGANISM: Hungateiclostridium thermocellum

<400> SEQUENCE: 97

```
Lys Ile Asn Ile Asn Thr Ala Thr Val Glu Glu Leu Asp Ser Leu Pro
1               5                   10                  15

Gly Ile Gly Pro Ala Ile Ala Ala Lys Ile Val Ala Tyr Arg Glu Gln
            20                  25                  30

Asn Gly Lys Phe Lys Ser Ile Glu Asp Ile Met Asn Val Ser Gly Ile
        35                  40                  45

Gly Gln Ser Lys Phe Asn Asn Ile Lys Asp Phe Ile Thr
    50                  55                  60
```

<210> SEQ ID NO 98
<211> LENGTH: 65
<212> TYPE: PRT
<213> ORGANISM: Dictyoglomus turgidum

<400> SEQUENCE: 98

```
Ser Lys Ser Asp Lys Val Asn Ile Asn Thr Ala Ser Lys Glu Glu Leu
1               5                   10                  15

Glu Ser Leu Pro Gly Ile Gly Pro Thr Leu Ala Gln Arg Ile Ile Glu
            20                  25                  30

Tyr Arg Glu Glu Asn Gly Pro Phe Gly Ser Ala Glu Asp Leu Leu Asn
        35                  40                  45

Val Lys Gly Ile Gly Glu Lys Lys Leu Glu Arg Ile Arg Asp Gln Ile
    50                  55                  60

Thr
65
```

<210> SEQ ID NO 99
<211> LENGTH: 64
<212> TYPE: PRT
<213> ORGANISM: Dictyoglomus thermophilum

<400> SEQUENCE: 99

-continued

```
Lys Lys Gly Lys Val Asn Ile Asn Thr Ala Ser Lys Glu Glu Leu Glu
1               5                   10                  15

Ser Leu Pro Gly Ile Gly Pro Thr Leu Ala Gln Arg Ile Ile Glu Tyr
            20                  25                  30

Arg Glu Glu Asn Gly Val Phe Thr Ser Ala Glu Asp Leu Leu Asn Val
        35                  40                  45

Lys Gly Ile Gly Glu Lys Lys Leu Glu Lys Ile Lys Asp Gln Ile Thr
    50                  55                  60
```

<210> SEQ ID NO 100
<211> LENGTH: 63
<212> TYPE: PRT
<213> ORGANISM: Caldicellulosiruptor obsidiansis

<400> SEQUENCE: 100

```
Glu Gly Lys Ile Asn Ile Asn Thr Ala Thr Lys Glu Glu Leu Lys Thr
1               5                   10                  15

Leu Asp Arg Ile Gly Asp Lys Leu Ala Glu Arg Ile Ile Glu Tyr Arg
            20                  25                  30

Gln Asn His Gly Pro Phe Lys Ser Ile Glu Glu Ile Lys Asn Val Asn
        35                  40                  45

Gly Ile Gly Glu Lys Ile Phe Glu Ser Ile Lys Asp Phe Ile Thr
    50                  55                  60
```

<210> SEQ ID NO 101
<211> LENGTH: 63
<212> TYPE: PRT
<213> ORGANISM: Caldicellulosiruptor lactoaceticus

<400> SEQUENCE: 101

```
Glu Gly Lys Ile Asn Ile Asn Thr Ala Thr Lys Glu Glu Leu Lys Thr
1               5                   10                  15

Leu Asp Arg Ile Gly Asp Lys Leu Ala Glu Arg Ile Ile Glu Tyr Arg
            20                  25                  30

Gln Lys His Gly Pro Phe Lys Ser Ile Glu Glu Ile Lys Asn Val Asn
        35                  40                  45

Gly Ile Gly Glu Lys Ile Phe Glu Ser Ile Lys Asp Ser Ile Thr
    50                  55                  60
```

<210> SEQ ID NO 102
<211> LENGTH: 63
<212> TYPE: PRT
<213> ORGANISM: Caldicellulosiruptor kristjanssonii

<400> SEQUENCE: 102

```
Glu Gly Lys Ile Asn Ile Asn Thr Ala Thr Lys Glu Glu Leu Lys Thr
1               5                   10                  15

Leu Asp Arg Ile Gly Asp Lys Leu Ala Glu Arg Ile Ile Glu Tyr Arg
            20                  25                  30

Gln Lys His Gly Pro Phe Lys Ser Ile Glu Glu Ile Lys Asn Val Asn
        35                  40                  45

Gly Ile Gly Glu Lys Ile Phe Glu Ser Ile Lys Asp Ser Ile Thr
    50                  55                  60
```

<210> SEQ ID NO 103
<211> LENGTH: 63
<212> TYPE: PRT
<213> ORGANISM: Caldicellulosiruptor hydrothermalis

<400> SEQUENCE: 103

```
Glu Gly Lys Ile Asn Ile Asn Thr Ala Thr Lys Glu Glu Leu Lys Thr
1               5                   10                  15

Leu Asp Arg Ile Gly Asp Lys Leu Ala Glu Arg Ile Ile Glu Tyr Arg
            20                  25                  30

Gln Lys His Gly Pro Phe Lys Ser Ile Glu Glu Ile Lys Asn Val Asn
        35                  40                  45

Gly Ile Gly Glu Lys Ile Phe Glu Ser Ile Lys Asp Ser Ile Thr
    50                  55                  60
```

<210> SEQ ID NO 104
<211> LENGTH: 63
<212> TYPE: PRT
<213> ORGANISM: Caldicellulosiruptor owensensis

<400> SEQUENCE: 104

```
Glu Gly Lys Ile Asn Ile Asn Thr Ala Thr Lys Glu Glu Leu Lys Thr
1               5                   10                  15

Leu Asp Arg Ile Gly Asp Lys Leu Ala Glu Arg Ile Ile Glu Tyr Arg
            20                  25                  30

Gln Lys His Gly Pro Phe Lys Ser Ile Glu Glu Ile Lys Asn Val Asn
        35                  40                  45

Gly Ile Gly Glu Lys Ile Phe Glu Ser Ile Lys Asp Ser Ile Thr
    50                  55                  60
```

<210> SEQ ID NO 105
<211> LENGTH: 61
<212> TYPE: PRT
<213> ORGANISM: Caldicellulosiruptor bescii

<400> SEQUENCE: 105

```
Lys Ile Asn Ile Asn Thr Ala Thr Lys Glu Glu Leu Lys Thr Leu Asn
1               5                   10                  15

Arg Ile Gly Asp Lys Leu Ala Glu Arg Ile Ile Glu Tyr Arg Gln Lys
            20                  25                  30

His Gly Pro Phe Lys Ser Ile Glu Glu Ile Lys Asn Val Asn Gly Ile
        35                  40                  45

Gly Glu Lys Ile Phe Glu Ser Ile Lys Asp Ser Ile Thr
    50                  55                  60
```

<210> SEQ ID NO 106
<211> LENGTH: 61
<212> TYPE: PRT
<213> ORGANISM: Caldicellulosiruptor kronotskyensis

<400> SEQUENCE: 106

```
Lys Ile Asn Ile Asn Thr Ala Thr Lys Glu Glu Leu Lys Thr Leu Asn
1               5                   10                  15

Arg Ile Gly Asp Lys Leu Ala Glu Arg Ile Ile Glu Tyr Arg Gln Lys
            20                  25                  30

His Gly Pro Phe Lys Ser Ile Glu Glu Ile Lys Asn Val Asn Gly Ile
        35                  40                  45

Gly Glu Lys Ile Phe Glu Ser Ile Lys Asp Ser Ile Thr
    50                  55                  60
```

<210> SEQ ID NO 107
<211> LENGTH: 60
<212> TYPE: PRT
<213> ORGANISM: Desulfofundulus kuznetsovii

<400> SEQUENCE: 107

Val Asn Ile Asn Thr Ala Asp Gln Lys Glu Leu Glu Thr Leu Pro Gly
1               5                   10                  15

Ile Gly Pro Ser Leu Ala Gln Arg Ile Ile Gln Tyr Arg Glu Thr Asn
            20                  25                  30

Gly Pro Phe Lys Val Pro Glu Asp Ile Lys Asn Val Ser Gly Ile Gly
        35                  40                  45

Asp Lys Arg Phe Glu Gln Leu Lys Asp Tyr Ile Thr
    50                  55                  60

<210> SEQ ID NO 108
<211> LENGTH: 61
<212> TYPE: PRT
<213> ORGANISM: Thermoanaerobacterium xylanolyticum

<400> SEQUENCE: 108

Lys Ile Asn Ile Asn Thr Ala Thr Lys Glu Glu Leu Asp Thr Leu Pro
1               5                   10                  15

Gly Ile Gly Glu Val Thr Ala Gln Arg Ile Ile Asp Phe Arg Glu Gln
            20                  25                  30

His Gly Asn Phe Gln Arg Ile Glu Asp Ile Met Asn Val Ser Arg Ile
        35                  40                  45

Gly Pro Lys Leu Phe Glu Gln Ile Lys Asp Lys Ile Thr
    50                  55                  60

<210> SEQ ID NO 109
<211> LENGTH: 61
<212> TYPE: PRT
<213> ORGANISM: Thermoanaerobacterium thermosaccharolyticum

<400> SEQUENCE: 109

Lys Ile Asn Ile Asn Lys Ala Thr Lys Glu Glu Leu Asp Thr Leu Pro
1               5                   10                  15

Gly Ile Gly Glu Val Thr Ala Gln Arg Ile Ile Asp Phe Arg Glu Gln
            20                  25                  30

His Gly Asn Phe Gln Lys Ile Glu Asp Ile Met Asn Val Ser Arg Ile
        35                  40                  45

Gly Pro Lys Leu Phe Glu Gln Ile Lys Asp Lys Ile Thr
    50                  55                  60

<210> SEQ ID NO 110
<211> LENGTH: 63
<212> TYPE: PRT
<213> ORGANISM: Caldanaerobacter subterraneus

<400> SEQUENCE: 110

Ala Lys Lys Val Asn Ile Asn Thr Ala Thr Lys Glu Glu Leu Gln Thr
1               5                   10                  15

Leu Pro Gly Ile Gly Pro Val Thr Ala Glu Arg Ile Ile Glu Phe Arg
            20                  25                  30

Glu Thr Lys Gly Pro Phe Lys Lys Ile Glu Asp Ile Met Asn Val Pro
        35                  40                  45

Arg Ile Gly Pro Lys Met Phe Glu Gln Ile Lys Asp Lys Ile Thr
    50                  55                  60

<210> SEQ ID NO 111
<211> LENGTH: 61
<212> TYPE: PRT

-continued

```
<213> ORGANISM: Thermoanaerobacter sp.

<400> SEQUENCE: 111

Lys Ile Asn Ile Asn Thr Ala Thr Arg Glu Glu Leu Gln Thr Leu Pro
1               5                   10                  15

Gly Ile Gly Pro Val Thr Ala Glu Arg Ile Ile Glu Phe Arg Glu Ser
            20                  25                  30

Lys Gly Pro Phe Lys Lys Ile Glu Asp Ile Val Asn Val Ser Arg Ile
        35                  40                  45

Gly Pro Lys Met Phe Glu Gln Ile Lys Asp Lys Ile Thr
    50                  55                  60

<210> SEQ ID NO 112
<211> LENGTH: 64
<212> TYPE: PRT
<213> ORGANISM: Thermoanaerobacter wiegelii

<400> SEQUENCE: 112

Lys Ser Glu Lys Ile Asn Ile Asn Thr Ala Thr Lys Glu Glu Leu Gln
1               5                   10                  15

Thr Leu Pro Gly Ile Gly Pro Val Thr Ala Glu Arg Ile Ile Glu Phe
            20                  25                  30

Arg Glu Ser Lys Gly Ser Phe Lys Lys Ile Glu Asp Ile Met Asn Val
        35                  40                  45

Pro Arg Ile Gly Pro Lys Met Phe Glu Gln Ile Lys Asp Lys Ile Thr
    50                  55                  60

<210> SEQ ID NO 113
<211> LENGTH: 64
<212> TYPE: PRT
<213> ORGANISM: Thermoanaerobacter italicus

<400> SEQUENCE: 113

Lys Ser Glu Lys Ile Asn Ile Asn Thr Ala Thr Lys Glu Glu Leu Glu
1               5                   10                  15

Thr Leu Pro Gly Ile Gly Pro Val Thr Ala Glu Arg Ile Ile Glu Phe
            20                  25                  30

Arg Glu Asn Lys Gly Phe Phe Lys Lys Ile Glu Asp Ile Met Asn Val
        35                  40                  45

Pro Arg Ile Gly Pro Lys Met Phe Glu Gln Ile Lys Asp Lys Ile Thr
    50                  55                  60

<210> SEQ ID NO 114
<211> LENGTH: 64
<212> TYPE: PRT
<213> ORGANISM: Thermoanaerobacter sp.

<400> SEQUENCE: 114

Lys Ser Glu Lys Ile Asn Ile Asn Thr Ala Thr Lys Glu Glu Leu Glu
1               5                   10                  15

Thr Leu Pro Gly Ile Gly Pro Val Thr Ala Glu Arg Ile Ile Glu Phe
            20                  25                  30

Arg Glu Asn Lys Gly Phe Phe Lys Lys Ile Glu Asp Ile Met Asn Val
        35                  40                  45

Pro Arg Ile Gly Pro Lys Met Phe Glu Gln Ile Lys Asp Lys Ile Thr
    50                  55                  60

<210> SEQ ID NO 115
<211> LENGTH: 60
```

```
<212> TYPE: PRT
<213> ORGANISM: Marinitoga piezophila

<400> SEQUENCE: 115

Glu Ile Lys Ile Asp Leu Tyr Thr Ala Ser Glu Thr Gln Leu Thr Lys
1               5                   10                  15

Ile Pro Gly Ile Gly Pro Lys Thr Ala Lys Lys Ile Ile Gln Tyr Arg
            20                  25                  30

Glu Lys Tyr Gly Phe Ser Ser Val Lys Asp Leu Met Lys Ile Lys Gly
        35                  40                  45

Ile Gly Glu Lys Thr Tyr Glu Lys Ile Arg Lys Tyr
        50                  55                  60

<210> SEQ ID NO 116
<211> LENGTH: 60
<212> TYPE: PRT
<213> ORGANISM: Symbiobacterium thermophilum

<400> SEQUENCE: 116

Val Asn Ile Asn Thr Ala Gly Gln Ala Glu Leu Glu Thr Val Pro Gly
1               5                   10                  15

Ile Gly Pro Ala Leu Ala Arg Ala Ile Ile Thr Tyr Arg Thr Glu His
            20                  25                  30

Gly Pro Phe Gln Ser Val Asp Asp Leu Ile Asn Val Ser Gly Ile Gly
        35                  40                  45

Ser Lys Thr Leu Glu Lys Ile Arg Pro Tyr Val Thr
        50                  55                  60

<210> SEQ ID NO 117
<211> LENGTH: 139
<212> TYPE: PRT
<213> ORGANISM: Unknown
<220> FEATURE:
<221> NAME/KEY: source
<223> OTHER INFORMATION: /note="Description of Unknown:
      unclassified Thermotoga sequence"

<400> SEQUENCE: 117

Val Val Ala Phe Pro Val Glu Leu Asn Thr Ala Ser Leu Glu Asp Leu
1               5                   10                  15

Met Ser Ile Pro Gly Ile Gly Pro Val Lys Ala Gln Arg Ile Ile Asp
            20                  25                  30

Tyr Arg Glu Ser His Gly Gly Phe Ser Ser Val Glu Glu Leu Lys Asn
        35                  40                  45

Val Ser Gly Ile Gly Glu Lys Thr Leu Glu Lys Ile Ser Arg Tyr Val
        50                  55                  60

Thr Val Glu Gly Val Glu Gln His Ile Lys Arg Glu Val Thr Lys Leu
65                  70                  75                  80

Asn Val Asn Thr Ala Ser Val Glu Glu Leu Glu Thr Leu Pro Tyr Ile
                85                  90                  95

Gly Glu Val Lys Ala Lys Ala Ile Val Glu Tyr Arg Glu Lys Asn Gly
            100                 105                 110

Pro Phe Arg Ser Pro Glu Asp Leu Leu Asp Val Pro Gly Ile Gly Glu
        115                 120                 125

Lys Thr Leu Glu Lys Ile Arg Gly Lys Ile Thr
        130                 135

<210> SEQ ID NO 118
<211> LENGTH: 139
```

```
<212> TYPE: PRT
<213> ORGANISM: Thermotoga sp.

<400> SEQUENCE: 118

Val Thr Ser Phe Pro Ile Asp Leu Asn Ser Ala Ser Val Glu Asp Leu
1               5                   10                  15

Met Ser Ile Pro Gly Ile Gly Pro Val Lys Ala Gln Arg Ile Val Glu
                20                  25                  30

Tyr Arg Arg Ile Arg Gly Lys Phe Ser Thr Val Glu Glu Leu Thr Asn
            35                  40                  45

Val Ser Gly Ile Gly Glu Lys Thr Leu Glu Lys Ile Ser Lys Tyr Val
        50                  55                  60

Thr Val Glu Gly Val Glu Gln Pro Phe Arg Ser Glu Val Thr Lys Leu
65                  70                  75                  80

Asn Val Asn Thr Ala Ser Leu Glu Glu Leu Glu Thr Leu Pro Tyr Ile
                85                  90                  95

Gly Glu Ala Lys Ala Arg Ala Ile Ile Glu Tyr Arg Glu Glu His Gly
                100                 105                 110

Pro Phe Ser Ser Pro Glu Asp Leu Leu Asn Val Pro Gly Ile Gly Glu
            115                 120                 125

Lys Thr Leu Glu Arg Ile Arg Gly Lys Ile Thr
        130                 135

<210> SEQ ID NO 119
<211> LENGTH: 141
<212> TYPE: PRT
<213> ORGANISM: Thermosipho melanesiensis

<400> SEQUENCE: 119

Ala Glu Gln Ile Ile Asp Ile Asn Ser Ala Thr Phe Glu Gln Leu Val
1               5                   10                  15

Ser Leu Pro Gly Ile Gly Pro Thr Lys Ala Lys Ser Ile Ile Asn Tyr
                20                  25                  30

Arg Glu Lys Val Gly Glu Phe Leu Ser Ile Asp Asp Leu Leu Asn Val
            35                  40                  45

Ser Gly Ile Gly Pro Ser Thr Leu Lys Lys Ile Lys Pro Phe Ile Lys
        50                  55                  60

Ile Lys Thr Ala Asn Val Ile Thr Asn Ser Pro Ser Gly Ser Glu Asp
65                  70                  75                  80

Val Lys Ile Asn Ile Asn Asn Ala Ser Val Glu Glu Leu Met Lys Leu
                85                  90                  95

Pro Gly Ile Gly Lys Val Lys Ala Gln Glu Ile Ile Glu Phe Arg Lys
                100                 105                 110

Lys Phe Gly Asn Val Gln Ser Phe Glu Asp Leu Leu Lys Val Lys Gly
            115                 120                 125

Ile Gly Lys Lys Thr Leu Glu Lys Ile Lys Pro Phe Ile
        130                 135                 140

<210> SEQ ID NO 120
<211> LENGTH: 137
<212> TYPE: PRT
<213> ORGANISM: Pseudothermotoga thermarum

<400> SEQUENCE: 120

Glu Phe Pro Ile Asp Ile Asn Lys Ala Ser Tyr Glu Glu Leu Leu Val
1               5                   10                  15

Leu Pro Gly Ile Gly Pro Thr Lys Ala Arg Ala Ile Val Glu Tyr Arg
```

-continued

```
                 20                    25                   30

Gln Lys Tyr Gly Pro Phe Glu Ser Leu Pro Asp Leu Ala Lys Val Ser
         35                    40                   45

Gly Ile Gly Lys Lys Thr Val Glu Arg Leu Ala Asn Phe Val Lys Ile
     50                    55                   60

Glu Gly Thr Val Phe Val Lys Met Glu Glu Lys Arg Arg Ile Asn Val
65                    70                   75                   80

Asn Ile Ala Thr Leu Glu Gln Leu Cys Glu Leu Pro Gly Ile Gly Glu
                 85                    90                   95

Val Lys Ala Ser Gln Ile Ile Lys Tyr Arg Gln Glu Asn Gly Pro Phe
                 100                   105                  110

Lys Lys Pro Glu Asp Leu Leu Lys Val Pro Gly Ile Gly Pro Lys Thr
         115                   120                  125

Leu Glu Lys Ile Lys Asp Phe Ile Thr
     130                   135

<210> SEQ ID NO 121
<211> LENGTH: 60
<212> TYPE: PRT
<213> ORGANISM: Thermodesulfatator indicus

<400> SEQUENCE: 121

Ile Asn Leu Asn Val Ala Gly Gln Glu Glu Leu Ala Asn Leu Pro Gly
1                 5                    10                   15

Val Gly Pro Lys Ile Ala Ala Ala Ile Val Glu Tyr Arg Glu Lys Tyr
                 20                    25                   30

Gly Pro Phe Lys Ser Val Asp Glu Leu Leu Glu Ile Lys Gly Ile Gly
         35                    40                   45

Pro Lys Lys Leu Glu Lys Ile Arg Pro Leu Val Thr
     50                    55                   60

<210> SEQ ID NO 122
<211> LENGTH: 60
<212> TYPE: PRT
<213> ORGANISM: Thermodesulfobacterium geofontis

<400> SEQUENCE: 122

Lys Ile Asp Ile Asn Gln Ala Thr Val Glu Glu Leu Glu Lys Leu Pro
1                 5                    10                   15

Gly Ile Gly Pro Lys Ile Ala Lys Asn Ile Val Glu Tyr Arg Glu Lys
                 20                    25                   30

Asn Gly Pro Phe Arg Ser Ile Glu Glu Leu Leu Lys Val Lys Gly Ile
         35                    40                   45

Gly Pro Lys Lys Leu Glu Gln Ile Lys Lys Tyr Leu
     50                    55                   60

<210> SEQ ID NO 123
<211> LENGTH: 139
<212> TYPE: PRT
<213> ORGANISM: Thermosipho africanus

<400> SEQUENCE: 123

Ser Gln Ile Ile Asp Leu Asn Lys Ala Asp Leu Glu Gln Leu Met Ser
1                 5                    10                   15

Leu Pro Gly Ile Gly Thr Val Lys Ala Lys Ala Ile Ile Ser Tyr Arg
                 20                    25                   30

Gln Ala His Gly Asn Phe Asn Ser Ile Asp Asp Leu Ile Asn Val Thr
         35                    40                   45
```

-continued

```
Gly Ile Gly Pro Ser Thr Leu Glu Lys Ile Arg Asp Tyr Val Thr Val
    50              55              60

Ser Lys Thr Asn Glu Val Gln Ile Asn Met Asn Asn Glu Leu Lys Lys
65              70              75              80

Ile Asn Ile Asn Lys Ala Asp Glu Lys Gln Leu Glu Lys Leu Pro Gly
            85              90              95

Ile Gly Pro Thr Lys Ala Lys Arg Ile Ile Glu Tyr Arg Glu Lys Asn
            100             105             110

Gly Lys Phe Asn Ser Leu Asn Glu Leu Leu Asn Val Asn Gly Ile Gly
        115             120             125

Pro Lys Thr Leu Glu Lys Ile Lys Asn Tyr Leu
    130             135
```

```
<210> SEQ ID NO 124
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Asn Thr Ala Ser Leu Glu Glu Leu Gln Thr Ile Ser Gly Ile Gly Ala
1               5               10              15

Lys Arg Ala Gln Asp Ile Ile Asp Tyr Arg Asp Asn Asn Gly Gly Phe
            20              25              30

Ser Ser Val Asp Asp Leu Lys Asn Val Ser Gly Ile Gly Glu Arg
        35              40              45
```

```
<210> SEQ ID NO 125
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Asn Thr Ala Ser Leu Glu Glu Leu Gln Thr Ile Ser Gly Ile Gly Ala
1               5               10              15

Lys Arg Ala Gln Asp Ile Ile Asp Tyr Arg Asp Asn Asn Gly Gly Phe
            20              25              30

Ser Ser Val Asp Asp Leu Lys Asn Val Ser Gly Phe Gly Glu Lys
        35              40              45
```

```
<210> SEQ ID NO 126
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ala Asp Thr Thr Gln Leu Met Gln Ile Arg Gly Ile Gly Arg Gly Ile
1               5               10              15

Ser Ala Arg Ile Val Ala Tyr Arg
            20
```

```
<210> SEQ ID NO 127
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Asn Thr Ala Ser Leu Glu Glu Leu Gln Thr Ile Ser Gly Ile Gly Ala
1               5                   10                  15

Lys Arg Ala Gln Asp Ile Ile Asp Tyr Arg Asp Asn Asn Gly Gly Phe
            20                  25                  30

Ser Ser Val Asp Asp Leu Lys Asn Val Ser Gly Ile Gly Glu Lys Thr
        35                  40                  45

<210> SEQ ID NO 128
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Ala Asp Thr Thr Gln Leu Met Gln Ile Arg Gly Ile Gly Arg Gly Ile
1               5                   10                  15

Ser Ala Arg Ile Val Ala Tyr Arg Ala Arg Leu Gly Gly Phe Val Arg
            20                  25                  30

Ala

<210> SEQ ID NO 129
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Asn Thr Ala Ser Leu Glu Asp Leu Met Ser Ile Pro Gly Ile Gly Pro
1               5                   10                  15

Val Lys Ala Gln Arg Ile Ile Asp Tyr Arg Glu Ser His Gly Gly Phe
            20                  25                  30

Ser Ser Val Glu Glu Leu Lys Asn Val Ser Gly Ile Gly Glu Lys Thr
        35                  40                  45

Leu Glu Lys
    50

<210> SEQ ID NO 130
<211> LENGTH: 305
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Met Ala Gly Ser His His His His His His Gly Met Ala Ser Met Thr
1               5                   10                  15
```

-continued

```
Gly Gly Gln Gln Met Gly Arg Ser Gly Asp Asp Asp Lys Gly Leu
            20                  25                  30

Asn Asp Ile Phe Glu Ala Gln Lys Ile Glu Trp His Glu Leu Lys Ile
            35                  40                  45

Ala Ala Phe Asn Ile Arg Thr Phe Gly Glu Thr Lys Met Ser Asn Ala
        50                  55                  60

Thr Leu Ala Ser Tyr Ile Val Arg Ile Val Arg Arg Tyr Asp Ile Val
65                  70                  75                  80

Leu Ile Gln Glu Val Arg Asp Ser His Leu Val Ala Val Gly Lys Leu
                85                  90                  95

Leu Asp Tyr Leu Asn Gln Asp Asp Pro Asn Thr Tyr His Tyr Val Val
            100                 105                 110

Ser Glu Pro Leu Gly Arg Asn Ser Tyr Lys Glu Arg Tyr Leu Phe Leu
            115                 120                 125

Phe Arg Pro Asn Lys Val Ser Val Leu Asp Thr Tyr Gln Tyr Asp Asp
        130                 135                 140

Gly Cys Glu Ser Cys Gly Asn Asp Ser Phe Ser Arg Glu Pro Ala Val
145                 150                 155                 160

Val Lys Phe Ser Ser His Ser Thr Lys Val Lys Glu Phe Ala Ile Val
                165                 170                 175

Ala Leu His Ser Ala Pro Ser Asp Ala Val Ala Glu Ile Asn Ser Leu
            180                 185                 190

Tyr Asp Val Tyr Leu Asp Val Gln Gln Lys Trp His Leu Asn Asp Val
            195                 200                 205

Met Leu Met Gly Asp Phe Asn Ala Asp Cys Ser Tyr Val Thr Ser Ser
        210                 215                 220

Gln Trp Ser Ser Ile Arg Leu Arg Thr Ser Ser Thr Phe Gln Trp Leu
225                 230                 235                 240

Ile Pro Asp Ser Ala Asp Thr Thr Ala Thr Ser Thr Asn Cys Ala Tyr
                245                 250                 255

Asp Arg Ile Val Val Ala Gly Ser Leu Leu Gln Ser Ser Val Val Pro
            260                 265                 270

Gly Ser Ala Ala Pro Phe Asp Phe Gln Ala Ala Tyr Gly Leu Ser Asn
            275                 280                 285

Glu Met Ala Leu Ala Ile Ser Asp His Tyr Pro Val Glu Val Thr Leu
        290                 295                 300

Thr
305
```

```
<210> SEQ ID NO 131
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 131
```

```
His His His His His His
1               5
```